United States Patent
Bhebe et al.

(10) Patent No.: US 12,325,737 B2
(45) Date of Patent: Jun. 10, 2025

(54) TOTAL AFUCOSYLATED GLYCOFORMS OF ANTIBODIES PRODUCED IN CELL CULTURE

(71) Applicant: AMGEN INC., Thousand Oaks, CA (US)

(72) Inventors: Prince Bhebe, Thousand Oaks, CA (US); Matthew Jerums, Thousand Oaks, CA (US); Irene Liu, Thousand Oaks, CA (US); Kurt Kunas, Thousand Oaks, CA (US)

(73) Assignee: AMGEN INC., Thousand Oaks, CA (US)

(*) Notice: Subject to any disclaimer, the term of this patent is extended or adjusted under 35 U.S.C. 154(b) by 811 days.

(21) Appl. No.: 17/040,422

(22) PCT Filed: Mar. 26, 2019

(86) PCT No.: PCT/US2019/024154
§ 371 (c)(1),
(2) Date: Sep. 22, 2020

(87) PCT Pub. No.: WO2019/191150
PCT Pub. Date: Oct. 3, 2019

(65) Prior Publication Data
US 2021/0079065 A1 Mar. 18, 2021

Related U.S. Application Data

(60) Provisional application No. 62/648,308, filed on Mar. 26, 2018.

(51) Int. Cl.
*C07K 16/00* (2006.01)
*C07K 16/30* (2006.01)
*C12P 21/00* (2006.01)

(52) U.S. Cl.
CPC ............. *C07K 16/00* (2013.01); *C07K 16/30* (2013.01); *C12P 21/005* (2013.01); *C07K 2317/14* (2013.01); *C07K 2317/41* (2013.01); *C07K 2317/51* (2013.01); *C07K 2317/515* (2013.01); *C07K 2317/732* (2013.01)

(58) Field of Classification Search
CPC .... C07K 16/00; C07K 16/30; C07K 2317/14; C07K 2317/41; C07K 2317/51; C07K 2317/515; C07K 2317/732; C07K 16/2887; C12P 21/005
See application file for complete search history.

(56) References Cited

U.S. PATENT DOCUMENTS

| | | |
|---|---|---|
| 5,856,179 A | 1/1999 | Chen et al. |
| 6,143,874 A | 11/2000 | Chang |
| 6,156,570 A | 12/2000 | Hu et al. |
| 6,171,586 B1 | 1/2001 | Lam et al. |
| 6,180,401 B1 | 1/2001 | Chen et al. |
| 6,184,359 B1 | 2/2001 | Grabstein et al. |
| 6,232,447 B1 | 5/2001 | Cerretti |
| 6,235,883 B1 | 5/2001 | Jakobovits et al. |
| 6,319,499 B1 | 11/2001 | Elliott |
| 6,355,779 B1 | 3/2002 | Goodwin et al. |
| 6,500,429 B2 | 12/2002 | Boone et al. |
| 6,596,852 B2 | 7/2003 | Cerretti et al. |
| 6,630,143 B1 | 10/2003 | Lyman et al. |
| 6,682,736 B1 | 1/2004 | Hanson et al. |
| 6,692,740 B2 | 2/2004 | Sims et al. |
| 6,716,587 B2 | 4/2004 | Mosley et al. |
| 6,740,522 B2 | 5/2004 | Anderson |
| 6,849,450 B2 | 2/2005 | Langley et al. |
| 6,924,360 B2 | 8/2005 | Green et al. |
| 7,037,498 B2 | 5/2006 | Cohen et al. |
| 7,045,128 B2 | 5/2006 | Lyman et al. |
| 7,067,131 B2 | 6/2006 | Gudas et al. |
| 7,081,523 B2 | 7/2006 | Elliott |
| 7,084,257 B2 | 8/2006 | Deshpande et al. |
| 7,090,844 B2 | 8/2006 | Bar-Eli et al. |
| 7,109,003 B2 | 9/2006 | Hanson et al. |
| 7,132,281 B2 | 11/2006 | Hanson et al. |
| 7,135,174 B2 | 11/2006 | Corvalan et al. |
| 7,138,500 B1 | 11/2006 | Goodwin et al. |
| 7,141,653 B2 | 11/2006 | Greenfeder et al. |
| 7,144,731 B2 | 12/2006 | Zsebo et al. |

(Continued)

FOREIGN PATENT DOCUMENTS

| | | |
|---|---|---|
| WO | 2002/101019 A2 | 12/2002 |
| WO | 2005/089182 A2 | 9/2005 |

(Continued)

OTHER PUBLICATIONS

Pereira et al., MABS 10: 693-17, 2018 (Year: 2018).*
Therom Fisher technical reference library: Gibco Cell Culture Basics, online published before 2017 (Year: 2017).*
Millipore Sigma, mammalian cell culture > Glucose in cell culture, online published before 2017 (Year: 2017).*
Aghamohseni et al., "Effects of nutrient levels and average culture pH on the glycosylation pattern of camelid-humanized monoclonal antibody," *Journal of Biotechnology* 186: 98-109 (2014).
Becker and Lowe, "Fucose: biosynthesis and biological function in mammals," *Glycobiology* 13(7): 41R-53R (2003).

(Continued)

*Primary Examiner* — Lei Yao
(74) *Attorney, Agent, or Firm* — Julie J. Hong

(57) ABSTRACT

Provided herein are methods of producing an antibody composition comprising a desired or predetermined or preselected level of total afucosylated (TAF) glycoforms. In exemplary embodiments, the method comprises maintaining glycosylation-competent cells in a cell culture medium comprising fucose and/or glucose at a specific concentration as described herein, depending on the level of TAF glycoforms desired. Related compositions comprising glycosylated proteins and TAF glycoforms thereof are also provided herein. Also provided are cell culture media.

15 Claims, 15 Drawing Sheets
Specification includes a Sequence Listing.

(56) References Cited

U.S. PATENT DOCUMENTS

| | | |
|---|---|---|
| 7,186,809 B2 | 3/2007 | Pluenneke |
| 7,193,058 B2 | 3/2007 | Cosman et al. |
| 7,199,224 B2 | 4/2007 | Black et al. |
| 7,202,343 B2 | 4/2007 | Gudas et al. |
| 7,265,212 B2 | 9/2007 | Babcook et al. |
| 7,267,960 B2 | 9/2007 | Galibert et al. |
| 7,270,817 B2 | 9/2007 | Sims et al. |
| 7,285,269 B2 | 10/2007 | Babcook et al. |
| 7,288,251 B2 | 10/2007 | Bedian et al. |
| 7,288,253 B2 | 10/2007 | Roskos et al. |
| 7,304,144 B2 | 12/2007 | Sims et al. |
| 7,317,090 B2 | 1/2008 | Mosley et al. |
| 7,318,925 B2 | 1/2008 | Roskos et al. |
| 7,326,414 B2 | 2/2008 | Bedian et al. |
| 7,335,743 B2 | 2/2008 | Welcher et al. |
| 7,338,660 B2 | 3/2008 | Bedian et al. |
| 7,371,381 B2 | 5/2008 | Aaron et al. |
| 7,378,091 B2 | 5/2008 | Gudas et al. |
| 7,411,050 B2 | 8/2008 | Anderson |
| 7,411,057 B2 | 8/2008 | Hanson et al. |
| 7,422,742 B2 | 9/2008 | Greenfeder et al. |
| 7,423,128 B2 | 9/2008 | Gazit-Bornstein et al. |
| 7,427,669 B2 | 9/2008 | Cosman et al. |
| 7,429,491 B2 | 9/2008 | Luan et al. |
| 7,435,796 B1 | 10/2008 | Yoshinaga |
| 7,438,910 B2 | 10/2008 | Varnum et al. |
| 7,449,555 B2 | 11/2008 | Fanslow, III et al. |
| 7,465,450 B2 | 12/2008 | Pluenneke |
| 7,498,420 B2 | 3/2009 | Michaud et al. |
| 7,521,048 B2 | 4/2009 | Gliniack et al. |
| 7,521,053 B2 | 4/2009 | Oliner |
| 7,537,762 B2 | 5/2009 | North et al. |
| 7,541,438 B2 | 6/2009 | Tamatani et al. |
| 7,563,442 B2 | 7/2009 | Bedian et al. |
| 7,566,772 B2 | 7/2009 | Green et al. |
| 7,569,387 B2 | 8/2009 | Theill et al. |
| 7,579,186 B1 | 8/2009 | Sakamoto et al. |
| 7,585,500 B2 | 9/2009 | Foltz et al. |
| 7,592,429 B2 | 9/2009 | Paszty et al. |
| 7,592,430 B2 | 9/2009 | Bedian et al. |
| 7,601,818 B2 | 10/2009 | Wild, Jr. et al. |
| 7,618,633 B2 | 11/2009 | Bedian et al. |
| 7,626,012 B2 | 12/2009 | Bedian et al. |
| 7,628,986 B2 | 12/2009 | Weber et al. |
| 7,638,606 B2 | 12/2009 | Carter et al. |
| 7,658,924 B2 | 2/2010 | Oliner et al. |
| 7,695,948 B2 | 4/2010 | Black et al. |
| 7,700,742 B2 | 4/2010 | Cohen et al. |
| 7,704,501 B2 | 4/2010 | Anderson |
| 7,705,130 B2 | 4/2010 | Rothe et al. |
| 7,709,611 B2 | 5/2010 | Li et al. |
| 7,718,776 B2 | 5/2010 | Boyle et al. |
| 7,728,110 B2 | 6/2010 | Babcook et al. |
| 7,728,113 B2 | 6/2010 | Bedian et al. |
| 7,736,644 B2 | 6/2010 | Weber et al. |
| 7,741,115 B2 | 6/2010 | Baum et al. |
| 7,767,206 B2 | 8/2010 | Tocker et al. |
| 7,767,793 B2 | 8/2010 | Sims |
| 7,786,271 B2 | 8/2010 | Sims et al. |
| 7,786,284 B2 | 8/2010 | Tocker et al. |
| 7,790,859 B2 | 9/2010 | Welcher et al. |
| 7,795,413 B2 | 9/2010 | Wild, Jr. et al. |
| 7,807,159 B2 | 10/2010 | Chin et al. |
| 7,807,795 B2 | 10/2010 | Boyle |
| 7,807,796 B2 | 10/2010 | Cosman et al. |
| 7,807,797 B2 | 10/2010 | Hanson et al. |
| 7,807,798 B2 | 10/2010 | Jakobovits et al. |
| 7,815,907 B2 | 10/2010 | Cohen et al. |
| 7,824,679 B2 | 11/2010 | Hanson et al. |
| 7,833,527 B2 | 11/2010 | Tocker et al. |
| 7,867,494 B2 | 1/2011 | Liu et al. |
| 7,868,140 B2 | 1/2011 | Siu et al. |
| 7,871,611 B2 | 1/2011 | Calzone et al. |
| 7,872,106 B2 | 1/2011 | Paszty et al. |
| 7,872,113 B2 | 1/2011 | Carter et al. |
| 7,879,323 B2 | 2/2011 | Thomason et al. |
| 7,887,799 B2 | 2/2011 | Thomason et al. |
| 7,888,482 B2 | 2/2011 | Virca et al. |
| 7,906,625 B2 | 3/2011 | Shen et al. |
| 7,915,391 B2 | 3/2011 | Ng et al. |
| 7,923,008 B2 | 4/2011 | Boyle |
| 7,932,372 B2 | 4/2011 | Pullen et al. |
| 7,939,070 B2 | 5/2011 | Tocker et al. |
| 7,939,640 B2 | 5/2011 | Baum |
| 7,947,809 B2 | 5/2011 | Yan et al. |
| 7,964,193 B2 | 6/2011 | Green et al. |
| 8,093,045 B2 | 1/2012 | Pla et al. |
| 8,663,945 B2 | 3/2014 | Pla et al. |
| 8,906,646 B2 | 12/2014 | Pla et al. |
| 9,073,988 B2 | 7/2015 | Pla et al. |
| 9,090,867 B2 | 7/2015 | Pla et al. |
| 9,150,645 B2 | 10/2015 | Subramanian et al. |
| 9,234,032 B2 | 1/2016 | Pla et al. |
| 9,283,371 B2 | 3/2016 | Duncan |
| 9,284,371 B2 | 3/2016 | Pla et al. |
| 9,481,901 B2 | 11/2016 | Huang et al. |
| 2003/0103978 A1 | 6/2003 | Deshpande et al. |
| 2004/0093621 A1* | 5/2004 | Shitara ............ A61P 35/00 800/6 |
| 2006/0127393 A1 | 6/2006 | Li et al. |
| 2007/0196376 A1 | 8/2007 | Raeber et al. |
| 2008/0166352 A1 | 7/2008 | Siu et al. |
| 2008/0182976 A1 | 7/2008 | Elliott |
| 2008/0286284 A1 | 11/2008 | Maddon et al. |
| 2008/0292639 A1 | 11/2008 | Shen et al. |
| 2009/0041784 A1 | 2/2009 | Yan et al. |
| 2009/0155164 A1 | 6/2009 | Brasel et al. |
| 2009/0155274 A1 | 6/2009 | Wild, Jr. et al. |
| 2009/0191212 A1 | 7/2009 | Oliner et al. |
| 2009/0208489 A1 | 8/2009 | Veiby et al. |
| 2009/0214559 A1 | 8/2009 | Varnum et al. |
| 2009/0226447 A1 | 9/2009 | Boone et al. |
| 2009/0234106 A1 | 9/2009 | Han et al. |
| 2009/0238823 A1 | 9/2009 | Comeau et al. |
| 2009/0263383 A1 | 10/2009 | Smothers et al. |
| 2010/0040619 A1 | 2/2010 | Li et al. |
| 2010/0047253 A1 | 2/2010 | Foltz et al. |
| 2010/0098694 A1 | 4/2010 | Bedian et al. |
| 2010/0111979 A1 | 5/2010 | Weber et al. |
| 2010/0197005 A1 | 8/2010 | Belouski et al. |
| 2010/0209435 A1 | 8/2010 | Boyle et al. |
| 2010/0254975 A1 | 10/2010 | Hsu et al. |
| 2010/0255538 A1 | 10/2010 | Cohen et al. |
| 2010/0304436 A1 | 12/2010 | Chen et al. |
| 2010/0305307 A1 | 12/2010 | Jakobovits et al. |
| 2011/0014201 A1 | 1/2011 | Smith et al. |
| 2011/0027287 A1 | 2/2011 | Jackson et al. |
| 2011/0040076 A1 | 2/2011 | Wild, Jr. et al. |
| 2011/0044986 A1 | 2/2011 | Biere-Citron et al. |
| 2011/0045537 A1 | 2/2011 | Welcher et al. |
| 2011/0059063 A1 | 3/2011 | Virca et al. |
| 2011/0091455 A1 | 4/2011 | Chin et al. |
| 2011/0135657 A1 | 6/2011 | Hu et al. |
| 2011/0150888 A1 | 6/2011 | Foltz et al. |
| 2011/0165171 A1 | 7/2011 | Virca et al. |
| 2012/0277165 A1 | 11/2012 | Collins et al. |
| 2014/0356910 A1 | 12/2014 | Huang et al. |
| 2016/0115225 A1 | 4/2016 | Chumsae et al. |
| 2020/0087698 A1 | 3/2020 | Wu et al. |

FOREIGN PATENT DOCUMENTS

| | | |
|---|---|---|
| WO | 2006/125821 A2 | 11/2006 |
| WO | 2007/115813 A1 | 10/2007 |
| WO | 2008/052030 A2 | 5/2008 |
| WO | 2008/128227 A1 | 10/2008 |
| WO | 2010/141478 A1 | 12/2010 |
| WO | 2010/141855 A1 | 12/2010 |
| WO | 2011/019622 A1 | 2/2011 |
| WO | 2011/127322 A1 | 10/2011 |
| WO | 2012/041768 A1 | 4/2012 |
| WO | 2013/013013 A2 | 1/2013 |
| WO | 2013/114164 A1 | 8/2013 |
| WO | 2013/114167 A1 | 8/2013 |

(56) References Cited

FOREIGN PATENT DOCUMENTS

| WO | 2013/114245 | A1 | 8/2013 |
| WO | 2014/055370 | A1 | 4/2014 |
| WO | 2014/159488 | A1 | 10/2014 |
| WO | 2015/011660 | A1 | 1/2015 |
| WO | 2015/128314 | A1 | 9/2015 |
| WO | 2015/128793 | A1 | 9/2015 |
| WO | 2015/140700 | A1 | 9/2015 |
| WO | 2015/140708 | A1 | 9/2015 |
| WO | 2016/089919 | A1 | 6/2016 |
| WO | 2017/031114 | A1 | 2/2017 |
| WO | 2017/079165 | A1 | 5/2017 |
| WO | 2017/081093 | A1 | 5/2017 |
| WO | 2017/120347 | A1 | 7/2017 |
| WO | 2017/120359 | A1 | 7/2017 |
| WO | 2017/134667 | A1 | 8/2017 |
| WO | WO2017134667 | * | 8/2017 |

OTHER PUBLICATIONS

Brunner et al., "Investigation of the interactions of critical scale-up parameters (pH, pO$_2$ and pCO$_2$) on CHO batch performance and critical quality attributes," *Bioprocess Biosyst Eng* 40: 251-263 (2017).

Burleigh et al., "Synergizing metabolic flux analysis and nucleotide sugar metabolism to understand the control of glycosylation of recombinant protein in CHO cells," *BMC Biotechnology* 11: 95 (2011).

Chaplen, "Incidence and potential implications of the toxic metabolite methylglyoxal in cell culture: A review," *Cytotechnology* 26: 173-183 (1998).

Chothia et al., "Conformations of immunoglobulin hypervariable regions," *Nature* 342: 877-883 (1989).

Chothia and Lesk, "Canonical Structures for the Hypervariable Regions of Immunoglobulins," *J. Mol. Biol.* 196: 901-917 (1987).

Costa et al., "The impact of microcarrier culture optimization on the glycosylation profile of a monoclonal antibody," *SpringerPlus* 2(1): 1-10 (2013).

Cox and Genser, "Studies on the Effects of Simple Sugars on Mammalian Cells in Culture and Characterization of the Inhibition of 3T3 Fibroblasts by L-Fucose," *Cancer Research* 28(6): 1162-1172 (1968).

Da Silva et al., "Target-directed development and preclinical characterization of the proposed biosimilar rituximab GP2013," *Leukemia & Lymphoma* 55(7): 1609-1617 (2014).

Fan et al., "Amino Acid and Glucose Metabolism in Fed-Batch CHO Cell Culture Affects Antibody Production and Glycosylation," *Biotechnology and Bioengineering* 112(3): 521-535 (2015).

Field et al., "Structural analysis of the N-glycans from human immunoglobulin A1: comparison of normal human serum immunoglobulin A1 with that isolated from patents with rheumatoid arthritis," *Biochemical Journal* 299(1): 261-275 (1994).

Freimoser-Grundschober et al., "FcγRIIIa chromatography to enrich a-fucosylated glycoforms and assess the potency of glycoengineered therapeutic antibodies," *Journal of Chromatography A* 1610: 460554 (2020).

Frenzel et al., "Expression of recombinant antibodies," *Frontiers in Immunology* 4: 217 (2013).

Friend et al., "Phase I Study of an engineered aglycosylated humanized CD3 antibody in renal transplant rejection," *Transplantation* 68(11): 1632-1637 (1999).

Gaillet et al., "High-Level Recombinant Protein Production in CHO Cells Using an Adenoviral Vector and the Cumate Gene-Switch," *Biotechnol. Prog.* 23: 200-209 (2007).

Goetze et al., "High-mannose glycans on the Fc region of therapeutic IgG antibodies increase serum clearance in humans," *Glycobiology* 21(7): 949-959 (2011).

Gronemeyer et al., "Trends in Upstream and Downstream Process Development for Antibody Manufacturing," *Bioengineering* 1(4): 188-212 (2014).

Guile et al., "A Rapid High-Resolution High-Performance Liquid Chromatographic Method for Separating Glycan Mixtures and Analyzing Oligosaccharide Profiles," *Analytical Biochemistry* 240: 210-226 (1996).

Hayes et al., "Glycosylation and Fc Receptors," *Current Topics in Microbiology and Immunology* 382: 165-199 (2014).

Hirschberg et al., "Golgi nucleotide sugar transport and leukocyte adhesion deficiency II," *The Journal of Clinical Investigation* 108(1): 3-6 (2001).

Ho et al., "Fucosylation of a Therapeutic Antibody: Effects on Antibody-Dependent, Cell-Mediated Cytotoxicity (ADCC) Potency and Efficacy," *BioProcess International* 14(4) 30-38 (2016).

Hossler et al., "Optimal and consistent protein glycosylation in mammalian cell culture," *Glycobiology* 19(9): 936-949 (2009).

Huang et al., "A Robust Method for Increasing Fc Glycan High Mannose Level of Recombinant Antibodies," *Biotechnology and Bioengineering* 112(6): 1200-1209 (2015).

HyClone™ Media and Supplements (GE Healthcare) Data File 29136827 AA.

Imai-Nishiya, "Double knockdown of α1, 6-fucosyltransferase (FUT8) and GDP-mannose 4, 6-dehydratase (GMD) in antibody-producing cells: a new strategy for generating fully non-fucosylated therapeutic antibodies with enhanced ADCC," *BMC Biotechnology* 7:84 (2007).

Kanda et al., "Establishment of GDP-mannose 4,6-dehydratase (GMD) knockout host cell line: A new strategy for generating completely non-fucosylated recombinant therapeutics," *Journal of Biotechnology* 130: 300-310 (2007).

Khan, "Gene Expression in Mammalian Cells and its Applications," *Advanced Pharmaceutical Bulletin* 3(2): 257-263 (2013).

Khattak et al., "Feed Development for Fed-Batch CHO Production Process by Semisteady State Analysis," *Biotechnology Progress* 26(3): 797-804 (2010).

Konno et al., "Fucose content of monoclonal antibodies can be controlled by culture medium osmolality for high antibody-dependent cellular cytotoxicity," *Cytotechnology* 64: 249-265 (2012).

Mattu et al., "The Glycosylation and Structure of Human Serum IgA1, Fab, and Fc Regions and the Role of N-Glycosylation on Fcα Receptor Interactions," *The Journal of Biological Chemistry* 273(4): 2260-2272 (1998).

Nimmerjahn and Ravetch, "Divergent Immunoglobulin G Subclass Activity Through Selective Fc Receptor Binding," *Science* 310: 1510-1512 (2005).

Nordeen et al. "GOLAC: An Endogenous Anion Channel of the Golgi Complex," *Biophysical Journal* 78(6): 2918-2928 (2000).

Reusch and Tejada, "Fc glycans of therapeutic antibodies as critical quality attributes," *Glycobiology* 25(12): 1325-1334 (2015).

Rosenlocher et al., "Applying Acylated Fucose Analogues to Metabolic Glycoengineering," *Bioengineering* 2(4): 213-234 (2015).

Ruhaak et al., "Glycan labeling strategies and their use in identification and quantification," *Analytical and Bioanalytical Chemistry* 397(8): 3457-3481 (2010).

Shields et al., "Lack of Fucose on Human IgG1 N-Linked Oligosaccharide Improves Binding to Human FcγRIII and Antibody-dependent Cellular Toxicity," *Journal of Biological Chemistry* 277(30): 26733-26740 (2002).

Shimamoto et al., "Peptibodies: A flexible alternative format to antibodies," *mAbs* 4(5): 586-591 (2012).

Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," *The Journal of Biological Chemistry* 278(5): 3466-3473 (2003).

Song et al., "Inhibition of Tumor Growth in a Mouse Xenograft Model by the Humanized Anti-HGF Monoclonal Antibody YYB-101 Produced in a Large-Scale CHO Cell Culture," *J. Microbiol. Biotechnol.* 23(9): 1327-1338 (2013).

Spiess et al., "Alternative molecular formats and therapeutic applications for bispecific antibodies," *Molecular Immunology* 67(2): 97-106 (2015).

Van Horsten et al., "Production of non-fucosylated antibodies by co-expression of heterologous GDP-6-deoxy-D-lyxo-4-hexulose reductase," *Glycobiology* 20(12): 1607-1618 (2010).

(56) References Cited

OTHER PUBLICATIONS

Weiner, "Rituximab: Mechanism of Action," *Seminars in Hematology* 47(2): 115-123 (2010).
Wuhrer et al., "Protein glycosylation analysis by liquid chromatography—mass spectrometry," *Journal of Chromatography B* 825(2), pp. 124-133 (2005).
Yamane-Ohnuki et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," *Biotechnology and Bioengineering* 87(5): 614-622 (2004).
Yoo et al., "Differences in N-glycan structures found on recombinant IgA1 and IgA2 produced in murine myeloma and CHO cells lines," mAbs 2(3): 320-334 (2010).
Yu et al., "Production, characterization and pharmacokinetic properties of antibodies with N-linked Mannose-5 glycans," mAbs 4(4): 475-487 (2012).
Zhou et al., "Development of a Simple and Rapid Method for Producing Non-Fucosylated Oligomannose Containing Antibodies with Increased Effector Function," *Biotechnology and Bioengineering* 99(3): 652-665 (2008).
Dang et al., "Interaction of cell culture process parameters for modulating mAb afucosylation," Biotechnology and Bioengineering 116(4): 831-845 (2019).
Anonymous, "Dulbecco's Modified Eagle Medium (DMEM)," DiagnoCine, retrieved from: https://www.diagnocine.com/Content/Upload/Product/datasheets/AL151A_HiMedia_Diagnocine.pdf, revised Jan. 2011.
Anonymous, "Minimum Essential Medium Eagle (MEM)," DiagnoCine, retrieved from: https://www.diagnocine.com/Content/Upload/Product/datasheets/AL154A_HiMedia_Diagnocine.pdf, revised Jan. 2011.
Anonymous, "Nutrient Mixture F1-Ham," DiagnoCine, retrieved from: https://www.diagnocine.com/Content/Upload/Product/datasheets/AT024A_HiMedia_Diagnocine.pdf, revised Jan. 2011.
Anonymous, "RPMI 1640," DiagnoCine, retrieved from: https://www.diagnocine.com/Content/Upload/Product/datasheets/m%20(53).pdf, revised Jan. 2011.
Becker, "Genetic and Biochemical Determination of Fucosylated Glycan Expression," abstract of thesis from The University of Michigan, UMI31212891, 3 p. 2002.
Brühlmann et al., "Tailoring Recombinant Protein Quality by Rational Media Design," *Biotechnology Progress* 31(3):615-629 (2015).
Carter, "Introduction to current and future protein therapeutics: a protein engineering perspective," *Experimental Cell Research* 317(9): 1261-1269 (2011).
Karsan et al., "Leukocyte Adhesion Deficiency Type II Is a Generalized Defect of De Novo GDP-Fucose Biosynthesis. Endothelial Cell Fucosylation Is Not Required for Neutrophil Rolling on Human Nonlymphoid Endothelium," *Journal of Clinical Investigation* 101(11):2438-2445 (1998).
Malphettes et al., "Highly efficient deletion of FUT8 in CHO cell lines using zinc-finger nucleases yields cells that produce completely nonfucosylated antibodies," *Biotechnology and Bioengineering* 106(5): 774-783 (2010).
Ohyama et al., "Molecular Cloning and Expression of GDP-D-mannose-4,6-dehydratase, a Key Enzyme for Fucose Metabolism Defective in Lec13 Cells*," *Journal of Biological Chemistry* 273(23): 14582-14587 (1998).
Smith et al., "Conditional control of selectin ligand expression and global fucosylation events in mice with a targeted mutation at the FX locus," *Journal of Cell Biology* 158(4):801-815 (2002).

\* cited by examiner $TAF\ glycans\ (\%) = 3.354 - 1.388 * fucose\ (\frac{g}{L}) + 0.111 * glucose\ (\frac{g}{L}) + [fucose\ (\frac{g}{L}) - 0.4375] * [fucose\ (\frac{g}{L}) - 0.4375] * 1.9527$

SEQUENCE LISTING

<160> NUMBER OF SEQ ID NOS: 23

<210> SEQ ID NO 1
<211> LENGTH: 235

<212> TYPE: PRT
<213> ORGANISM: Artificial Sequence
<220> FEATURE:
<223> OTHER INFORMATION: Synthetic Polypeptide

<400> SEQUENCE: 1

Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Ile His Trp Phe Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 2
<211> LENGTH: 470
<212> TYPE: PRT
<213> ORGANISM: Artificial Sequence
<220> FEATURE:
<223> OTHER INFORMATION: Synthetic Polypeptide

<400> SEQUENCE: 2

Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

```
Thr Ala Tyr Met Gln Leu Ser Ser Leu Thr Ser Glu Asp Ser Ala Val
            100                 105                 110

Tyr Tyr Cys Ala Arg Ser Thr Tyr Gly Gly Asp Trp Tyr Phe Asn
        115                 120                 125

Val Trp Gly Ala Gly Thr Thr Val Thr Val Ser Ala Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
            210                 215                 220

Val Asn His Lys Pro Ser Asn Thr Lys Val Asp Lys Lys Ala Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 3
<211> LENGTH: 297
<212> TYPE: PRT
<213> ORGANISM: Artificial Sequence
<220> FEATURE:
```

<223> OTHER INFORMATION: Synthetic Polypeptide

<400> SEQUENCE: 3

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 4
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: LC CDR1

<400> SEQUENCE: 4

Arg Ala Ser Ser Ser Val Ser Tyr Ile His
1               5                   10

<210> SEQ ID NO 5

```
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: LC CDR2

<400> SEQUENCE: 5

Ala Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: LC CDR3

<400> SEQUENCE: 6

Gln Gln Trp Thr Ser Asn Pro Pro Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: HC CDR1

<400> SEQUENCE: 7

Ser Tyr Asn Met His
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: HC CDR2

<400> SEQUENCE: 8

Ala Ile Tyr Pro Gly Asn Gly Asp Thr Ser Tyr Asn Gln Lys Phe Lys
1               5                   10                  15

Gly

<210> SEQ ID NO 9
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: HC CDR3

<400> SEQUENCE: 9

Ser Thr Tyr Tyr Gly Gly Asp Trp Tyr Phe Asn Val
1               5                   10
```

<210> SEQ ID NO 10
<211> LENGTH: 106
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL

<400> SEQUENCE: 10

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105
```

<210> SEQ ID NO 11
<211> LENGTH: 121
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH

<400> SEQUENCE: 11

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120
```

<210> SEQ ID NO 12
<211> LENGTH: 213
<212> TYPE: PRT
<213> ORGANISM: Artificial Sequence
<220> FEATURE:
<223> OTHER INFORMATION: Synthetic Polypeptide -continued

```
<220> FEATURE:
<221> NAME/KEY: MISC_FEATURE
<223> OTHER INFORMATION: VL-IgG Kappa

<400> SEQUENCE: 12

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 13
<211> LENGTH: 451
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH-IgG1

<400> SEQUENCE: 13

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95
```

```
Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 14
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: LC CDR1
```

```
<400> SEQUENCE: 14

Gln Asp Val Asn Thr Ala
1               5

<210> SEQ ID NO 15
<211> LENGTH: 3
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: LC CDR2

<400> SEQUENCE: 15

Ser Ala Ser
1

<210> SEQ ID NO 16
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: LC CDR3

<400> SEQUENCE: 16

Gln Gln His Tyr Thr Thr Pro Pro Thr
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: HC CDR1

<400> SEQUENCE: 17

Gly Phe Asn Ile Lys Asp Thr Tyr
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: HC CDR2

<400> SEQUENCE: 18

Ile Tyr Pro Thr Asn Gly Tyr Thr
1               5

<210> SEQ ID NO 19
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
```

<223> OTHER INFORMATION: HC CDR3

<400> SEQUENCE: 19

Ser Arg Trp Gly Gly Asp Gly Phe Tyr Ala Met Asp Tyr
1               5                   10

<210> SEQ ID NO 20
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 21
<211> LENGTH: 120
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

```
<210> SEQ ID NO 22
<211> LENGTH: 214
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL-IgG Kappa

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 450
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH-IgG1

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60
```

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

TOTAL AFUCOSYLATED GLYCOFORMS OF ANTIBODIES PRODUCED IN CELL CULTURE

CROSS REFERENCE TO RELATED APPLICATIONS

This application is a national stage application under 35 U.S.C. § 371 of International Application No. PCT/US2019/024154, having an international filing date of Mar. 26, 2019; which claims the benefit under 35 U.S.C. 119(e) of U.S. Provisional Application No. 62/648,308, filed Mar. 26, 2018, all of which are incorporated by reference herein in their entireties.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 28,547 byte ASCII (Text) file named "52249A_Seqlisting.txt"; created on Mar. 26, 2019.

BACKGROUND

Glycosylation is one of the most common, yet important, post-translational modifications, as it plays a role in multiple cellular functions, including, for example, protein folding, quality control, molecular trafficking and sorting, and cell surface receptor interaction. Glycosylation affects the therapeutic efficacy of recombinant protein drugs, as it influences the bioactivity, pharmacokinetics, immunogenicity, solubility, and in vivo clearance of a therapeutic glycoprotein. Fc glycoform profiles, in particular, are important product quality attributes for recombinant antibodies, as they directly impact the clinical efficacy and pharmacokinetics of the antibodies.

The high mannose (HM) glycoform content has been found to affect pharmacokinetic properties of certain therapeutic antibodies (Goetze, et al., (2011) Glycobiology 21, 949-59; Yu, et al., (2012) MAbs 4, 475-87). HM glycoforms not only influence the serum clearance rate of the antibodies, but such glycoforms, in addition to afucosylated (afuco) glycoforms, can impact antibody effector function or antibody-mediated target cell killing, also known as antibody-dependent cellular cytotoxicity (ADCC).

Many factors influence the glycan structure and thus the ultimate glycosylated form (glycoform) of the protein (glycoprotein). For example, the cell line expressing the antibody, the cell culture medium, the feed medium composition, and the timing of the feeds during cell culture can impact the production of glycoforms of the protein.

While research groups have suggested many ways to influence the levels of particular glycoforms of an antibody, there still is a need in the biopharmaceutical industry for simple and efficient methods to manipulate and control the levels of total afucosylated (TAF) glycoforms during recombinant production of therapeutic antibodies.

SUMMARY

Described for the first time are data demonstrating that the concentration of fucose and/or glucose in a cell culture medium comprising cells producing a recombinant glycosylated protein (e.g., an antibody or antibody binding protein) influences the level of TAF glycoforms of the recombinant glycosylated protein produced. Whereas larger changes in the level of TAF glycoforms of a recombinant glycosylated protein (e.g., an antibody or antibody binding protein) can be achieved by manipulating the concentration of fucose in the cell culture medium comprising cells producing the recombinant glycosylated protein (e.g., antibody or antibody binding protein), smaller changes in the TAF glycoforms level can be achieved by altering the concentration of glucose in the cell culture medium, as described herein. Also, the data demonstrate that, while glucose concentration of the cell culture medium affects levels of high mannose glycans and afucosylated glycans, the fucose concentration of the cell culture medium affects levels of afucosylated glycans but does not influence high mannose glycan levels. The discovery that each of these sugars, differing in chemical formula by only one oxygen atom, leads to differential effects on TAF glycoform levels was unexpected. Without being bound to a particular theory, maintaining cells producing the recombinant glycosylated protein (e.g., antibody or antibody binding protein) in a cell culture medium comprising fucose and/or glucose at concentrations as taught herein allows for production of a recombinant glycosylated protein (e.g., an antibody or antibody binding protein) composition having a desired or predetermined or pre-selected level of TAF glycoforms (e.g., high mannose glycans and afucosylated glycans). Accordingly, the disclosure relates to methods of producing a recombinant glycosylated protein composition (e.g., an antibody composition or antibody binding protein composition) comprising a desired or predetermined or pre-selected level of TAF glycoforms.

The disclosure provides methods of producing a recombinant glycosylated protein composition (e.g., an antibody composition or antibody binding protein composition). In exemplary embodiments, the method comprises maintaining glycosylation-competent cells in a cell culture medium comprising fucose and/or glucose at a specific concentration as described herein, depending on the level of TAF glycoforms desired.

In exemplary embodiments, the level of TAF glycoforms in the recombinant glycosylated protein composition (e.g., antibody composition or antibody binding protein composition) is less than or about 10% and, in exemplary aspects, the method comprises maintaining glycosylation-competent cells in a cell culture medium comprising fucose, wherein fucose is present in the culture medium at a concentration between about 0.17 g/L and about 1.0 g/L.

In exemplary embodiments, the level of TAF glycoforms in the recombinant glycosylated protein composition (e.g., antibody composition or antibody binding protein composition) is less than or about 10% and, in exemplary aspects, the method comprises maintaining glycosylation-competent cells in a cell culture medium comprising fucose, wherein fucose is present in the culture medium at a concentration between about 0.1 g/L and about 1.0 g/L, and wherein the glycosylation-competent cells are not genetically modified to alter activity of an enzyme of the de novo pathway or the salvage pathway.

The disclosure also provides methods of producing a recombinant glycosylated protein composition (e.g., an antibody composition or antibody binding protein composition) comprising maintaining glycosylation-competent cells in a cell culture medium comprising fucose and glucose, wherein fucose is present in the culture medium at a concentration of about 0.1 g/L to about 1.0 g/L and adding glucose to the cell culture medium according to a glucose feeding schedule that achieves an average glucose concentration of about 10 g/L or less.

Recombinant glycosylated protein compositions (e.g., antibody compositions or antibody binding protein compositions) produced by the methods of the disclosure are provided herein. Additionally, related pharmaceutical compositions and cell culture media are provided. In exemplary aspects, the cell culture medium comprises comprising an exogenous nucleic acid encoding an antibody (e.g., an IgG antibody) and a culture medium comprising fucose at a concentration of about 0.1 g/L to about 1.0 g/L or about 0.17 g/L to about 1.0 g/L. In some instances, the glycosylation-competent cells are not genetically modified to alter activity of an enzyme of the de novo pathway or the salvage pathway. Optionally, the glycosylation-competent cells are not genetically modified to knock-out a gene encoding GDP-keto-6-deoxymannonse-3,5-epimerase, 4-reductase. The culture medium, in some aspects, further comprises glucose at a concentration less than about 10 g/L, optionally, less than about 9 g/L or about 6 g/L or less (e.g., about 0.5 g/L to about 4 g/L). In exemplary instances, the pH of the culture medium is about 6.85 to about 7.05, e.g., about 6.90 to about 7.00. In some instances, the cell culture medium does not comprise mannose. In certain aspects, the antibody is an IgG1 antibody. In exemplary aspects, the antibody is specific for a tumor-associated antigen, such as one comprising SEQ ID NO: 3.

Methods of altering or modulating the level of TAF glycans of a recombinant glycosylated protein composition (e.g., an antibody composition or antibody binding protein composition) produced by glycosylation-competent cells in a cell culture medium are further provided herein. In exemplary aspects, the method comprises (A) adding fucose to a cell culture medium comprising the glycosylation-competent cells to achieve a fucose concentration of about 0.1 g/L to about 1.0 g/L to decrease the level of TAF glycans; (B) adding glucose to a cell culture medium comprising the glycosylation-competent cells to achieve a glucose concentration less than about 10 g/L to increase the level of TAF; or (C) a combination of both (A) and (B).

Also provided are methods of modulating the level of afucosylated glycans of a recombinant glycosylated protein composition (e.g., an antibody composition or antibody binding protein composition) produced by glycosylation-competent cells. In exemplary embodiments, the method comprises (A) adding fucose to a cell culture medium comprising the glycosylation-competent cells to achieve a fucose concentration of about 0.1 g/L to about 1.0 g/L, to decrease the level of afucosylated glycans; (B) adding glucose to a cell culture medium comprising the glycosylation-competent cells to achieve a glucose concentration less than or about 10 g/L to increase the level of afucosylated glycans; or (C) a combination of both (A) and (B).

The present disclosure further provides a method of modulating the level of high mannose (HM) glycans of a recombinant glycosylated protein composition (e.g., an antibody composition or antibody binding protein composition) produced by glycosylation-competent cells. In exemplary embodiments, the method comprises adding glucose to a cell culture medium comprising the glycosylation-competent cells to achieve a glucose concentration less than about 10 g/L to increase the level of HM glycans.

Also provided by the present disclosure are methods of modulating the level of afucosylated glycans of a recombinant glycosylated protein composition (e.g., an antibody composition or antibody binding protein composition) produced by glycosylation-competent cells comprising reducing the pH of the cell culture medium by about 0.03 to about 1.2 to reduce the level of afucosylated glycans of the composition by about 0.5% to about 2% or increasing the pH of the cell culture medium by about 0.03 to about 1.2 to increase the level of afucosylated glycans of the composition by about 0.5% to about 2%.

Methods of reducing the level of afucosylated glycans of a recombinant glycosylated protein composition (e.g., an antibody composition or antibody binding protein composition) produced by glycosylation-competent cells by about 1% to about 2%, comprising reducing the pH of the cell culture medium by about 0.05 to about 1.2 are provided by the present disclosure.

Additionally provided are methods of reducing the level of afucosylated glycans of a recombinant glycosylated protein composition (e.g., an antibody composition or antibody binding protein composition) produced by glycosylation-competent cells by about 0.5% to about 1.1%, comprising reducing the pH of the cell culture medium by about 0.03-0.07.

The present disclosure further provides methods of increasing the level of afucosylated glycans of a recombinant glycosylated protein composition (e.g., an antibody composition or antibody binding protein composition) produced by glycosylation-competent cells by about 1% to about 2%, comprising increasing the pH of the cell culture medium by about 0.05 to about 1.2.

Also provided are methods of increasing the level of afucosylated glycans of a recombinant glycosylated protein composition (e.g., an antibody composition or antibody binding protein composition) produced by glycosylation-competent cells by about 0.5% to about 1.1%, comprising increasing the pH of the cell culture medium by about 0.03-0.07.

The present disclosure further provides methods of modulating the level of TAF glycans of a recombinant glycosylated protein composition (e.g., an antibody composition or antibody binding protein composition) produced by glycosylation-competent cells, comprising modulating, reducing or increasing, the level of afucosylated glycans of the composition in accordance with a presently disclosed method of modulating, reducing or increasing, the level of afucosylated glycans.

The present disclosure provides a method of producing a recombinant glycosylated protein composition (e.g., an antibody composition or antibody binding protein composition), wherein the level of afucosylated glycans in the composition is about 6.2% to about 8.4%, the method comprising maintaining glycosylation-competent cells in a cell culture medium at a pH higher than 7.05 and lower than 7.2, wherein: (A) the pH of the cell culture medium changes by less than 0.15 (optionally by less than 0.10) during the culture period or (B) the temperature of the cell culture medium changes by not more than 2 degrees C. or the method does not comprise culturing the cells in a cell culture medium comprising manganese or betaine or (D) a combination of two or three of (A), (B), and (C).

DETAILED DESCRIPTION

Many secreted proteins undergo post-translational glycosylation, a process by which sugar moieties (e.g., glycans, saccharides) are covalently attached to specific amino acids of a protein. In eukaryotic cells, two types of glycosylation reactions occur: (1) N-linked glycosylation, in which glycans are attached to the asparagine of the recognition sequence Asn-X-Thr/Ser, where "X" is any amino acid except proline, and (2) O-linked glycosylation in which glycans are attached to serine or threonine. Regardless of the glycosylation type (N-linked or O-linked), microheterogeneity of protein glycoforms exists due to the large range of glycan structures associated with each site (0 or N).

Figure 1A:
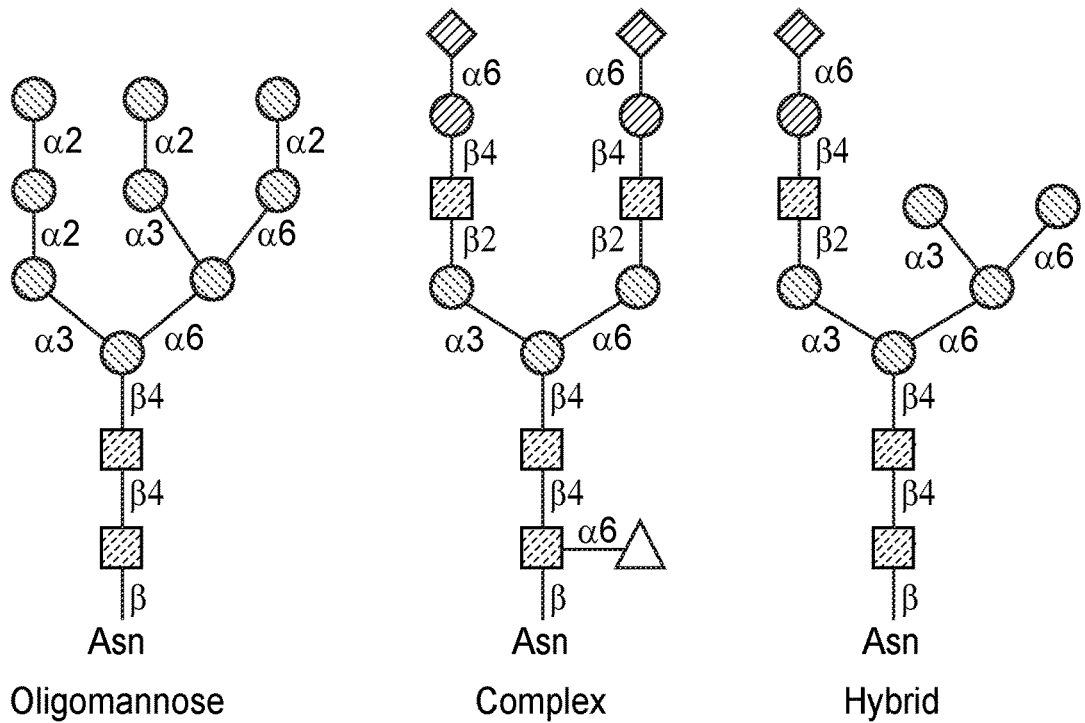
FIG. 1A is an illustration of the three types of N-glycans (oligomannose, complex and hybrid) and commonly used symbols for such saccharides.

All N-glycans have a common core sugar sequence: Man$\alpha$1-6(Man$\alpha$1-3)Man$\beta$1-4GlcNAc$\beta$1-4GlcNAc$\beta$1-Asn-X-Ser/Thr (Man$_3$GlcNAc$_2$Asn) and are categorized into one of three types: (A) a high mannose (HM) or oligomannose (OM) type, which consists of two N-acetylglucosamine (GalNAc) moieties and a large number (e.g., 5, 6, 7, 8 or 9) of mannose (Man) residues (B) a complex type, which comprises more than two GlcNAc moieties and any number of other sugar types or (C) a hybrid type, which comprises a Man residue on one side of the branch and GlcNAc at the base of a complex branch. FIG. 1A (taken from Stanley et al., Chapter 8: N-Glycans, Essentials of Glycobiology, 2$^{nd}$ ed., Cold Spring Harbor Laboratory Press; 2009) shows the three types of N-glycans.

Figure 1B:
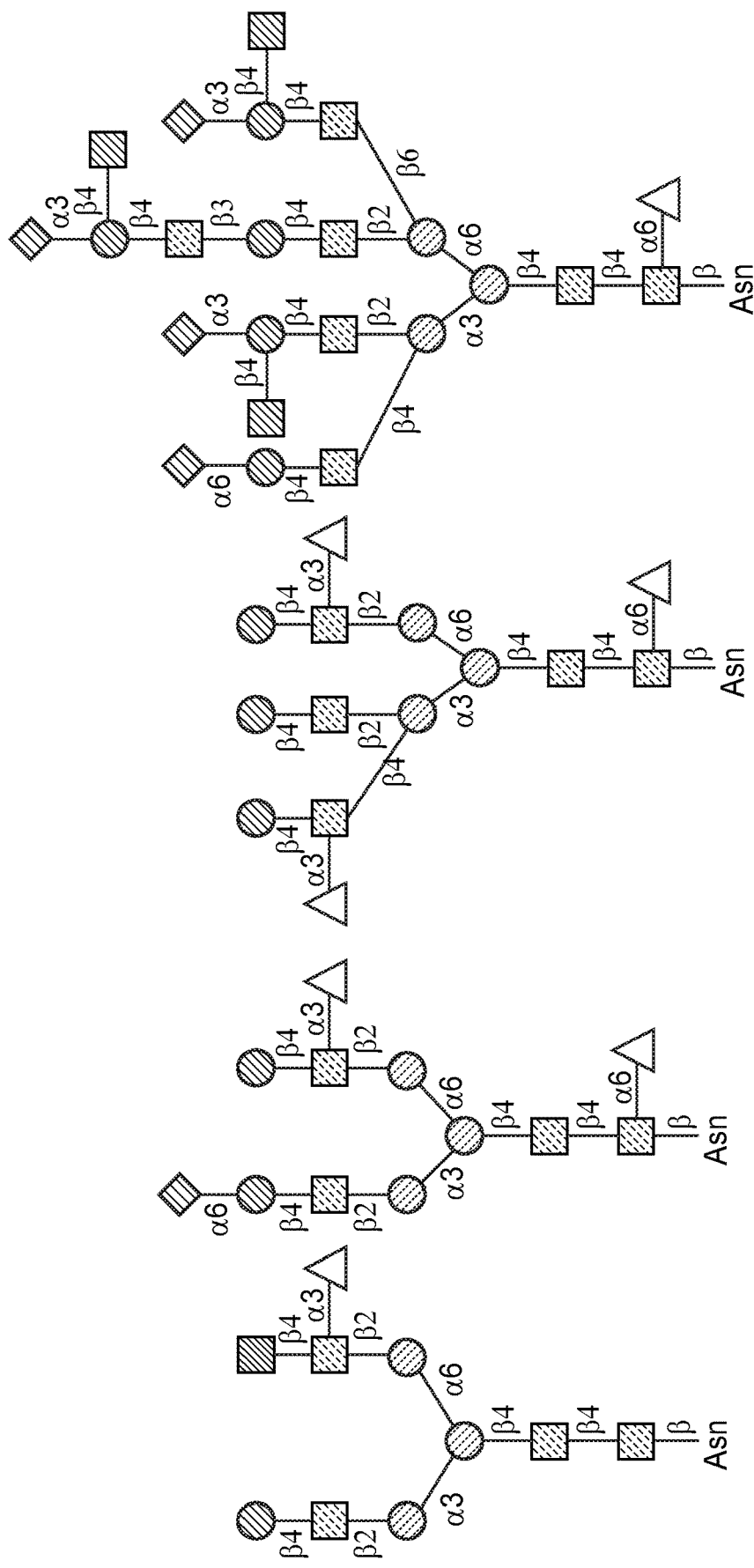
FIG. 1B is an illustration of exemplary glycan structures.

N-linked glycans typically comprise one or more monosaccharides of galactose (Gal), N-acetylgalactosamine (GalNAc), galactosamine (GalN), glucose (GLc), N-acetylglucoasamine (ClcNAc), glucoasamine (GlcN), mannose (Man), N-Acetylmannosamine (ManNAc), Mannosamine (ManN), xylose (Xyl), NOAcetylneuraminic acid (Neu5Ac), N-Glycolylneuraminic acid (Neu5Gc), 2-keto-3-doxynononic acid (Kdn), fucose (Fuc), Glucuronic acid (GLcA), Iduronic acid (IdoA), Galacturonic acid (Gal A), mannuronic acid (Man A). The commonly used symbols for such saccharides are shown in FIG. 1A. Exemplary glycans and their identity are shown in FIG. 1B.

N-linked glycosylation begins in the endoplasmic reticulum (ER), where a complex set of reactions result in the attachment of a core glycan structure made essentially of two GlcNAc residues and three Man residues. The glycan complex formed in the ER is modified by action of enzymes in the Golgi apparatus. If the saccharide is relatively inaccessible to the enzymes, it typically stays in the original HM form. If enzymes can access the saccharide, then many of the Man residues are cleaved off and the saccharide is further modified, resulting in the complex type N-glycans structure. For example, mannosidase-1 located in the cis-Golgi, can cleave or hydrolyze a HM glycan, while fucosyltransferase FUT-8, located in the medial-Golgi, fucosylates the glycan (Hanrue Imai-Nishiya (2007), BMC Biotechnology, 7:84).

Accordingly, the sugar composition and the structural configuration of a glycan structure varies, depending on the glycosylation machinery in the ER and the Golgi apparatus, the accessibility of the machinery enzymes to the glycan structure, the order of action of each enzyme and the stage at which the protein is released from the glycosylation machinery, among other factors.

The disclosure provided herein relates to methods of producing an antibody composition comprising a desired or predetermined or pre-selected level of TAF glycoforms. In exemplary embodiments, the method comprises maintaining glycosylation-competent cells in a cell culture medium comprising fucose and/or glucose at a specific concentration as described herein, depending on the level of TAF glycoforms desired. Also, the disclosure relates to method of producing an antibody composition comprising a desired or predetermined or pre-selected level of afucosylated glycoforms, e.g., the level of afucosylated glycans in the antibody composition is about 6.2% to about 8.4%. In exemplary embodiments, the method comprises maintaining glycosylation-competent cells in a cell culture medium at a pH higher than 7.05 and lower than 7.2, wherein: (A) the pH of the cell culture medium changes by less than 0.15 (optionally by less than 0.10) during the culture period or (B) the temperature of the cell culture medium changes by not more than 2 degrees C. or the method does not comprise culturing the cells in a cell culture medium comprising manganese or betaine or (D) a combination of two or three of (A), (B), and (C). Without being bound to a particular theory, it is believed that the methods of the disclosure provide a means for tailor-made compositions comprising specific amounts of particular glycoforms of a given antibody.

In exemplary embodiments, the levels of TAF glycans are modulated. As used herein, "total afucosylated glycans" or "TAF glycans" or "total afucosylated glycoforms" or "TAF glycoforms" refers to the sum amount of high mannose (HM) glycans and afucosylated glycans. In exemplary embodiments, the levels of HM glycans are modulated. As used herein, the term "high mannose glycans" or "HM glycans" or "high mannose glycoforms" or "HM glycoforms" or "HM" encompasses glycans comprising 5, 6, 7, 8, or 9 mannose residues, abbreviated as Man5, Man6, Man7, Man8, and Man9, respectively. In exemplary embodiments, the levels of afucosylated glycans are modulated. As used herein, the term "afucosylated glycan" or "afuco glycan" or "afucosylated glycoform" or "Afuc" refers to glycoforms which lack a core fucose, e.g., an α1,6-linked fucose on the GlcNAc residue involved in the amide bond with the Asn of the N-glycosylation site. Afucosylated glycoforms include, but are not limited to, A1G0, A2G0, A2G1a, A2G1b, A2G2, and A1G1M5. Additional afucosylated glycans include, e.g., A1G1a, G0[H3N4], G0[H4N4], G0[H5N4], FO-N[H3N3]. See, e.g., Reusch and Tejada, Glycobiology 25(12): 1325-1334 (2015). In exemplary aspects, the level of TAF and the amounts of HM glycoforms and afucosylated glycoforms are determined via Hydrophilic Interaction Liquid Chromatography (HILIC), as further described herein in Example 1. After enzyme cleavage of the N-glycans, HILIC is performed to obtain a chromatogram with several peaks, each peak of which represents a mean distribution (amount) of a different glycoform. For these purposes, % Peak Area=Peak Area/Total Peak Area×100%, and % Total Peak Area=Sample Total Area/Total Area of the Standard×100%. The calculations used for purposes of determining the % TAF may be carried out as follows:

% Afucosylated glycoforms=% $A1G0$+% $A2G0$+% $A2G1a$+% $A2G1b$+% $A2G2$+% $A1G1M5$.

% High mannose glycoforms=% Man5 (if detectable)+% Man6 (if detectable)+% Man7 (if detectable)+% Man8 (if detectable)+% Man9 (if detectable)

The disclosure provides methods of producing a recombinant glycosylated protein composition. In exemplary embodiments, the recombinant glycosylated protein composition is an antibody composition. In exemplary embodiments, the method comprises maintaining glycosylation-competent cells in a cell culture medium comprising fucose and/or glucose at a specific concentration as described herein, depending on the level of TAF glycoforms desired.

Fucose

In exemplary embodiments of the methods disclosed herein, fucose is present in the culture medium at a concentration from about 0.1 g/L to about 2.0 g/L, optionally, about 0.1 g/L to about 1.75 g/L, about 0.1 g/L to about 1.5 g/L, or about 0.1 g/L to about 1.2 g/L. In exemplary instances, fucose is present in the culture medium at a concentration less than or about 1.2 g/L. In exemplary instances, fucose is present in the culture medium at a concentration from about 0.1 g/L to about 1.0 g/L. In exemplary instances, the culture medium comprises fucose at a concentration from about 0.17 g/L to about 2.0 g/L, about 0.17 g/L to about 1.75 g/L, about 0.17 g/L to about 1.5 g/L, or about 0.17 g/L to about 1.2 g/L. In exemplary aspects, fucose is present in the culture medium at a concentration from about 0.17 g/L to about 1.2 g/L. In exemplary instances, fucose is present in the culture medium at a concentration from about 0.17 g/L to about 1.0 g/L. In exemplary instances, the culture medium comprises fucose at a concentration from about 0.2 g/L to about 2.0 g/L, about 0.2 g/L to about 1.75 g/L, about 0.2 g/L to about 1.5 g/L, or about 0.2 g/L to about 1.2 g/L. In exemplary instances, fucose is present in the culture medium at a concentration from about 0.2 g/L to about 1.0 g/L. In exemplary instances, fucose is present in the culture medium at a concentration less than or about 1.0 g/L. For example, in some instances, the fucose concentration of the culture medium is about 0.10 g/L, about 0.11 g/L, about 0.12 g/L, about 0.13 g/L, about 0.14 g/L, about 0.15 g/L, about 0.16 g/L, about 0.17 g/L, about 0.18 g/L, about 0.19 g/L, or about 0.20 g/L. In some instances, the fucose concentration of the culture medium is about 0.3 g/L, about 0.4 g/L, about 0.5 g/L, about 0.6 g/L, about 0.7 g/L, about 0.8 g/L, or about 0.9 g/L. In exemplary aspects, the fucose concentration is not more than or about 1.0 g/L, not more than or about 0.9 g/L, not more than or about 0.8 g/L, or not more than or about 0.7 g/L. In exemplary instances, fucose is present in the culture medium at a concentration less than or about 0.75 g/L, or about 0.25 g/L to about 0.75 g/L, e.g., about 0.4 g/L to about 0.5 g/L, or about 0.6 g/L. In exemplary aspects, fucose is present in the culture medium at a concentration of less than about 0.6 g/L, e.g., about 0.2 g/L to about 0.5 g/L.

In exemplary aspects, the method of producing a recombinant glycosylated protein composition (e.g., an antibody composition or antibody binding protein composition) comprises maintaining the glycosylation-competent cells in two different cell culture media. In exemplary aspects, the method of producing a recombinant glycosylated protein composition (e.g., an antibody composition or antibody binding protein composition) comprises maintaining the glycosylation-competent cells in a first cell culture medium for an initial time period and subsequently maintaining the glycosylation-competent cells in a second cell culture medium, optionally, wherein the first cell culture medium does not comprise fucose at a concentration of about 0.1 g/L to about 1.0 g/L and the second cell culture medium comprises fucose at a concentration of about 0.1 g/L to about 1.0 g/L and the second cell culture medium comprises fucose, e.g., at one of the above concentrations. In exemplary instances, the initial time period begins when cells are inoculated into a bioreactor comprising cell culture medium, e.g., the cell culture medium. In some aspects, the initial time period is about 1 day to about 3 days, e.g., about 24 hours to about 72 hours. In exemplary aspects, the initial time period is greater than about 3 days (about 72 hours) but less than about 10 days (about 240 hours) or less than about 156 hours. In exemplary aspects, the initial time period is about 3, about 4, about 5, about 6, about 7, about 8, or about 9 days. In exemplary aspects, the method comprises adding fucose to the culture medium after the initial time period. In some aspects, fucose is added to the first culture medium to obtain the second cell culture medium. For example, in various aspects, the method comprises adding fucose after about 1 day to about 3 days, after about 3 days but less than about 10 days, or after about 3, about 4, about 5, about 6, about 7, about 8, or about 9 days. In exemplary aspects, the method comprises adding fucose to the cell culture medium, e.g., the first cell culture medium, on the 6th day, $7^{th}$ day, $8^{th}$ day, or $9^{th}$ day post-cell culture inoculation. In exemplary aspects, fucose is added to a final concentration greater than about 0.1 g/L, greater than about 0.17 g/L, or greater than about 0.2 g/L, and less than about 2.0 g/L. In exemplary aspects, the first cell culture medium does not comprise fucose. In exemplary aspects, the first cell culture medium comprises fucose, but at a concentration that is undetectable or immeasurable, or at a concentration that is substantially below the fucose concentration of the second cell culture medium, e.g., substantially below 0.1 g/L, below about 0.17 g/L, or below about 0.2 g/L.

In alternative aspects, the methods comprising maintaining glycosylation-competent cells in a cell culture medium comprising fucose (e.g., at a concentration greater than about 0.1 g/L, greater than about 0.17 g/L, or greater than about 0.2 g/L, and less than about 2.0 g/L) for the entire duration the glycosylation-competent cells are maintained in cell culture, or for a large part of the culture period. In some aspects, the method of producing a recombinant glycosylated protein composition (e.g., an antibody composition or antibody binding protein composition) comprises inoculating the glycosylation-competent cells in a bioreactor comprising cell culture medium comprising fucose and maintaining the cells in the cell culture medium at the concentration of fucose is maintained to be substantially the same throughout the duration of the cell culture.

In exemplary embodiments, the concentration of fucose fluctuates very little during the course of cell culture. In exemplary aspects, the fucose concentration fluctuates by about 0.2 g/L or less during the time the glycosylation-competent cells are maintained in the cell culture medium comprising fucose. In exemplary aspects, the concentration of fucose fluctuates by about 0.1 g/L or less during the time the glycosylation-competent cells are maintained in the cell culture medium comprising fucose. In exemplary aspects, when fucose is added to the cell culture medium, e.g., after the initial cell culture period, fucose is added to the medium not more than once or twice during the cell culture period.

Glucose

In exemplary embodiments of the methods disclosed herein, glucose is present in the culture medium. In exemplary aspects, glucose is present in the culture medium at a concentration less than or about 10 g/L, less than or about 9.0 g/L, or less than or about 6.0 g/L. In exemplary aspects, glucose is present in the culture medium at a concentration from about 0.5 g/L to about 4.0 g/L. In exemplary aspects, glucose is present at a concentration from about X g/L to about Y g/L, wherein X is about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, or 3.9, and Y is about 0.6, 0.7, 0.8, 0.9, 1.0, 1.1, 1.2, 1.3, 1.4, 1.5, 1.6, 1.7, 1.8. 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0, provided that X is less than Y.

In exemplary aspects, the method comprises maintaining the concentration of the glucose in the cell culture medium for a time period that is equivalent to the cell culture period. In exemplary instances, maintaining the concentration of the glucose in the cell culture medium comprises sampling the cell culture medium on a regular basis, e.g., hourly, bi-hourly, once every 3, 4, 5, or 6 hours, once a day, twice a day, three times daily, or 4 times daily, and the like, measuring the glucose concentration of the sampled cell cultured medium, and adding glucose to the cell culture, if the glucose concentration of the sampled cell cultured medium is lower than the desired maintained glucose concentration. In exemplary aspects, maintaining the concentration of the glucose in the cell culture medium comprises measuring the glucose concentration of the cell culture medium via a glucose sensor. In exemplary aspects, the glucose concentration is measured via a glucose sensor at regular intervals, e.g., hourly, bi-hourly, once every 3, 4, 5, or 6 hours, once a day, twice a day, three times daily, or 4 times daily, and the like, and glucose is added to the cell culture, if the glucose concentration is determined via the glucose sensor to be lower than the desired maintained glucose concentration. In alternative aspects, the method comprises maintaining the glycosylation-competent cells in cell culture medium comprising glucose, but maintaining the concentration of the glucose in the cell culture medium only after an initial time period. In exemplary embodiments, the initial time period is about 1 day to about 3 days (about 24 hours to about 72 hours). In some instances, the initial time period is less than or about 6 days, optionally, wherein the initial time period is 3 days or 4 days or 5 days after cell culture inoculation. In exemplary aspects, the method comprises maintaining the glycosylation-competent cells in cell culture medium comprising glucose and maintaining the concentration of the glucose in the cell culture medium on the 6$^{th}$ day post-inoculation and subsequently thereafter. In exemplary aspects, the concentration of glucose is maintained for at least about 4 days or about 5 days following the initial time period, or optionally, maintaining for at least about 6 days following the initial time period.

In exemplary aspects, the cell culture medium comprises an initial glucose concentration for an initial time period. For example, in various aspects, the initial glucose concentration is about 1.0 g/L to about 15 g/L, about 1.0 to about 12 g/L, or about 1.0 g/L to about 10 g/L. The initial glucose concentration, in some aspects, is about 1.0 g/L, about 1.5 g/L, about 2.0 g/L, about 2.5 g/L, about 3.0 g/L, about 3.5 g/L, about 4.0 g/L, about 4.5 g/L, about 5.0 g/L, about 5.5 g/L, about 6.0 g/L, about 6.5 g/L, about 7.0 g/L, about 7.5 g/L, about 8.0 g/L, about 8.5 g/L, about 9.0 g/L, about 9.5 g/L, about 10.0 g/L, about 10.5 g/L, about 11.0 g/L, about 11.5 g/L, or about 12.0 g/L. In some aspects, the initial glucose concentration is about 12 g/L±1 g/L or about 9 g/L±1 g/L or about 6 g/L±1 g/L. In some aspects, the initial glucose concentration is less than about 5.0 g/L or less than about 4.0 g/L. In exemplary aspects, the initial glucose concentration is the glucose concentration of the cell culture medium used during the initial time period. In exemplary aspects, the initial glucose concentration is the glucose concentration of the cell culture medium maintained during the initial time period.

In exemplary aspects, the initial glucose concentration is the same as the glucose concentration maintained after the initial time period. In alternative aspects, the initial glucose concentration is different from the glucose concentration maintained after the initial time period. In exemplary aspects, the method comprises adding glucose to the cell culture medium after the initial time period and maintaining glucose at a different concentration relative to the initial glucose concentration. In exemplary aspects, the method comprises adding glucose to the cell culture medium after the initial time period to maintain glucose at a different concentration relative to the initial glucose concentration, wherein the step of adding glucose achieves a glucose concentration of about 10 g/L or less (e.g., about 9 g/L or less, about 6 g/L or less, about 0.5 g/L to about 4 g/L).

In exemplary aspects, the method comprises adding glucose to the cell culture medium according to a glucose feeding schedule. In some aspects, the glucose feeding schedule is initiated after the initial time period. For example, in some aspects, the initial time period is at least 3 days or 4 days and the glucose feeding schedule is initiated about 4 to about 6 days post-cell culture inoculation, e.g., about 4 days, about 5 days, about 6 days post-cell culture inoculation. In exemplary instances, the glucose feeding schedule achieves an average glucose concentration of about 10 g/L or less (e.g., about 9 g/L or less, about 6 g/L or less, about 0.5 g/L to about 4 g/L). The term "average glucose concentration" refers to the average concentrations of glucose in the cell culture medium as determined by a glucose sensor over a time period (e.g., 1 to 2 days). In exemplary instances, the glucose feeding schedule achieves an average glucose concentration based on the concentration of fucose of the cell culture medium. In some aspects, the average glucose concentration is calculated based on Formula I:

$$T=3.354-1.388F+0.111G+[F-0.4375]\times[1.9527(F-0.4375)]$$ (Formula I)

wherein T is the targeted % total afucosylated (TAF) glycans and is about 2.5% to about 6%, about 2.75% to about 5.5%, or about 3% to about 5%, F is the concentration (g/L) of fucose in the medium, and G is the average glucose concentration (g/L).

In exemplary instances, (i) the concentration of fucose is about 0.2±0.1 g/L and the average glucose concentration is about 2 to about 4 g/L; (ii) the concentration of fucose is about 0.5±0.1 g/L and the average glucose concentration is about 3 to about 6 g/L; or (iii) the concentration of fucose is about 0.75±0.1 g/L and the average glucose concentration is about 4.5 to about 9 g/L.

TAF, HM, and Afucosylated Glycan Levels

In exemplary embodiments, the methods disclosed herein produce a recombinant glycosylated protein composition (e.g., an antibody composition or antibody binding protein composition), wherein the level of TAF glycans in the composition is less than or about 10%. In exemplary aspects, the level of TAF glycans in the composition is less than or about 9%, less than or about 8%, less than or about 7%, less than or about 6%, less than or about 5%. In exemplary aspects, the level of TAF glycans in the composition is greater than or about 4%, e.g., between about 4% and about 10%. In some aspects, the level of TAF glycans in the composition is about 2% to about 6% or about 2.5% to about 5%. In some aspects, the level of TAF glycans is about 2.0%, about 2.5%, about 3.0%, about 3.5%, about 4.0%, about 4.5%, about 5%, about 5.5%, or about 6.0%. In exemplary aspects, the level of TAF glycans is about 2% to about 5% or about 2% to about 4%.

In exemplary aspects of the methods of producing a recombinant glycosylated protein composition (e.g., an antibody composition or antibody binding protein composition), fucose is present in the culture medium at a concentration between about 0.1 g/L and about 1.0 g/L, or between about 0.17 g/L and about 1.0 g/L, and the level of TAF glycans in the composition is less than about 10%.

In exemplary embodiments, the methods disclosed herein produce a recombinant glycosylated protein composition (e.g., an antibody composition or antibody binding protein composition), wherein the level of high mannose glycans in the antibody composition is less than or about 3.5%, e.g., less than or about 3.25%, less than or about 3.0%, less than or about 2.5%, less than or about 2.0%. In exemplary aspects, the level of high mannose glycans in the antibody composition is about 0.7% to about 3.0%, optionally, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0%.

In exemplary embodiments, the methods disclosed herein produce a recombinant glycosylated protein composition (e.g., an antibody composition or antibody binding protein composition), wherein the level of afucosylated glycans in the antibody composition is less than or about 3.5%, e.g., less than or about 3.25%, less than or about 3.0%, less than or about 2.5%, less than or about 2.0%. In exemplary aspects, the level of afucosylated glycans in the antibody composition is about 0.8% to about 2.8%, optionally, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, or about 2.8%.

Methods of Glycoform Measurement

Various methods are known in the art for assessing glycoforms present in a glycoprotein-containing composition or for determining, detecting or measuring a glycoform profile of a particular sample comprising glycoproteins. Suitable methods include, but are not limited to, positive ion MALDI-TOF analysis, negative ion MALDI-TOF analysis, weak anion exchange (WAX) chromatography, normal phase chromatography (NP-HPLC), exoglycosidase digestion, Bio-Gel P-4 chromatography, anion-exchange chromatography and one-dimensional n.m.r. spectroscopy, and combinations thereof. See, e.g., Mattu et al., JBC 273: 2260-2272 (1998); Field et al., Biochem J 299(Pt 1): 261-275 (1994); Yoo et al., MAbs 2(3): 320-334 (2010) Wuhrer M. et al., Journal of Chromatography B, 2005, Vol. 825, Issue 2, pages 124-133; Ruhaak L. R., Anal Bioanal Chem, 2010, Vol. 397:3457-3481 and Geoffrey, R. G. et. al. Analytical Biochemistry 1996, Vol. 240, pages 210-226. Also, the examples set forth herein describe a suitable method for assessing glycoforms present in a glycoprotein containing composition.

With regard to the disclosure, the cell culture may be maintained according to any set of conditions suitable for a recombinant glycosylated protein production. For example, in some aspects, the cell culture is maintained at a particular pH, temperature, cell density, culture volume, dissolved oxygen level, pressure, osmolality, and the like. In exemplary aspects, the cell culture prior to inoculation is shaken (e.g., at 70 rpm) at 5% $CO_2$ under standard humidified conditions in a $CO_2$ incubator. In exemplary aspects, the cell culture is inoculated with a seeding density of about $10^6$ cells/mL in 1.5 L medium.

In exemplary aspects, the methods of the disclosure comprise maintaining the glycosylation-competent cells in a cell culture medium at a pH of about 6.85 to about 7.05, e.g., in various aspects, about 6.85, about 6.86, about 6.87, about 6.88, about 6.89, about 6.90, about 6.91, about 6.92, about 6.93, about 6.94, about 6.95, about 6.96, about 6.97, about 6.98, about 6.99, about 7.00, about 7.01, about 7.02, about 7.03, about 7.04, or about 7.05. In some aspects, the cell culture medium has a pH of about 6.9 to about 7.0.

In exemplary aspects, the methods comprise maintaining the cell culture at a temperature between 30° C. and 40° C. In exemplary embodiments, the temperature is between about 32° C. to about 38° C. or between about 35° C. to about 38° C.

In exemplary aspects, the methods comprise maintaining the osmolality between about 200 mOsm/kg to about 500 mOsm/kg. In exemplary aspects, the method comprises maintaining the osmolality between about 225 mOsm/kg to about 400 mOsm/kg or about 225 mOsm/kg to about 375 mOsm/kg. In exemplary aspects, the method comprises maintaining the osmolality between about 225 mOsm/kg to about 350 mOsm/kg. In various aspects, osmolality (mOsm/kg) is maintained at about 200, 225, about 250, about 275, about 300, about 325, about 350, about 375, about 400, about 425, about 450, about 475, or about 500.

In exemplary aspects, the methods comprise maintaining dissolved the oxygen (DO) level of the cell culture at about 20% to about 60% oxygen saturation during the initial cell culture period. In exemplary instances, the method comprises maintaining DO level of the cell culture at about 30% to about 50% (e.g., about 35% to about 45%) oxygen saturation during the initial cell culture period. In exemplary instances, the method comprises maintaining DO level of the cell culture at about 20%, about 25%, about 30%, about 35%, about 40%, about 45%, about 50%, about 55%, or about 60% oxygen saturation during the initial cell culture period. In exemplary aspects, the DO level is about 35 mm Hg to about 85 mmHg or about 40 mm Hg to about 80 mmHg or about 45 mm Hg to about 75 mm Hg.

The cell culture is maintained in any one or more culture medium. In exemplary aspects, the cell culture is maintained in a medium suitable for cell growth and/or is provided with one or more feeding media according to any suitable feeding schedule. In exemplary aspects, the method comprises maintaining the cell culture in a medium comprising glucose, lactate, ammonia, glutamine, and/or glutamate. In exemplary aspects, the method comprises maintaining the cell culture in a medium comprising manganese at a concentration less than or about 1 µM during the initial cell culture period. In exemplary aspects, the method comprises maintaining the cell culture in a medium comprising about 0.25 µM to about 1 µM manganese. In exemplary aspects, the method comprises maintaining the cell culture in a medium comprising negligible amounts of manganese. In exemplary aspects, the method comprises maintaining the cell culture in a medium comprising copper at a concentration less than or about 50 ppb during the initial cell culture period. In exemplary aspects, the method comprises maintaining the cell culture in a medium comprising copper at a concentration less than or about 40 ppb during the initial cell culture period. In exemplary aspects, the method comprises maintaining the cell culture in a medium comprising copper at a concentration less than or about 30 ppb during the initial cell culture period. In exemplary aspects, the method comprises maintaining the cell culture in a medium comprising copper at a concentration less than or about 20 ppb during the initial cell culture period. In exemplary aspects, the medium comprises copper at a concentration greater than or about 5 ppb or greater than or about 10 ppb. In exemplary aspects, the cell culture medium comprises mannose. In exemplary aspects, the cell culture medium does not comprise mannose.

In exemplary embodiments, the type of cell culture is a fed-batch culture or a continuous perfusion culture. However, the methods of the disclosure are advantageously not limited to any particular type of cell culture.

Cells

The disclosure relates to methods of producing a recombinant glycosylated protein composition (e.g., an antibody composition or antibody binding protein composition) comprising maintaining glycosylation-competent cells in a cell culture medium. In exemplary aspects, the glycosylation-competent cells are eukaryotic cells, including, but not limited to, yeast cells, filamentous fungi cells, protozoa cells, algae cells, insect cells, or mammalian cells. Such host cells are described in the art. See, e.g., Frenzel, et al., *Front Immunol* 4: 217 (2013). In exemplary aspects, the eukaryotic cells are mammalian cells. In exemplary aspects, the mammalian cells are non-human mammalian cells. In some aspects, the cells are Chinese Hamster Ovary (CHO) cells and derivatives thereof (e.g., CHO-K1, CHO pro-3), mouse myeloma cells (e.g., NS0, GS-NS0, Sp2/0), cells engineered to be deficient in dihydrofolatereductase (DHFR) activity (e.g., DUKX-X11, DG44), human embryonic kidney 293 (HEK293) cells or derivatives thereof (e.g., HEK293T, HEK293-EBNA), green African monkey kidney cells (e.g., COS cells, VERO cells), human cervical cancer cells (e.g., HeLa), human bone osteosarcoma epithelial cells U2-OS, adenocarcinomic human alveolar basal epithelial cells A549, human fibrosarcoma cells HT1080, mouse brain tumor cells CAD, embryonic carcinoma cells P19, mouse embryo fibroblast cells NIH 3T3, mouse fibroblast cells L929, mouse neuroblastoma cells N2a, human breast cancer cells MCF-7, retinoblastoma cells Y79, human retinoblastoma cells SO-Rb50, human liver cancer cells Hep G2, mouse B myeloma cells J558L, or baby hamster kidney (BHK) cells (Gaillet et al. 2007; Khan, Adv Pharm Bull 3(2): 257-263 (2013)).

Cells that are not glycosylation-competent can also be transformed into glycosylation-competent cells, e.g. by transfecting them with genes encoding relevant enzymes necessary for glycosylation. Exemplary enzymes include but are not limited to oligosaccharyltransferases, glycosidases, glucosidase I, glucosidease II, calnexin/calreticulin, glycosyltransferases, mannosidases, GlcNAc transferases, galactosyltransferases, and sialyltransferases.

Figure 2:
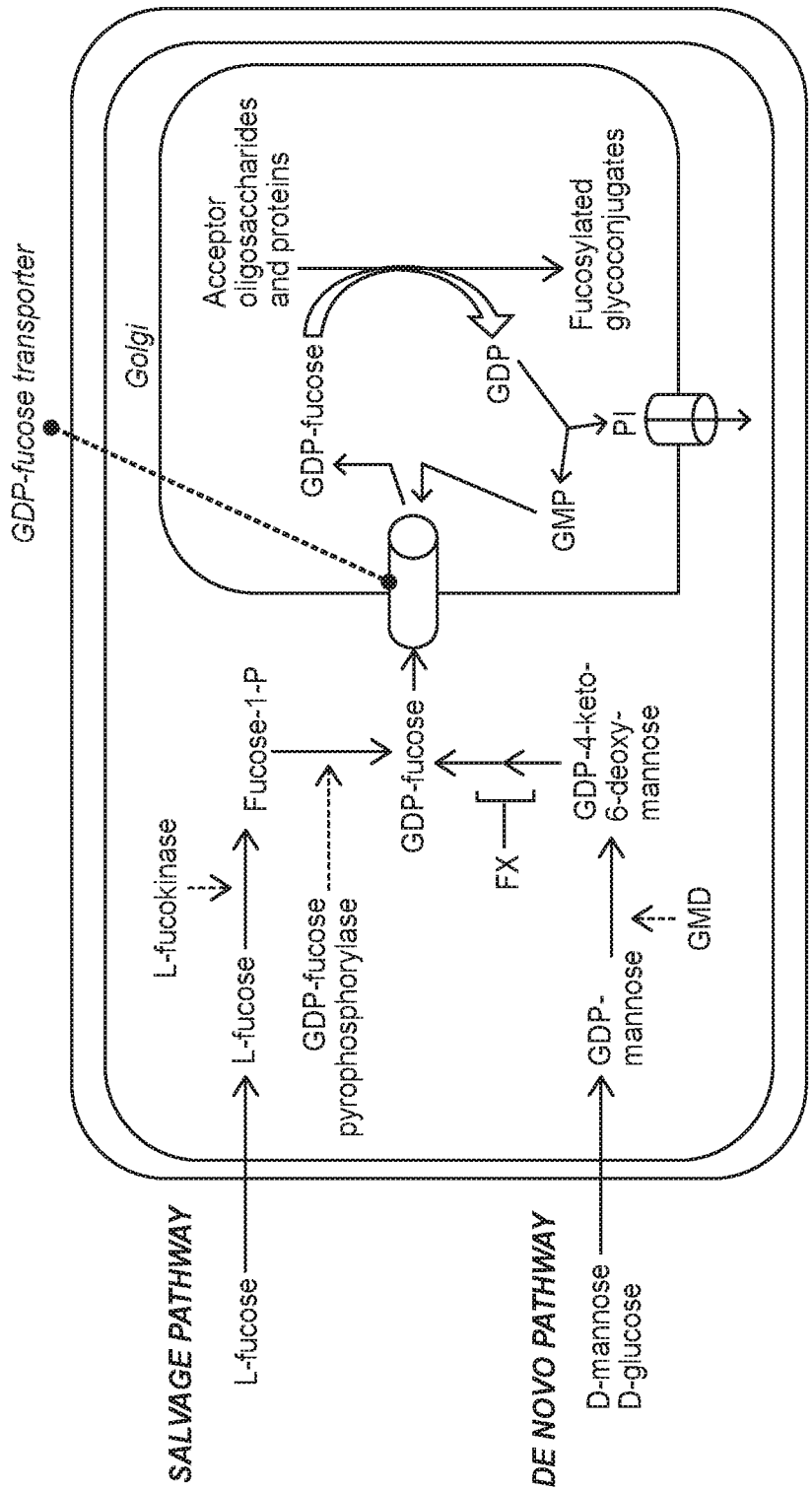
FIG. 2 is a diagram of the salvage pathway and the de novo pathway of fucose metabolism. In the salvage pathway, free L-fucose is converted to GDP-fucose, while in the de novo pathway, GDP-fucose is synthesized via three reactions catalyzed by GMD and FX. GDP-fucose is then transported from the cytosol to the Golgi lumen by GDP-Fuc Transferase and transferred to acceptor oligosaccharides and proteins. The other reaction product, GDP, is converted by a luminal nucleotide diphosphatase to guanosine 5-monophosphate (GMP) and inorganic phosphate (Pi). The former is exported to the cytosol (via an antiport system that is coupled with the transport of GDP-fucose), whereas the latter is postulated to leave the Golgi lumen via the Golgi anion channel, GOLAC. See, e.g., Nordeen et al. 2000; Hirschberg et al. 2001.

In exemplary embodiments, the glycosylation-competent cells are not genetically modified to alter the activity of an enzyme of the de novo pathway or the salvage pathway. These two pathways of fucose metabolism are shown in FIG. 2. In exemplary embodiments, the glycosylation-competent cells are not genetically modified to alter the activity of any one or more of: a fucosyl-transferase (FUT, e.g., FUT1, FUT2, FUT3, FUT4, FUT5, FUT6, FUT7, FUT8, FUT9), a fucose kinase, a GDP-fucose pyrophosphorylase, GDP-D-mannose-4,6-dehydratase (GMD), and GDP-keto-6-deoxymannose-3,5-epimerase, 4-reductase (FX). In exemplary embodiments, the glycosylation-competent cells are not genetically modified to knock-out a gene encoding FX.

In exemplary embodiments, the glycosylation-competent cells are not genetically modified to alter the activity β(1, 4)-N-acetylglucosaminyltransferase III (GNTIII) or GDP-6-deoxy-D-lyxo-4-hexulose reductase (RMD). In exemplary aspects, the glycosylation-competent cells are not genetically modified to overexpress GNTIII or RMD.

Recombinant Glycosylated Proteins

In exemplary embodiments, the recombinant glycosylated protein comprises an amino acid sequence comprising one or more N-glycosylation consensus sequences of the formula:

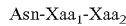

wherein $Xaa_1$ is any amino acid except Pro, and $Xaa_2$ is Ser or Thr.

In exemplary embodiments, the recombinant glycosylated protein comprises a fragment crystallizable (Fc) polypeptide. The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns. In exemplary embodiments, the recombinant glycosylated protein comprises the Fc of an IgG, e.g., a human IgG. In exemplary aspects, the recombinant glycosylated protein comprises the Fc an IgG1 or IgG2. In exemplary aspects, the recombinant glycosylated protein is an antibody, an antibody protein product, a peptibody, or a Fc-fusion protein.

In exemplary aspects, the recombinant glycosylated protein is an antibody. As used herein, the term "antibody" refers to a protein having a conventional immunoglobulin format, comprising heavy and light chains, and comprising variable and constant regions. For example, an antibody may be an IgG which is a "Y-shaped" structure of two identical pairs of polypeptide chains, each pair having one "light" (typically having a molecular weight of about 25 kDa) and one "heavy" chain (typically having a molecular weight of about 50-70 kDa). An antibody has a variable region and a constant region. In IgG formats, the variable region is generally about 100-110 or more amino acids, comprises three complementarity determining regions (CDRs), is primarily responsible for antigen recognition, and substantially varies among other antibodies that bind to different antigens. See, e.g., Janeway et al., "Structure of the Antibody Molecule and the Immunoglobulin Genes", Immunobiology: The Immune System in Health and Disease, $4^{th}$ ed. Elsevier Science Ltd./Garland Publishing, (1999).

Briefly, in an antibody scaffold, the CDRs are embedded within a framework in the heavy and light chain variable region where they constitute the regions largely responsible for antigen binding and recognition. A variable region comprises at least three heavy or light chain CDRs (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991; see also Chothia and Lesk, 1987, supra).

Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Embodiments of the disclosure include all such classes or isotypes of antibodies. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. Accordingly, in exemplary embodiments, the antibody is an antibody of isotype IgA, IgD, IgE, IgG, or IgM, including any one of IgG1, IgG2, IgG3 or IgG4.

In various aspects, the antibody can be a monoclonal antibody or a polyclonal antibody. In some aspects, the antibody comprises a sequence that is substantially similar to a naturally-occurring antibody produced by a mammal, e.g., mouse, rat, rabbit, goat, horse, chicken, hamster, pig, human, and the like. In this regard, the antibody may be considered as a mammalian antibody, e.g., a mouse antibody, rat antibody, rabbit antibody, goat antibody, horse antibody, chicken antibody, hamster antibody, pig antibody, human antibody, and the like. In certain aspects, the recombinant glycosylated protein is a monoclonal human antibody. In certain aspects, the recombinant glycosylated protein is a chimeric antibody or a humanized antibody. The term "chimeric antibody" is used herein to refer to an antibody containing constant domains from one species and the variable domains from a second, or more generally, containing stretches of amino acid sequence from at least two species. The term "humanized" when used in relation to antibodies refers to antibodies having at least CDR regions from a non-human source which are engineered to have a structure and immunological function more similar to true human antibodies than the original source antibodies. For example, humanizing can involve grafting CDR from a non-human antibody, such as a mouse antibody, into a human antibody. Humanizing also can involve select amino acid substitutions to make a non-human sequence look more like a human sequence.

An antibody, in various aspects, is cleaved into fragments by enzymes, such as, e.g., papain and pepsin. Papain cleaves an antibody to produce two Fab fragments and a single Fc fragment. Pepsin cleaves an antibody to produce a F(ab')$_2$ fragment and a pFc' fragment. In exemplary aspects, the recombinant glycosylated protein is an antibody fragment, e.g., a Fab, Fc, F(ab')$_2$, or a pFc', that retains at least one glycosylation site. With regard to the methods of the disclosure, the antibody may lack certain portions of an antibody, and may be an antibody fragment. In various aspects, the antibody fragment comprises a glycosylation site. In some aspects, the fragment is a "Glycosylated Fc Fragment" which comprises at least a portion of the Fc region of an antibody which is glycosylated post-translationally in eukaryotic cells.

The architecture of antibodies has been exploited to create a growing range of alternative antibody formats that spans a molecular-weight range of at least or about 12-150 kDa and a valency (n) range from monomeric (n=1), dimeric (n=2) and trimeric (n=3) to tetrameric (n=4) and potentially higher; such alternative antibody formats are referred to herein as "antibody protein products" or "antibody binding proteins".

Antibody protein products can be an antigen binding format based on antibody fragments, e.g., scFvs, Fabs and VHH/VH, which retain full antigen-binding capacity. The smallest antigen-binding fragment that retains its complete antigen binding site is the Fv fragment, which consists entirely of variable (V) regions. A soluble, flexible amino acid peptide linker is used to connect the V regions to a scFv (single chain fragment variable) fragment for stabilization of the molecule, or the constant (C) domains are added to the V regions to generate a Fab fragment [fragment, antigen-binding]. Both scFv and Fab are widely used fragments that can be easily produced in prokaryotic hosts. Other antibody protein products include disulfide-bond stabilized scFv (ds-scFv), single chain Fab (scFab), as well as di- and multimeric antibody formats like dia-, tria- and tetra-bodies, or minibodies (miniAbs) that comprise different formats consisting of scFvs linked to oligomerization domains. The smallest fragments are VHH/VH of camelid heavy chain Abs as well as single domain Abs (sdAb). The building block that is most frequently used to create novel antibody formats is the single-chain variable (V)-domain antibody fragment (scFv), which comprises V domains from the heavy and light chain (VH and VL domain) linked by a peptide linker of ~15 amino acid residues. A peptibody or peptide-Fc fusion is yet another antibody protein product. The structure of a peptibody consists of a biologically active peptide grafted onto an Fc domain. Peptibodies are well-described in the art. See, e.g., Shimamoto et al., mAbs 4(5): 586-591 (2012).

Other antibody protein products include a single chain antibody (SCA); a diabody; a triabody; a tetrabody; bispecific or trispecific antibodies, and the like. Bispecific antibodies can be divided into five major classes: BsIgG, appended IgG, BsAb fragments, bispecific fusion proteins and BsAb conjugates. See, e.g., Spiess et al., Molecular Immunology 67(2) Part A: 97-106 (2015).

In exemplary aspects, the recombinant glycosylated protein comprises any one of these antibody protein products (e.g., scFv, Fab VHH/VH, Fv fragment, ds-scFv, scFab, dimeric antibody, multimeric antibody (e.g., a diabody, triabody, tetrabody), miniAb, peptibody VHH/VH of camelid heavy chain antibody, sdAb, diabody; a triabody; a tetrabody; a bispecific or trispecific antibody, BsIgG, appended IgG, BsAb fragment, bispecific fusion protein, and BsAb conjugate) and comprises one or more N-glycosylation consensus sequences, optionally, one or more Fc polypeptides. In various aspects, the antibody protein product comprises a glycosylation site. In exemplary aspects, an antibody protein product can be a Glycosylated Fc Fragment conjugated to an antibody binding fragment ("Glycosylated Fc Fragment antibody product").

The recombinant glycosylated protein may be an antibody protein product in monomeric form, or polymeric, oligomeric, or multimeric form. In certain embodiments in which the antibody comprises two or more distinct antigen binding regions fragments, the antibody is considered bispecific, trispecific, or multi-specific, or bivalent, trivalent, or multivalent, depending on the number of distinct epitopes that are recognized and bound by the antibody.

Advantageously, the methods are not limited to the antigen-specificity of the antibody. Accordingly, the antibody has any binding specificity for virtually any antigen. In exemplary aspects, the antibody binds to a hormone, growth factor, cytokine, a cell-surface receptor, or any ligand thereof. In exemplary aspects, the antibody binds to a protein expressed on the cell surface of an immune cell. In exemplary aspects, the antibody binds to a cluster of differentiation molecule selected from the group consisting of: CD1a, CD1b, CD1c, CD1d, CD2, CD3, CD4, CD5, CD6, CD7, CD8, CD9, CD10, CD11A, CD11B, CD11C, CDw12, CD13, CD14, CD15, CD15s, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD45, CD45RO, CD45RA, CD45RB, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD66a, CD66b, CD66c, CD66d, CD66e, CD66f, CD68, CD69, CD70, CD71, CD72, CD73, CD74, CD75, CD76, CD79a, CD7913, CD80, CD81, CD82, CD83, CDw84, CD85, CD86, CD87, CD88, CD89, CD90, CD91, CDw92, CD93, CD94, CD95, CD96, CD97, CD98, CD99, CD100, CD101, CD102, CD103, CD104, CD105, CD106, CD107a, CD107b, CDw108, CD109, CD114, CD 115, CD116, CD117, CD118, CD119, CD120a, CD120b, CD121a, CDw121b, CD122, CD123, CD124, CD125, CD126, CD127, CDw128, CD129, CD130, CDw131, CD132, CD134, CD135, CDw136, CDw137, CD138, CD139, CD140a, CD140b, CD141, CD142, CD143, CD144, CD145, CD146, CD147, CD148, CD150, CD151, CD152, CD153, CD154, CD155, CD156, CD157, CD158a, CD158b, CD161, CD162, CD163, CD164, CD165, CD166, and CD182.

In exemplary aspects, the antibody is one of those described in U.S. Pat. No. 7,947,809 and U.S. Patent Application Publication No. 20090041784 (glucagon receptor), U.S. Pat. Nos. 7,939,070, 7,833,527, 7,767,206, and 7,786,284 (IL-17 receptor A), U.S. Pat. Nos. 7,872,106 and 7,592,429 (Sclerostin), U.S. Pat. Nos. 7,871,611, 7,815,907, 7,037,498, 7,700,742, and U.S. Patent Application Publication No. 20100255538 (IGF-1 receptor), U.S. Pat. No. 7,868,140 (B7RP1), U.S. Pat. No. 7,807,159 and U.S. Patent Application Publication No. 20110091455 (myostatin), U.S. Pat. Nos. 7,736,644, 7,628,986, 7,524,496, and U.S. Patent Application Publication No. 20100111979 (deletion mutants of epidermal growth factor receptor), U.S. Pat. No. 7,728, 110 (SARS coronavirus), U.S. Pat. No. 7,718,776 and U.S. Patent Application Publication No. 20100209435 (OPGL), U.S. Pat. Nos. 7,658,924 and 7,521,053 (Angiopoietin-2), U.S. Pat. Nos. 7,601,818, 7,795,413, U.S. Patent Application Publication No. 20090155274, U.S. Patent Application Publication No. 20110040076 (NGF), U.S. Pat. No. 7,579,186 (TGF-β type II receptor), U.S. Pat. No. 7,541,438 (connective tissue growth factor), U.S. Pat. No. 7,438,910 (IL1-R1), U.S. Pat. No. 7,423,128 (properdin), U.S. Pat. Nos. 7,411,057, 7,824,679, 7,109,003, 6,682,736, 7,132,281, and 7,807,797 (CTLA-4), U.S. Pat. Nos. 7,084,257, 7,790,859, 7,335,743, 7,084,257, and U.S. Patent Application Publication No. 20110045537 (interferon-gamma), U.S. Pat. No. 7,932,372 (MAdCAM), U.S. Pat. No. 7,906,625, U.S. Patent Application Publication No. 20080292639, and U.S. Patent Application Publicaiton No. 20110044986 (amyloid), U.S. Pat. Nos. 7,815,907 and 7,700,742 (insulin-like growth factor I), U.S. Pat. Nos. 7,566,772 and 7,964,193 (interleukin-1β), U.S. Pat. Nos. 7,563,442, 7,288,251, 7,338,660, 7,626,012, 7,618,633, and U.S. Patent Application Publication No. 20100098694 (CD40), U.S. Pat. No. 7,498,420 (c-Met), U.S. Pat. Nos. 7,326,414, 7,592,430, and 7,728,113 (M-CSF), U.S. Pat. Nos. 6,924,360, 7,067,131, and 7,090,844 (MUC18), U.S. Pat. Nos. 6,235,883, 7,807,798, and U.S. Patent Application Publication No. 20100305307 (epidermal growth factor receptor), U.S. Pat. Nos. 6,716,587, 7,872,113, 7,465,450, 7,186,809, 7,317,090, and 7,638,606 (interleukin-4 receptor), U.S. Patent Application Publication No. 20110135657 (BETA-KLOTHO), U.S. Pat. Nos. 7,887,799 and 7,879,323 (fibroblast growth factor-like polypeptides), U.S. Pat. No. 7,867,494 (IgE), U.S. Patent Application Publication No. 20100254975 (ALPHA-4 BETA-7), U.S. Patent Application Publication No. 20100197005 and U.S. Pat. No. 7,537,762 (ACTIVIN RECEPTOR-LIKE KINASE-1), U.S. Pat. No. 7,585,500 and U.S. Patent Application Publication No. 20100047253 (IL-13), U.S. Patent Application Publication No. 20090263383 and U.S. Pat. No. 7,449,555 (CD148), U.S. Patent Application Publication No. 20090234106 (ACTIVIN A), U.S. Patent Application Publication No. 20090226447 (angiopoietin-1 and angiopoietin-2), U.S. Patent Application Publication No. 20090191212 (Angiopoietin-2), U.S. Patent Application Publicaiton No. 20090155164 (C-FMS), U.S. Pat. No. 7,537,762 (activin receptor-like kinase-1), U.S. Pat. No. 7,371,381 (galanin), U.S. Patent Application Publication No. 20070196376 (INSULIN-LIKE GROWTH FACTORS), U.S. Pat. Nos. 7,267,960 and 7,741,115 (LDCAM), U.S. Pat. No. 7,265,212 (CD45RB), U.S. Pat. No. 7,709,611, U.S. Patent Application Publication No. 20060127393 and U.S. Patent Application Publication No. 20100040619 (DKK1), U.S. Pat. No. 7,807,795, U.S. Patent Application Publication No. 20030103978 and U.S. Pat. No. 7,923,008 (osteoprotegerin), U.S. Patent Application Publication No. 20090208489 (OV064), U.S. Patent Application Publication No. 20080286284 (PSMA), U.S. Pat. No. 7,888,482, U.S. Patent Application Publication No. 20110165171, and U.S. Patent Application Publication No. 20110059063 (PAR2), U.S. Patent Application Publication No. 20110150888 (HEPCIDIN), U.S. Pat. No. 7,939,640 (B7L-1), U.S. Pat. No. 7,915,391 (c-Kit), U.S. Pat. Nos. 7,807,796, 7,193,058, and 7,427,669 (ULBP), U.S. Pat. Nos. 7,786,271, 7,304,144, and U.S. Patent Application Publication No. 20090238823 (TSLP), U.S. Pat. No. 7,767,793 (SIGIRR), U.S. Pat. No. 7,705,130 (HER-3), U.S. Pat. No. 7,704,501 (ataxin-1-like polypeptide), U.S. Pat. Nos. 7,695,948 and 7,199,224 (TNF-α converting enzyme), U.S. Patent Application Publication No. 20090234106 (ACTIVIN A), U.S. Patent Application Publication No. 20090214559 and U.S. Pat. No. 7,438,910 (IL1-R1), U.S. Pat. No. 7,579,186 (TGF-β type II receptor), U.S. Pat. No. 7,569,387 (TNF receptor-like molecules), U.S. Pat. No. 7,541,438, (connective tissue growth factor), U.S. Pat. No. 7,521,048 (TRAIL receptor-2), U.S. Pat. Nos. 6,319,499, 7,081,523, and U.S. Patent Application Publication No. 20080182976 (erythropoietin receptor), U.S. Patent Application Publication No. 20080166352 and U.S. Pat. No. 7,435,796 (B7RP1), U.S. Pat. No. 7,423,128 (properdin), U.S. Pat. Nos. 7,422,742 and 7,141,653 (interleukin-5), U.S. Pat. Nos. 6,740,522 and 7,411,050 (RANKL), U.S. Pat. No. 7,378,091 (carbonic anhydrase IX (CA IX) tumor antigen), U.S. Pat. Nos. 7,318,925 and 7,288,253 (parathyroid hormone), U.S. Pat. No. 7,285,269 (TNF), U.S. Pat. Nos. 6,692,740 and 7,270,817 (ACPL), U.S. Pat. No. 7,202,343 (monocyte chemoattractant protein-1), U.S. Pat. No. 7,144,731 (SCF), U.S. Pat. Nos. 6,355,779 and 7,138,500 (4-1BB), U.S. Pat. No. 7,135,174 (PDGFD), U.S. Pat. Nos. 6,630,143 and 7,045,128 (Flt-3 ligand), U.S. Pat. No. 6,849,450 (metalloproteinase inhibitor), U.S. Pat. No. 6,596,852 (LERK-5), U.S. Pat. No. 6,232,447 (LERK-6), U.S. Pat. No. 6,500,429 (brain-derived neurotrophic factor), U.S. Pat. No. 6,184,359 (epithelium-derived T-cell factor), U.S. Pat. No. 6,143,874 (neurotrophic factor NNT-1), U.S. Patent Application Publication No. 20110027287 (PROPROTEIN CONVERTASE SUBTILISIN KEXIN TYPE 9 (PCSK9)), U.S. Patent Application Publication No. 20110014201 (IL-18 RECEPTOR), and U.S. Patent Application Publication No. 20090155164 (C-FMS). The above patents and published patent applications are incorporated herein by reference in their entirety for purposes of their disclosure of variable domain polypeptides, variable domain encoding nucleic acids, host cells, vectors, methods of making polypeptides encoding said variable domains, pharmaceutical compositions, and methods of treating diseases associated with the respective target of the variable domain-containing antigen binding protein or antibody.

In exemplary embodiments, the antibody is one of Muromonab-CD3 (product marketed with the brand name Orthoclone Okt3®), Abciximab (product marketed with the brand name Reopro®.), Rituximab (product marketed with the brand name MabThera®, Rituxan®), Basiliximab (product marketed with the brand name Simulect®), Daclizumab (product marketed with the brand name Zenapax®), Palivizumab (product marketed with the brand name Synagis®), Infliximab (product marketed with the brand name Remicade®), Trastuzumab (product marketed with the brand name Herceptin®), Alemtuzumab (product marketed with the brand name MabCampath®, Campath-1H®), Adalimumab (product marketed with the brand name Humira®), Tositumomab-I131 (product marketed with the brand name Bexxar®), Efalizumab (product marketed with the brand name Raptiva®), Cetuximab (product marketed with the brand name Erbitux®), l'Ibritumomab tiuxetan (product marketed with the brand name Zevalin®), l'Omalizumab (product marketed with the brand name Xolair®), Bevacizumab (product marketed with the brand name Avastin®), Natalizumab (product marketed with the brand name Tysabri®), Ranibizumab (product marketed with the brand name Lucentis®), Panitumumab (product marketed with the brand name Vectibix®), l'Eculizumab (product marketed with the brand name Soliris®), Certolizumab pegol (product marketed with the brand name Cimzia®), Golimumab (product marketed with the brand name Simponi®), Canakinumab (product marketed with the brand name Ilaris®), Catumaxomab (product marketed with the brand name Removab®), Ustekinumab (product marketed with the brand name Stelara®), Tocilizumab (product marketed with the brand name RoActemra®, Actemra®), Ofatumumab (product marketed with the brand name Arzerra®), Denosumab (product marketed with the brand name Prolia®), Belimumab (product marketed with the brand name Benlysta®), Raxibacumab, Ipilimumab (product marketed with the brand name Yervoy®), and Pertuzumab (product marketed with the brand name Perjeta®). In exemplary embodiments, the antibody is one of anti-TNF alpha antibodies such as adalimumab, infliximab, etanercept, golimumab, and certolizumab pegol; anti-IL1.beta. antibodies such as canakinumab; anti-IL12/23 (p40) antibodies such as ustekinumab and briakinumab; and anti-IL2R antibodies, such as daclizumab. In exemplary aspects, the antibody binds to a tumor associated antigen and is an anti-cancer antibody. Examples of suitable anti-cancer antibodies include, but are not limited to, anti-BAFF antibodies such as belimumab; anti-CD20 antibodies such as rituximab; anti-CD22 antibodies such as epratuzumab; anti-CD25 antibodies such as daclizumab; anti-CD30 antibodies such as iratumumab, anti-CD33 antibodies such as gemtuzumab, anti-CD52 antibodies such as alemtuzumab; anti-CD152 antibodies such as ipilimumab; anti-EGFR antibodies such as cetuximab; anti-HER2 antibodies such as trastuzumab and pertuzumab; anti-IL6 antibodies, such as siltuximab; and anti-VEGF antibodies such as bevacizumab; anti-IL6 receptor antibodies such as tocilizumab. In exemplary aspects, the tumor associated antigen is CD20 and the antibody is an anti-CD20 antibody. In exemplary aspects, the tumor associated antigen comprises SEQ ID NO: 3. In exemplary instances, the antibody comprises an amino acid sequence of SEQ ID NO: 1 and an amino acid sequence of SEQ ID NO: 2. In exemplary aspects, the antibody is an anti-CD20 antibody, e.g., an anti-CD20 monoclonal antibody. In alternative aspects, the IgG1 antibody is rituximab, or a biosimilar thereof. The term rituximab refers to an IgG1 kappa chimeric murine/human, monoclonal antibody that binds CD20 antigen (see CAS Number: 174722-31-7; DrugBank—DB00073; Kyoto Encyclopedia of Genes and Genomes (KEGG) entry D02994). In exemplary aspects, the antibody comprises a light chain comprising a CDR1, CDR2, and CDR3 as set forth in Table A. In exemplary aspects, the antibody comprises a heavy chain comprising a CDR1, CDR2, and CDR3 as set forth in Table A. In various instances, the antibody comprises the VH and VL or comprising VH-IgG1 and VL-IgG kappa sequences recited in Table A.

TABLE A

Rituximab Amino Acid Sequences

| Description | Sequence | SEQ ID NO: |
|---|---|---|
| LC CDR1 | RASSSVSYIH | 4 |
| LC CDR2 | ATSNLAS | 5 |
| LC CDR3 | QQWTSNPPT | 6 |
| HC CDR1 | SYNMH | 7 |
| HC CDR2 | AIYPGNGDTSYNQKFKG | 8 |
| HC CDR3 | STYYGGDWYFNV | 9 |

TABLE A -continued

Rituximab Amino Acid Sequences

| Description | Sequence | SEQ ID NO: |
|---|---|---|
| VL | QIVLSQSPAILSASPGEKVTMTC RASSSVSYIHWFQQKPGSSPKPW IYATSNLASGVPVRFSGSGSGTS YSLTISRVEAEDAATYYCQQWTS NPPTFQGGTKLEIK | 10 |
| VH | QVQLQQPGAELVKPGASVKMSCK ASGYTFTSYNMHWVKQTPGRGLE WIGAIYPGNGDTSYNQKFKGKAT LTADKSSSTAYMQLSSLTSEDSA VYYCARSTYYGGDWYFNVWGAGT TVTVSA | 11 |
| VL-IgG Kappa | QIVLSQSPAILSASPGEKVTMTC RASSSVSYIHWFQQKPGSSPKPW IYATSNLASGVPVRFSGSGSGTS YSLTISRVEAEDAATYYCQQWTS NPPTFGGGTKLEIKRTVAAPSVF IFPPSDEQLKSGTASVVCLLNNF YPREAKVQWKVDNALQSGNSQES VTEQDSKDSTYSLSSTLTLSKAD YEKHKVYACEVTHQGLSSPVTKS FNRGEC | 12 |
| VH-IgG1 | QVQLQQPGAELVKPGASVKMSCK ASGYTFTSYNMHWVKQTPGRGLE WIGAIYPGNGDTSYNQKFKGKAT LTADKSSSTAYMQLSSLTSEDSA VYYCARSTYYGGDWYFNVWGAGT TVTVSAASTKGPSVFPLAPSSKS TSGGTAALGCLVKDYFPEPVTVS WNSGALTSGVHTFPAVLQSSGLY SLSSVVTVPSSSLGTQTYICNVN HKPSNTKVDKKAEPKSCDKTHTC PPCPAPELLGGPSVFLFPPKPKD TLMISRTPEVTCVVVDVSHEDPE VKFNWYVDGVEVHNAKTKPREEQ YNSTYRVVSVLTVLHQDWLNGKE YKCKVSNKALPAPIEKTISKAKG QPREPQVYTLPPSRDELTKNQVS LTCLVKGFYPSDIAVEWESNGQP ENNYKTTPPVLDSDGSFFLYSKL TVDKSRWQGGNVFSCSVMHEALH NHYTQKSLSLSPGK | 13 |

LC, light chain;
HC, heavy chain;
VL, variable light chain;
VH, variable heavy chain.

In exemplary aspects, the antibody is an anti-EGFR antibody, e.g., an anti-HER2 monoclonal antibody. In exemplary aspects, the antibody is trastuzumab, or a biosimilar thereof. The term trastuzumab refers to an IgG1 kappa humanized, monoclonal antibody that binds HER2/neu antigen (see CAS Number: 180288-69-1; DrugBank—DB00072; Kyoto Encyclopedia of Genes and Genomes (KEGG) entry D03257). In exemplary aspects, the antibody comprises a light chain comprising a CDR1, CDR2, and CDR3 as set forth in Table B. In exemplary aspects, the antibody comprises a heavy chain comprising a CDR1, CDR2, and CDR3 as set forth in Table B. In various instances, the antibody comprises the VH and VL or comprising VH-IgG1 and VL-IgG kappa sequences recited in Table B.

TABLE B

Trastuzumab Amino Acid Sequences

| Description | Sequence | SEQ ID NO: |
|---|---|---|
| LC CDR1 | QDVNTA | 14 |
| LC CDR2 | SAS | 15 |
| LC CDR3 | QQHYTTPPT | 16 |
| HC CDR1 | GFNIKDTY | 17 |
| HC CDR2 | IYPTNGYT | 18 |
| HC CDR3 | SRWGGDGFYAMDY | 19 |
| VL | DIQMTQSPSSLSASVGDRVTITC RASQDVNTAVAWYQQKPGKAPKL LIYSASFLYSGVPSRFSGSRSGT DFTLTISSLQPEDFATYYCQQHY TTPPTFGQGTKVEIK | 20 |
| VH | EVQLVESGGGLVGPGGSLRLSCA ASGFNIKDTYIHWVRQAPGKGLE WVARIYPTNGYTRYADSVKGRFT ISADTSKNTAYLQMNSLRAEDTA VYYCSRWGGDGFYAMDYWGQGTL VTVSS | 21 |
| VL-IgG Kappa | DIQMTQSPSSLSASVGDRVTITC RASQDVNTAVAWYQQKPGKAPKL LIYSASFLYSGVPSRFSGSRSGT DFTLTISSLQPEDFATYYCQQHY TTPPTFGQGTKVEIKRTVAAPSV FIFPPSDEQLKSGTASVVCLLNN FYPREAKVQWKVDNALQSGNSQE SVTEQDSKDSTYSLSSTLTLSKA DYEKHKVYACEVTHQGLSSPVTK SFNRGEC | 22 |
| VH-IgG1 | EVQLVESGGGLVGPGGSLRLSCA ASGFNIKDTYIHWVRGAPGKGLE WVARIYPTNGYTRYADSVKGRFT ISADTSKNTAYLQMNSLRAEDTA VYYCSRVVGGDGFYAMDYWGQGT LVTVSSASTKGPSVFPLAPSSKS TSGGTAALGCLVKDYFPEPVTVS WNSGALTSGVHTFPAVLQSSGLY SLSSVVTVPSSSLGTQTYICNVN HKPSNTKVDKKVEPPKSCDKTHT CPPCPAPELLGGPSVFLFPPKPK DTLMISRTPEVTCVVVDVSHEDP EVKFNWYVDGVEVHNAKTKPREE QYNSTYRVVSVLTVLHQDWLNGK EYKCKVSNKALPAPIEKTISKAK GQPREPQVYTLPPSRDELTKNQV SLTCLVKGFYPSDIAVEWESNGQ PENNYKTTPPVLDSDGSFFLYSK LTVDKSRWQQGNVFSCSVMHEAL HNHYTQKSLSLSPG | 23 |

LC, light chain;
HC, heavy chain;
VL, variable light chain;
VH, variable heavy chain.

Additional Steps

The methods disclosed herein, in various aspects, comprise additional steps. For example, in some aspects, the methods comprise one or more upstream steps or downstream steps involved in producing, purifying, and formulating a recombinant glycosylated protein. In exemplary embodiments, the method comprises steps for generating host cells that express a recombinant glycosylated protein (e.g., antibody or antibody binding protein). The host cells, in some aspects, are prokaryotic host cells, e.g., *E. coli* or *Bacillus subtilis*, or the host cells, in some aspects, are eukaryotic host cells, e.g., yeast cells, filamentous fungi cells, protozoa cells, insect cells, or mammalian cells (e.g., CHO cells). Such host cells are described in the art. See, e.g., Frenzel, et al., *Front Immunol* 4: 217 (2013) and herein under "Cells." For example, the methods comprise, in some instances, introducing into host cells a vector comprising a nucleic acid comprising a nucleotide sequence encoding the recombinant glycosylated protein, or a polypeptide chain thereof.

In exemplary embodiments, the methods disclosed herein comprise steps for isolating and/or purifying the recombinant glycosylated protein (e.g., recombinant antibody) from the culture. In exemplary aspects, the method comprises one or more chromatography steps including, but not limited to, e.g., affinity chromatography (e.g., protein A affinity chromatography), ion exchange chromatography, and/or hydrophobic interaction chromatography. In exemplary aspects, the method comprises steps for producing crystalline biomolecules from a solution comprising the recombinant glycosylated proteins.

The methods of the disclosure, in various aspects, comprise one or more steps for preparing a composition, including, in some aspects, a pharmaceutical composition, comprising the purified recombinant glycosylated protein. Such compositions are discussed below.

Compositions

Provided herein are compositions comprising recombinant glycosylated proteins. In exemplary embodiments, the compositions are prepared by the inventive methods of producing a recombinant glycosylated protein composition, described herein. In exemplary aspects, the recombinant glycosylated protein is an antibody. Accordingly, antibody compositions are provided herein. In exemplary embodiments, the antibody composition comprises different glycoforms of the antibody. In exemplary embodiments, the antibody composition comprises TAF glycoforms, HM glycoforms, and/or afucosylated glycoforms of the antibody. Compositions comprising antibody fragments or antibody protein products are also provided. In various aspects, the antibody fragments, antibody protein products, Glycosylated Fc Fragments, or Glycosylated Fc Fragment antibody products comprise a glycosylation site. In exemplary embodiments, the antibody composition is produced by a method comprising maintaining glycosylation-competent cells in a cell culture medium comprising fucose, wherein fucose is present in the culture medium at a concentration between about 0.17 g/L and about 1.0 g/L. In exemplary embodiments, the antibody composition is produced by a method comprising maintaining glycosylation-competent cells in a cell culture medium comprising fucose, wherein fucose is present in the culture medium at a concentration between about 0.1 g/L and about 1.0 g/L, and wherein the glycosylation-competent cells are not genetically modified to alter activity of an enzyme of the de novo pathway or the salvage pathway. In exemplary embodiments, the antibody composition is produced by a method comprising maintaining glycosylation-competent cells in a cell culture medium comprising fucose and glucose, wherein fucose is present in the culture medium at a concentration of about 0.1 g/L to about 1.0 g/L and adding glucose to the cell culture medium according to a glucose feeding schedule that achieves an average glucose concentration of about 10 g/L or less. In exemplary embodiments, the antibody composition is produced upon practicing a method of modulating the level of TAF glycans, afucosylated glycans, or high mannose glycan of an antibody composition produced by glycosylation-competent cells. In exemplary aspects, the antibody composition is produced upon practicing a method of modulating the level of TAF glycans comprising (A) adding fucose to a cell culture medium comprising the glycosylation-competent cells to achieve a fucose concentration of about 0.1 g/L to about 1.0 g/L to decrease the level of TAF glycans; (B) adding glucose to a cell culture medium comprising the glycosylation-competent cells to achieve a glucose concentration less than about 10 g/L to increase the level of TAF glycans; or (C) both (A) and (B). In exemplary aspects, the antibody composition is produced upon practicing a method of modulating the level of afucosylated glycans of an antibody composition produced by glycosylation-competent cells, comprising (A) adding fucose to a cell culture medium comprising the glycosylation-competent cells to achieve a fucose concentration of about 0.1 g/L to about 1.0 g/L to decrease the level of afucosylated glycans; (B) adding glucose to a cell culture medium comprising the glycosylation-competent cells to achieve a glucose concentration less than or about 10 g/L to increase the level of afucosylated glycans; or (C) both (A) and (B). In exemplary instances, the antibody composition is produced upon practicing a method of modulating the level of high mannose glycans of an antibody composition produced by glycosylation-competent cells, comprising adding glucose to a cell culture medium comprising the glycosylation-competent cells to achieve a glucose concentration less than or about 10 g/L to increase the level of high mannose glycans.

In exemplary aspects, less than or about 50% (e.g., less than or about 40%, less than or about 30%, less than or about 25%, less than or about 20%, less than or about 15%) of the recombinant glycosylated protein in the composition are TAF glycoforms. In exemplary aspects, less than about 10% (e.g., less than or about 9%, less than or about 8%, less than or about 7%, less than or about 6%, less than or about 5%, less than or about 4%, less than or about 3%, less than or about 2%) of the recombinant glycosylated protein in the composition are TAF glycoforms. In exemplary aspects, about 4% to about 10% of the recombinant glycosylated protein in the composition are TAF glycoforms. In exemplary aspects, about 2% to about 6% of the recombinant glycosylated protein in the composition are TAF glycoforms. In exemplary aspects, about 2.5% to about 5% of the recombinant glycosylated protein in the composition are TAF glycoforms. In exemplary aspects, less than or about 4% of the recombinant glycosylated protein in the composition are TAF glycoforms. In further exemplary aspects, less than or about 4% and greater than or about 2% of the recombinant glycosylated protein in the composition are TAF glycoforms.

In exemplary aspects, the compositions of the disclosure have a glycoform profile which is less than or about 50% (e.g., less than or about 40%, less than or about 30%, less than or about 25%, less than or about 20%, less than or about 15%) TAF glycoforms. In exemplary aspects, the compositions of the disclosure have a glycoform profile which is less than or about 10% (e.g., less than or about 9%, less than or about 8%, less than or about 7%, less than or about 6%, less than or about 5%, less than or about 4%, less than or about 3%, less than or about 2%) TAF glycoforms. In exemplary aspects, the compositions of the disclosure have a glycoform profile which comprises about 4% to about 10% TAF glycoforms. In exemplary aspects, the compositions of the disclosure have a glycoform profile which is about 2% to about 6% TAF glycoforms. In exemplary aspects, the compositions of the disclosure have a glycoform profile which is about 2.5% to about 5% TAF glycoforms. In exemplary aspects, the compositions of the disclosure have a glycoform profile which is less than or about 4% TAF glycoforms. In exemplary aspects, the compositions of the disclosure have a glycoform profile which is less than or about 4% and greater than or about 2% TAF glycoforms.

In exemplary aspects, less than or about 5% of the recombinant glycosylated protein (e.g., antibody or antibody binding protein) in the composition are afucosylated glycoforms. In exemplary aspects, less than or about 4% of the recombinant glycosylated protein (e.g., antibody or antibody binding protein) in the composition are afucosylated glycoforms. In exemplary aspects, less than or about 3.5% of the recombinant glycosylated protein (e.g., antibody or antibody binding protein) in the composition are afucosylated glycoforms. In exemplary aspects, about 0.8% to about 2.8% of the recombinant glycosylated protein in the composition are afucosylated glycoforms. In some aspects, the level of afucosylated glycans in the antibody composition is about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, or about 2.8%.

In exemplary aspects, less than or about 5% of the recombinant glycosylated protein (e.g., antibody or antibody binding protein) in the composition are high mannose glycoforms. In exemplary aspects, less than or about 4% of the recombinant glycosylated protein (e.g., antibody or antibody binding protein) in the composition are high mannose glycoforms. In exemplary aspects, less than or about 3.5% of the recombinant glycosylated protein (e.g., antibody or antibody binding protein) in the composition are high mannose glycoforms. In exemplary aspects, about 0.7% to about 3.0% of the recombinant glycosylated protein in the composition are high mannose glycoforms. In some aspects, the level of high mannose glycans in the antibody composition is about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0%.

In exemplary embodiments, the composition is combined with a pharmaceutically acceptable carrier, diluent or excipient. Accordingly, provided herein are pharmaceutical compositions comprising the recombinant glycosylated protein composition (e.g., the antibody composition or antibody binding protein composition) described herein and a pharmaceutically acceptable carrier, diluent or excipient. As used herein, the term "pharmaceutically acceptable carrier" includes any of the standard pharmaceutical carriers, such as a phosphate buffered saline solution, water, emulsions such as an oil/water or water/oil emulsion, and various types of wetting agents.

Cell-Culture Medium

Provided herein is a cell culture medium comprising: (a) glycosylation-competent cells comprising an exogenous nucleotide sequence encoding an antibody; and (b) a culture medium comprising fucose at a concentration of about 0.1 g/L to about 1.0 g/L or about 0.17 g/L to about 1.0 g/L. The glycosylation-competent cells may be any cell described herein. In exemplary instances, the glycosylation-competent cells are not genetically modified to alter activity of an enzyme of the de novo pathway or the salvage pathway, optionally, wherein the glycosylation-competent cells are not genetically modified to knock-out a gene encoding GDP-keto-6-deoxymannonse-3,5-epimerase, 4-reductase. In exemplary embodiments, the culture medium further comprises glucose. In some aspects, the culture medium comprises glucose at a concentration less than about 10 g/L or less than about 9 g/L, e.g., about 6 g/L or less or about 0.5 g/L to about 4 g/L. In some aspects, the culture medium comprising the fucose. In exemplary aspects, the pH of the culture medium is about 6.85 to about 7.05, optionally, about 6.90 to about 7.00. In exemplary instances, the glycosylation-competent cells are not genetically modified to alter activity of an enzyme of the de novo pathway or the salvage pathway. For example, the glycosylation-competent cells are not genetically modified to knock-out a gene encoding GDP-keto-6-deoxymannonse-3,5-epimerase, 4-reductase. In exemplary aspects, the antibody is an IgG antibody, optionally, an IgG1 antibody. The IgG1 antibody in exemplary aspects is specific for a tumor associated antigen, e.g., CD20. In exemplary aspects, the cell culture medium does not comprise mannose.

Modulation Methods

Methods of altering or modulating the levels of TAF glycans of a recombinant glycosylated protein (e.g., an antibody composition or antibody binding protein composition) produced by glycosylation-competent cells in a cell culture medium are further provided herein. In exemplary aspects, the method comprises (A) adding fucose to a cell culture medium comprising the glycosylation-competent cells to achieve a fucose concentration of about 0.1 g/L to about 1.0 g/L to decrease the level of TAF glycans; (B) adding glucose to a cell culture medium comprising the glycosylation-competent cells to achieve a glucose concentration less than about 10 g/L to increase the level of TAF glycans; or (C) both (A) and (B).

The present disclosure also provides methods of modulating the level of afucosylated glycans of a recombinant glycosylated protein (e.g., an antibody composition or antibody binding protein composition) produced by glycosylation-competent cells. In exemplary aspects, the methods comprise (A) adding fucose to a cell culture medium comprising the glycosylation-competent cells to achieve a fucose concentration of about 0.1 g/L to about 1.0 g/L to decrease the level of afucosylated glycans; (B) adding glucose to a cell culture medium comprising the glycosylation-competent cells to achieve a glucose concentration less than about 10 g/L to increase the level of afucosylated glycans; or (C) both (A) and (B).

Also provided are methods of modulating the level of high mannose glycans of a recombinant glycosylated protein (e.g., an antibody composition or antibody binding protein composition) produced by glycosylation-competent cells. In exemplary embodiments, the methods comprise adding glucose to a cell culture medium comprising the glycosylation-competent cells to achieve a glucose concentration less than about 10 g/L to increase the level of HM glycans.

Accordingly, in some exemplary embodiments, the methods of the disclosure relate to increasing the levels of TAF, HM, or afucosylated glycans of a protein, e.g., an antibody, produced by cells in a cell culture. In exemplary aspects, the levels of HM glycoforms of the recombinant glycosylated protein are increased, relative to the control cell culture. In exemplary aspects, the levels of one or more of Man5, Man6, Man7, Man8, and/or Man9 of the recombinant glycosylated protein are increased, relative to the control cell culture. In exemplary aspects, the levels of afucosylated glycoforms of the recombinant glycosylated protein are increased, relative to the control cell culture. In exemplary aspects, the levels of one or more of A1 G0, A2G0, A2G1a, A2G1b, A2G2, and A1 G1M5 of the recombinant glycosylated protein are increased, relative to the control cell culture. In exemplary aspects, the levels of one or more of A1G1a, G0[H3N4], G0[H4N4], G0[H5N4], and FO-N [H3N3] of the recombinant glycosylated protein are increased, relative to the control cell culture. In some aspects, the increase is an increase relative to the control cell culture, as determined by Hydrophilic Interaction Liquid Chromatography (HILIC). In some aspects, the increase is an increase relative to the control cell cultured as determined by methods known to one of skill in the art.

In some aspects, the methods of the disclosure increase the levels of TAF, HM, or afuco glycoform to any degree or level relative a control cell culture. For example, in some aspects, the increase provided by the methods of the disclosure is at least or about a 1% to about a 10% increase (e.g., at least or about a 1% increase, at least or about a 2% increase, at least or about a 3% increase, at least or about a 4% increase, at least or about a 5% increase, at least or about a 6% increase, at least or about a 7% increase, at least or about a 8% increase, at least or about a 9% increase, at least or about a 9.5% increase, at least or about a 9.8% increase, at least or about a 10% increase) relative a control cell culture. In exemplary embodiments, the increase provided by the methods of the disclosure is over 100%, e.g., 200%, 300%, 400%, 500%, 600%, 700%, 800%, 900% or even 1000% relative a control cell culture. In exemplary embodiments, the level of TAF, HM, or afuco glycoforms of the protein increases by at least about 1.5-fold, relative a control cell culture. In exemplary embodiments, the level of TAF, HM, or afuco glycoforms of the protein increases by at least about 2-fold, relative a control cell culture. In exemplary embodiments, the level of TAF, HM, or afuco glycoforms of the protein increases by at least about 3-fold, relative a control cell culture. In exemplary embodiments, the level of TAF, HM, or afuco glycoforms of the protein increases by at least about 4-fold or about 5-fold, relative to a control cell culture.

In exemplary aspects, the increased level of TAF glycoforms of the recombinant glycosylated protein is observed or observable or detected or detectable as early as the $1^{st}$ day after the fucose and/or glucose concentration is changed. In exemplary aspects, the increased level of TAF glycoforms of the recombinant glycosylated protein is observed or observable or detected or detectable as early as the $2^{nd}$ day post-change. In exemplary aspects, the increased level of TAF glycoforms of the recombinant glycosylated protein is observed or observable or detected or detectable as early as the $3^{rd}$ day post-change. In exemplary aspects, the increased level of TAF glycoforms of the recombinant glycosylated protein is observed or observable or detected or detectable as early as about the $4^{th}$ day post-change. In exemplary aspects, the increased level of TAF glycoforms of the recombinant glycosylated protein is observed or observable or detected or detectable after about the $5^{th}$ day post-change. In exemplary aspects, the increased level of TAF glycoforms of the protein is observed or observable or detected or detectable at the time the recombinant glycosylated protein is harvested from the cell culture.

In exemplary aspects, the increased level of TAF glycoforms of the recombinant glycosylated protein is observed for longer than about the 4th, $5^{th}$ or $6^{th}$ day of cell culture or beyond. In exemplary aspects, the increased level of TAF glycoforms of the recombinant glycosylated protein is observed for 7, 8, 9, 10, 11 or 12 days of cell culture (post-inoculation), or longer (e.g., about 2 weeks, about 3 weeks, about 4 weeks, about 1 month, about 2 months, about 3 months, about 6 months, or about 1 year). In exemplary aspects, the increased level of TAF glycoforms of the protein is observed at the time the protein is harvested from the cell culture.

In other aspects, the methods of the disclosure relate to decreasing the levels of TAF glycoforms of a protein produced by cells in a cell culture. In exemplary aspects, the levels of HM glycoforms of the recombinant glycosylated protein are decreased, relative to the control cell culture. In exemplary aspects, the levels of one or more of Man5, Man6, Man7, Man8, and/or Man9 of the recombinant glycosylated protein are decreased, relative to the control cell culture. In exemplary aspects, the levels of afucosylated glycoforms of the recombinant glycosylated protein are decreased, relative to the control cell culture. In exemplary aspects, the levels of one or more of A1G0, A2G0, A2G1a, A2G1b, A2G2, and A1G1M5 of the recombinant glycosylated protein are decreased, relative to the control cell culture. In exemplary aspects, the levels of one or more of A1G1a, G0[H3N4], G0[H4N4], G0[H5N4], and F0-N [H3N3] of the recombinant glycosylated protein are decreased, relative to the control cell culture. In exemplary aspects, the method is a method of decreasing the level of TAF glycoforms by about 1% to about 4% and the method comprises maintaining the glycosylation-competent cells in a first cell culture medium cell and increasing the fucose concentration to about 0.1 g/L to about 1.0 g/L. In some aspects, the decrease is a decrease relative to the control cell culture, as determined by HILIC. In some aspects, the decrease is a decrease relative to the control cell cultured as determined by methods known to one of skill in the art.

In some aspects, the methods of the disclosure decrease the level(s) of TAF, HM, or afuco glycoform to any degree or level relative a control cell culture. For example, the decrease provided by the methods of the disclosure is at least or about a 0.1% to about a 1% decrease (e.g., at least or about a 0.1% decrease, at least or about a 0.2% decrease, at least or about a 0.3% decrease, at least or about a 0.4% decrease, at least or about a 0.5% decrease, at least or about a 0.6% decrease, at least or about a 0.7% decrease, at least or about a 0.8% decrease, at least or about a 0.9% decrease, at least or about a 0.95% decrease, at least or about a 0.98% decrease, at least or about a 1.0% decrease) relative to the level of a control cell culture. In exemplary embodiments, the decrease provided by the methods of the disclosure is over about 100%, e.g., about 200%, about 300%, about 400%, about 500%, about 600%, about 700%, about 800%, about 900% or even about 1000% relative to the level of a control cell culture. In exemplary embodiments, the level of TAF, HM, or afuco glycoforms of the protein decreases by at least or about 1.5-fold, relative to a control cell culture. In exemplary embodiments, the level of TAF, HM, or afuco glycoforms of the protein decreases by at least about 2-fold, relative to a control cell culture. In exemplary embodiments, the level of TAF, HM, or afuco glycoforms of the protein decreases by at least about 3-fold, relative to a control cell culture. In exemplary embodiments, the level of TAF, HM, or afuco glycoforms of the protein decreases by at least about 4-fold or by at least about 5-fold, relative to a control cell culture.

In exemplary aspects, the decreased level of TAF glycoforms of the recombinant glycosylated protein is observed or observable or detected or detectable as early as about the $1^{st}$ day post-inoculation. In exemplary aspects, the decreased level of TAF glycoforms of the recombinant glycosylated protein is observed or observable or detected or detectable as early as about the $2^{nd}$ day post-inoculation. In exemplary aspects, the decreased level of TAF glycoforms of the recombinant glycosylated protein is observed or observable or detected or detectable as early as about the $3^{rd}$ day post-inoculation. In exemplary aspects, the decreased level of TAF glycoforms of the recombinant glycosylated protein is observed or observable or detected or detectable as early as about the $4^{th}$ day post-inoculation. In exemplary aspects, the decreased level of TAF glycoforms of the recombinant glycosylated protein is observed or observable or detected or detectable after about the $5^{th}$ day post-inoculation. In exemplary aspects, the decreased level of TAF glycoforms of the recombinant glycosylated protein is observed or observable or detected or detectable at about the time the protein is harvested from the cell culture.

In exemplary aspects, the decreased level of TAF glycoforms of the protein is observed for longer than about the $4^{th}$, about the $5^{th}$, or about the $6^{th}$ day of cell culture or beyond the initial cell culture period. In exemplary aspects, the decreased level of TAF glycoforms of the protein is observed for about 7, about 8, about 9, about 10, about 11 or about 12 days of cell culture (post-inoculation), or longer (e.g., about 2 weeks, about 3 weeks, about 4 weeks, about 1 month, about 2 months, about 3 months, about 6 months, or about 1 year). In exemplary aspects, the decreased level of TAF glycoforms of the protein is observed at about the time the protein is harvested from the cell culture.

With regard to the methods of the disclosure, the modulation, increase or decrease affected by such methods are relative to a "control" or a "control cell culture." In exemplary aspects, the control is the level of TAF glycoforms of the protein when the steps of the inventive method are not carried out. In exemplary aspects, the control is the level of TAF glycoforms of the protein when a known method of recombinant production is carried out. In exemplary aspects, the control is the level of TAF glycoforms when a known glucose or fucose concentration is maintained during recombinant production. As used herein, the term "control cell culture" means a cell culture maintained in the same manner as the cell culture on which the steps of the inventive method are carried out (e.g., cell culture of the disclosed methods) except for the fucose/glucose concentration. In exemplary aspects, the control cell culture is a cell culture maintained at known operational or standard parameters, including a control fucose/glucose concentration. As used herein, the term "control fucose concentration" or "control glucose concentration" may refer to a known operational fucose/glucose concentration, e.g., a fucose/glucose concentration of a cell culture maintained at a first time point or at a time point before carrying out the methods of the disclosure. In exemplary aspects, a control fucose/glucose concentration is a fucose/glucose concentration of a cell culture for which the TAF levels are known or determined.

In exemplary aspects of the modulating methods of the disclosure, the glycosylation-competent cells are not genetically modified to alter activity of an enzyme of the de novo pathway or the salvage pathway. Optionally, the glycosylation-competent cells are not genetically modified to knock-out a gene encoding GDP-keto-6-deoxymannonse-3,5-epimerase, 4-reductase.

In exemplary aspects, after the methods of the disclosure are carried out, the level of TAF glycans in the antibody composition is less than about 10%, e.g., about 2% to about 6%, about 2% to about 5%, or about 2% to about 4%.

In exemplary aspects, after the methods of the disclosure are carried out, the level of high mannose glycans in the antibody composition is less than about 3.5%, optionally, about 0.7% to about 3.0%.

In exemplary aspects, after the methods of the disclosure are carried out, the level of afucosylated glycans in the antibody composition is less than about 3.5%, optionally, about 0.8% to about 2.8%.

With regard to the modulating methods described herein comprising adding fucose, the final fucose concentration of the cell culture medium, in various aspects, is about 0.17 g/L to about 1.0 g/L, or about 0.2 g/L to about 0.5 g/L. However, any of the fucose concentrations described herein are contemplated.

With regard to the modulating methods described herein comprising adding glucose to the cell culture medium, in some aspects, the glucose is added according to a glucose feeding schedule that achieves an average glucose concentration of about 10 g/L or less or about 9 g/L or less. In some aspects, the average glucose concentration is less than about 6.0 g/L, optionally, less than about 4.0 g/L. In some instances, the average glucose concentration is based on the fucose concentration of the cell culture medium. For example, the average glucose concentration may be calculated based on the Formula I:

$$T = 3.354 - 1.388F + 0.111G + [F - 0.4375] \times [1.9527(F - 0.4375)] \quad \text{Formula I}$$

wherein T is the targeted % TAF glycans and is 2.5% to about 6%, about 2.75% to about 5.5%, or about 3% to about 5%, F is the concentration (g/L) of fucose in the medium, and G is the average glucose concentration (g/L).

The present disclosure additionally provides methods of modulating (reducing or increasing) the level of afucosylated glycans of a recombinant glycosylated protein composition (e.g., an antibody composition or antibody binding protein composition) produced by glycosylation-competent cells. In exemplary embodiments, the method comprises reducing the pH of the cell culture medium by about 0.03 to about 1.2 (e.g., 0.05 to about 1.0) to reduce the level of afucosylated glycans of a recombinant glycosylated protein composition (e.g., an antibody composition or antibody binding protein composition) by about 0.5% to about 2% (e.g., 0.5% to about 1.5%, 0.5% to about 1.0%, 1.0% to about 2%, 1.5% to about 2.0%) or increasing the pH of the cell culture medium by about 0.03 to about 1.2 (e.g., 0.05 to about 1.0) to increase the level of afucosylated glycans of a recombinant glycosylated protein composition (e.g., an antibody composition or antibody binding protein composition) by about 0.5% to about 2% (e.g., 0.5% to about 1.5%, 0.5% to about 1.0%, 1.0% to about 2%, 1.5% to about 2.0%). In exemplary aspects, the method comprises reducing the pH of the cell culture medium by about 0.05 to about 1.2 (e.g., 0.06, 0.07, 0.08, 0.09, 1.1, 1.11, 1.12, 1.13, 1.14, 1.15, 1.16, 1.17, 1.18, 1.19, 1.20), to reduce the level of afucosylated glycans of the recombinant glycosylated protein composition (e.g., an antibody composition or antibody binding protein composition) by about 1% to about 2% (e.g., 1.0% to 1.5%, 1.5% to 2.0%) or increasing the pH of the cell culture medium by about 0.05 to about 1.2 (e.g., 0.06, 0.07, 0.08, 0.09, 1.1, 1.11, 1.12, 1.13, 1.14, 1.15, 1.16, 1.17, 1.18, 1.19, 1.20), to increase the level of afucosylated glycans of the recombinant glycosylated protein composition (e.g., an antibody composition or antibody binding protein composition) by about 1% to about 2% (e.g., 1.0% to 1.5%, 1.5% to 2.0%). In various instances, the method comprises reducing the pH of the cell culture medium by about 0.03 to about 0.07 (e.g., 0.03, 0.04, 0.05, 0.06, 0.07) to reduce the level of afucosylated glycans of the recombinant glycosylated protein composition (e.g., an antibody composition or antibody binding protein composition) by about 0.5% to about 1.1% (e.g., 0.05%, 0.06%, 0.07%, 0.08%, 0.09%. 1.0%, 1.01%, 1.02%, 1.03%, 1.04%, 1.05%, 1.06%, 1.07%, 1.08%, 1.09%, 1.10%) or increasing the pH of the cell culture medium by about 0.03 to about 0.07 (e.g., 0.03, 0.04, 0.05, 0.06, 0.07) to increase the level of afucosylated glycans of the recombinant glycosylated protein composition (e.g., an antibody composition or antibody binding protein composition) by about 0.5% to about 1.1% (e.g., 0.05%, 0.06%, 0.07%, 0.08%, 0.09%. 1.0%, 1.01%, 1.02%, 1.03%, 1.04%, 1.05%, 1.06%, 1.07%, 1.08%, 1.09%, 1.10%).

Methods of reducing the level of afucosylated glycans of a recombinant glycosylated protein composition (e.g., an antibody composition or antibody binding protein composition) produced by glycosylation-competent cells by about 1% to about 2% are also provided herein. In exemplary embodiments, the method comprises reducing the pH of the cell culture medium by about 0.05 to about 1.2. Optionally, the method comprises reducing the pH by about 0.05 to about 0.07 for a reduction in afucosylated glycans of about 1% or reducing the pH by about 0.09 to about 1.2 for a reduction in afucosylated glycans of more than about 1.5%. In various aspects, the method comprises culturing the cells at a pH between about 7.10 to about 7.20, optionally about 7.12 to about 7.19.

Methods of reducing the level of afucosylated glycans of a recombinant glycosylated protein composition (e.g., an antibody composition or antibody binding protein composition) produced by glycosylation-competent cells by about 0.5% to about 1.1% are furthermore provided. In exemplary embodiments, the method comprises reducing the pH of the cell culture medium by about 0.03-0.07. In various aspects, the method comprises reducing the pH by about 0.03 to about 0.06 for a reduction in afucosylated glycans of about 0.8%. In some aspects, the method comprises reducing the pH by about 0.05 to about 0.07 for a reduction in afucosylated glycans of about 1%. In various instances, the method comprises culturing the cells at a pH between about 7.05 to about 7.15, optionally about 7.07 to about 7.13.

Methods of increasing the level of afucosylated glycans of a recombinant glycosylated protein composition (e.g., an antibody composition or antibody binding protein composition) produced by glycosylation-competent cells by about 1% to about 2% are provided by the present disclosure. In exemplary embodiments, the method comprises increasing the pH of the cell culture medium by about 0.05 to about 1.2. Optionally, the method comprises increasing the pH by about 0.05 to about 0.07 for a reduction in afucosylated glycans of about 1% or increasing the pH by about 0.09 to about 1.2 for a reduction in afucosylated glycans of more than about 1.5%. In some aspects, the method comprises culturing the cells at a pH between about 7.10 to about 7.20, optionally about 7.12 to about 7.19.

The present disclosure also provides methods of increasing the level of afucosylated glycans of a recombinant glycosylated protein composition (e.g., an antibody composition or antibody binding protein composition) produced by glycosylation-competent cells by about 0.5% to about 1.1%. In exemplary embodiments, the method comprises increasing the pH of the cell culture medium by about 0.03-0.07 or increasing the pH by about 0.03 to about 0.06 for a reduction in afucosylated glycans of about 0.8% or increasing the pH by about 0.05 to about 0.07 for a reduction in afucosylated glycans of about 1%. In various instances, the method comprises culturing the cells at a pH between about 7.05 to about 7.15, optionally about 7.07 to about 7.13.

In any of the foregoing methods, the pH of the cell culture medium throughout the culture is greater than 7.0, optionally, higher than 7.05 and less than 7.2. In some aspects, the level of afucosylated glycans in the recombinant glycosylated protein composition (e.g., an antibody composition or antibody binding protein composition) is less than about 10%, e.g., about 6.2% to about 8.4%. In any of the foregoing methods, the temperature changes by less than 2 degrees C. during the culture period. For example, in some aspects, the temperature of the culture changes by not more than 1.5 or 1.0 degrees C. In any of the foregoing methods, the cell culture medium does not comprise any detectable amounts of manganese or betaine. The cell culture medium in some aspects comprises about 0.10 g/L to about 1.0 g/L fucose, optionally, about 0.17 to about 1.0 g/L fucose. Optionally, fucose is present in the culture medium at a concentration less than about 0.75 g/L, less than about 0.6 g/L, or about 0.2 g/L to about 0.5 g/L. The addition or presence of fucose in the culture medium may be in accordance with any of the teachings provided herein. In exemplary aspects, the glycosylation-competent cells are not genetically modified to alter activity of an enzyme of the de novo pathway or the salvage pathway. In any of the foregoing methods, glucose is added to the cell culture medium according to a glucose feeding schedule that achieves an average glucose concentration of about 10 g/L or less. The glucose may be added in accordance with any of the teachings provided herein.

As discussed above, TAF glycans is the sum of HM glycans and afucosylated glycans. Accordingly, the presently disclosed methods of modulating afucosylated glycans will in various instances modulate the level of TAF glycans of a recombinant glycosylated protein composition (e.g., an antibody composition or antibody binding protein composition). Accordingly, methods of modulating the level of TAF glycans of a recombinant glycosylated protein composition (e.g., an antibody composition or antibody binding protein composition) produced by glycosylation-competent cells are provided herein. The method in exemplary aspects comprises modulating the level of afucosylated glycans of the recombinant glycosylated protein composition (e.g., an antibody composition or antibody binding protein composition) in accordance with a presently disclosed method of modulating the level of afucosylated glycans. In exemplary embodiments, the method of modulating TAF glycans comprises reducing the level of afucosylated glycans of the recombinant glycosylated protein composition (e.g., an antibody composition or antibody binding protein composition) in accordance with a presently disclosed method of reducing the level of afucosylated glycans or increasing the level of afucosylated glycans of the recombinant glycosylated protein composition (e.g., an antibody composition or antibody binding protein composition) in accordance with a presently disclosed method of increasing afucosylated glycans.

A method of producing an antibody composition, wherein the level of afucosylated glycans in the antibody composition is about 6.2% to about 8.4%, is furthermore provided by the present disclosure. In exemplary embodiments, the method comprises maintaining glycosylation-competent cells in a cell culture medium at a pH higher than 7.05 and lower than 7.2,
  wherein, optionally:
  (A) the pH of the cell culture medium changes by less than 0.15 (optionally by less than 0.10) during the culture period or
  (B) the temperature of the cell culture medium changes by not more than 2 degrees C. or
  (C) the method does not comprise culturing the cells in a cell culture medium comprising manganese or betaine or
  (D) a combination of two or three of (A), (B), and (C).

In various aspects, the pH is maintained at a pH of about 7.07 to about 7.19 (e.g. 7.08, 7.09, 7.10, 7.11, 7.12, 7.13, 7.14, 7.15, 7.16, 7.17, 7.18, or 7.19) during the culture period, optionally, wherein the pH is maintained at about 7.07 or higher and below 7.10, or about 7.10 or higher and below 7.15, or about 7.15 or higher up to about 7.19. In various aspects, the level of afucosylated glycans in the antibody composition is less than about 10%, optionally, about 6.2% to about 8.4%. In various instances, the temperature changes by less than 2 degrees C. during the culture period, optionally, the temperature of the culture changes by not more than 1.5 or 1.0 degrees C. In various aspects, the cell culture medium does not comprise any detectable amounts of manganese or betaine. In exemplary aspects, the cell culture medium comprises about 0.10 g/L to about 1.0 g/L fucose, optionally, about 0.17 to about 1.0 g/L fucose, optionally, fucose is present in the culture medium at a concentration less than about 0.75 g/L, less than about 0.6 g/L, or about 0.2 g/L to about 0.5 g/L. In some aspects, the glycosylation-competent cells are not genetically modified to alter activity of an enzyme of the de novo pathway or the salvage pathway, and in some aspects, glucose is added to the cell culture medium according to a glucose feeding schedule that achieves an average glucose concentration of about 10 g/L or less.

Exemplary Embodiments

The disclosure provides methods of producing a recombinant glycosylated protein composition (e.g., an antibody composition or antibody binding protein composition). In exemplary embodiments, the method comprises maintaining glycosylation-competent cells in a cell culture medium comprising fucose and/or glucose at a specific concentration as described herein, depending on the level of TAF glycoforms desired. In exemplary embodiments, the level of TAF glycoforms in the recombinant glycosylated protein composition (e.g., antibody composition or antibody binding protein composition) is less than or about 10% and, in exemplary aspects, the method comprises maintaining glycosylation-competent cells in a cell culture medium comprising fucose, wherein fucose is present in the culture medium at a concentration between about 0.17 g/L and about 1.0 g/L. In exemplary embodiments, the level of TAF glycoforms in the recombinant glycosylated protein composition (e.g., antibody composition or antibody binding protein composition) is less than or about 10% and, in exemplary aspects, the method comprises maintaining glycosylation-competent cells in a cell culture medium comprising fucose, wherein fucose is present in the culture medium at a concentration between about 0.1 g/L and about 1.0 g/L, and wherein the glycosylation-competent cells are not genetically modified to alter activity of an enzyme of the de novo pathway or the salvage pathway. The disclosure also provides methods of producing a recombinant glycosylated protein composition (e.g., an antibody composition or antibody binding protein composition) comprising maintaining glycosylation-competent cells in a cell culture medium comprising fucose and glucose, wherein fucose is present in the culture medium at a concentration of about 0.1 g/L to about 1.0 g/L and adding glucose to the cell culture medium according to a glucose feeding schedule that achieves an average glucose concentration of about 10 g/L or less. In exemplary aspects, fucose is present in the culture medium at a concentration less than about 0.75 g/L, optionally less than about 0.6 g/L. In exemplary instances, fucose is present in the culture medium at a concentration of about 0.2 g/L to about 0.5 g/L. In some aspects, fucose is present in the culture medium the entire duration the glycosylation-competent cells are maintained in cell culture. In exemplary instances, the method of producing a recombinant glycosylated protein composition (e.g., an antibody composition or antibody binding protein composition) comprises maintaining the glycosylation-competent cells in a first cell culture medium for an initial time period and subsequently maintaining the glycosylation-competent cells in a second cell culture medium, wherein the first cell culture medium does not comprise fucose at a concentration of about 0.1 g/L to about 1.0 g/L and the second cell culture medium comprises fucose at a concentration of about 0.1 g/L to about 1.0 g/L. In some instances, the initial time period is about 24 to about 72 hours. In alternative aspects, the initial time period is about or greater than about 72 hours but less than or about 156 hours. In some aspects, fucose is added to the first culture medium on the 6th day post-cell culture inoculation to obtain the second cell culture medium. the concentration of fucose fluctuates by about 0.2 g/L or less (e.g., 0.1 g/L or less) during the time the glycosylation-competent cells are maintained in the cell culture medium comprising fucose. In some aspects, the cell culture medium comprises an initial glucose concentration for an initial time period. Optionally, the initial glucose concentration is about 1 g/L to about 15 g/L, e.g., about 12 g/L±1 g/L. In exemplary aspects, the method further comprises adding glucose to the cell culture medium according to a glucose feeding schedule. In exemplary aspects, the glucose feeding schedule is initiated at about 4 to about 6 days post-cell culture inoculation. For example, the glucose feeding schedule may be initiated at about 6 days post-cell culture inoculation. In exemplary instances, the glucose feeding schedule achieves an average glucose concentration of about 10 g/L or less (e.g., about 9 g/L or less, about 6 g/L or less) in the cell culture medium, about 0.5 g/L to about 4 g/L). In exemplary instances, the glucose feeding schedule achieves an average glucose concentration based on the concentration of fucose in the cell culture medium. In exemplary aspects, the average glucose concentration is calculated based on Formula I:

$$T=3.354-1.388F+0.111G+[F-0.4375]\times[1.9527(F-0.4375)]$$ (Formula I)

wherein T is the targeted % total afucosylated (TAF) glycans in the antibody composition and is about 2.5% to about 6%, about 2.75% to about 5.5%, or about 3% to about 5%, F is the concentration (g/L) of fucose in the medium, and G is the average glucose concentration (g/L) in the medium. In exemplary aspects, (i) the concentration of fucose is about 0.2±0.1 g/L and the average glucose concentration is about 2 to about 4 g/L; (ii) the concentration of fucose is about 0.5±0.1 g/L and the average glucose concentration is about 3 to about 6 g/L; or (iii) the concentration of fucose is about 0.75±0.1 g/L and the average glucose concentration is about 4.5 to about 9 g/L. In exemplary aspects, the pH of the cell culture medium is about 6.85 to about 7.05 (e.g., about 6.90 to about 7.00). In some aspects, the glycosylation-competent cells are not genetically modified to alter activity of an enzyme of the de novo pathway or the salvage pathway. For example, the glycosylation-competent cells are not genetically modified to knock-out a gene encoding GDP-keto-6-deoxymannonse-3,5-epimerase, 4-reductase. In exemplary instances, the level of total afucosylated (TAF) glycans in the antibody composition is less than about 10% (e.g., about 2% to about 6%, about 2% to about 5%, about 2% to about 4%). In exemplary instances, the level of high mannose glycans in the antibody composition is less than about 3.5% (e.g., about 0.7% to about 3.0%). In exemplary instances, the level of afucosylated glycans in the antibody composition is less than about 3.5% (e.g., about 0.8% to about 2.8%). In some aspects, the glycosylation-competent cells produce IgG antibodies, optionally, IgG1 antibodies. In some aspects, the IgG1 antibodies are specific for a tumor-associated antigen (e.g., CD20). In exemplary aspects, the culture medium does not comprise mannose.

A cell culture medium comprising: (a) glycosylation-competent cells comprising an exogenous nucleic acid encoding an antibody; and (b) a culture medium comprising fucose at a concentration of about 0.1 g/L to about 1.0 g/L or about 0.17 g/L to about 1.0 g/L are provided. In exemplary aspects, the glycosylation-competent cells are not genetically modified to alter activity of an enzyme of the de novo pathway or the salvage pathway, optionally, wherein the glycosylation-competent cells are not genetically modified to knock-out a gene encoding GDP-keto-6-deoxymannonse-3,5-epimerase, 4-reductase. In exemplary aspects, the culture medium further comprises glucose at a concentration less than about 10 g/L, e.g., less than about 9 g/L, less than about 6 g/L, or about 0.5 g/L to about 4 g/L. In exemplary aspects, the pH of the culture medium is about 6.85 to about 7.05, e.g., about 6.9 to about 7.0. In some aspects, the cell culture medium does not comprise mannose. In exemplary aspects, the antibody is an IgG antibody, e.g., an IgG1 antibody. In exemplary instances, the IgG1 antibody is specific for a tumor-associated antigen, e.g., CD20.

Methods of altering or modulating the level of TAF glycans of a recombinant glycosylated protein composition (e.g., an antibody composition or antibody binding protein composition) produced by glycosylation-competent cells in a cell culture medium are further provided herein. In exemplary aspects, the method comprises (A) adding fucose to a cell culture medium comprising the glycosylation-competent cells to achieve a fucose concentration of about 0.1 g/L to about 1.0 g/L to decrease the level of TAF glycans; (B) adding glucose to a cell culture medium comprising the glycosylation-competent cells to achieve a glucose concentration less than about 10 g/L to increase the level of TAF glycans; or (C) both (A) and (B). Also provided are methods of modulating the level of afucosylated glycans of a recombinant glycosylated protein composition (e.g., an antibody composition or antibody binding protein composition) produced by glycosylation-competent cells. In exemplary embodiments, the method comprises (A) adding fucose to a cell culture medium comprising the glycosylation-competent cells to achieve a fucose concentration of about 0.1 g/L to about 1.0 g/L to decrease the level of afucosylated glycans; (B) adding glucose to a cell culture medium comprising the glycosylation-competent cells to achieve a glucose concentration less than or about 10 g/L to increase the level of afucosylated glycans; or (C) both (A) and (B). The present disclosure further provides a method of modulating the level of high mannose glycans of a recombinant glycosylated protein composition (e.g., an antibody composition or antibody binding protein composition) produced by glycosylation-competent cells. In exemplary embodiments, the method comprises adding glucose to a cell culture medium comprising the glycosylation-competent cells to achieve a glucose concentration less than about 10 g/L to increase the level of HM glycans. In exemplary aspects of the methods of modulating, the glycosylation-competent cells are not genetically modified to alter activity of an enzyme of the de novo pathway or the salvage pathway. For example, the glycosylation-competent cells are not in some aspects, genetically modified to knock-out a gene encoding GDP-keto-6-deoxymannonse-3,5-epimerase, 4-reductase. In some aspects, the level of TAF glycans in the antibody composition is less than or about 10% (e.g., about 2% to about 6%, about 2% to about 5%, about 2% to about 4%). In some aspects, the level of high mannose glycans in the antibody composition is less than or about 3.5% (e.g., about 0.7% to about 3.0%). In some aspects, the level of afucosylated glycans in the antibody composition is less than or about 3.5% (e.g., about 0.8% to about 2.8%). In exemplary aspects, the fucose concentration is about 0.17 g/L to about 1.0 g/L, optionally, about 0.2 g/L to about 0.5 g/L. In some aspects, the method further comprises adding glucose to the cell culture medium according to a glucose feeding schedule that achieves an average glucose concentration of about 10 g/L (e.g., less than about 9.0 g/L, less than about 6.0 g/L, less than about 4.0 g/L). In some instances, the average glucose concentration is based on the fucose concentration of the cell culture medium. For example, in some aspects, the average glucose concentration is calculated based on Formula I:

$$T=3.354-1.388F+0.111G+[F-0.4375]\times[1.9527(F-0.4375)]$$ Formula I wherein T is the targeted % total afucosylated (TAF) glycans in an antibody composition and is about 2.5% to about 6%, about 2.75% to about 5.5%, or about 3% to about 5%, F is the concentration (g/L) of fucose in the medium, and G is the average glucose concentration (g/L).

The following examples are given merely to illustrate the present disclosure and not in any way to limit its scope.

EXAMPLES

Example 1

This example describes the methods carried out and materials used in the experiments of Example 2.

Cell Lines, Cell Culture and Media

All experiments were performed using a clone expressing an antibody comprising a light chain comprising SEQ ID NO: 1 and a heavy chain comprising SEQ ID NO: 2. All experiments were performed using a separate vial of cells cultured for 25 days. The following parameters were held constant: duration (12 days), dissolved oxygen (48 mm Hg to 74 mm Hg), pH (6.85 to 7.05), agitation (350 RPM, 20 W/m³), temperature (36.0° C.).

Hydrophilic Interaction Liquid Chromatography (HILIC) Glycan Map

The glycan map of enzymatically released N-linked glycans was determined using HILIC. Briefly, glycans were incubated with a solution comprising PNGase F and a sodium phosphate buffer (pH 7.5) for ~2 hours at ~37° C. A labeling solution comprising 2-aminobenzoic acid (2-AA) and sodium cyanoborohydride was then added to the PNGase F-treated glycans and the mixture was incubated for ~80° C. for about 75 minutes. After incubation, the mixtures were centrifuged to obtain a pellet of precipitated protein. Supernatants were collected and placed in vials.

The glycans were separated by HILIC, in line with a fluorescence detector: Glycans were injected and bound to the column in high organic conditions (Mobile Phase A and Mobile Phase B were ammonium formate and acetonitrile, respectively) and then eluted with an increasing gradient of an aqueous ammonium formate buffer. High resolution was achieved using a 1.7 μm small particle column format and 150 mm column length. The total run time, including column re-equilibration was 155 minutes.

Example 2

This example demonstrates the effects of increasing glucose and fucose levels in the culture medium on TAF %.

Cells expressing an antibody comprising a light chain of SEQ ID NO: 1 and a heavy chain of SEQ ID NO: 2 were added to a bioreactor containing one of three culture media: a control culture medium, a first test culture medium, and a second test culture medium. The first test culture medium was identical to the control culture medium, except that it contained twice the amount of glucose, and the second test culture medium was the control culture medium with 0.5 g/L fucose. Each of the culture media lacked mannose. The cell culture was maintained for 12 days at a pH between 6.85 and 7.05.

Media samples were periodically taken from the bioreactors for measurement of glucose concentration, TAF levels and ADCC levels. TAF and/or afucosylated (Afuc) glycan levels were assayed via an HILIC N-glycan mapping procedure, and the ability to stimulate ADCC was tested using an in vitro assay. The results are shown in TABLE 1 below.

TABLE 1

| Culture Medium | TAF level (%) | ADCC (%) |
| --- | --- | --- |
| Targeted Range | 2.0-4.2% | 69-97% |
| Control | 4.00 ± 0.23% | ~100% |
| First Test | 5.87 ± 0.23% | 152 ± 15% |
| Second Test | ~3.4 % | ~85% |

ADCC levels are expressed as %ages relative to the ADCC level achieved with the control, which is a commercially-available antibody having the same amino acid sequence.

Figure 3:
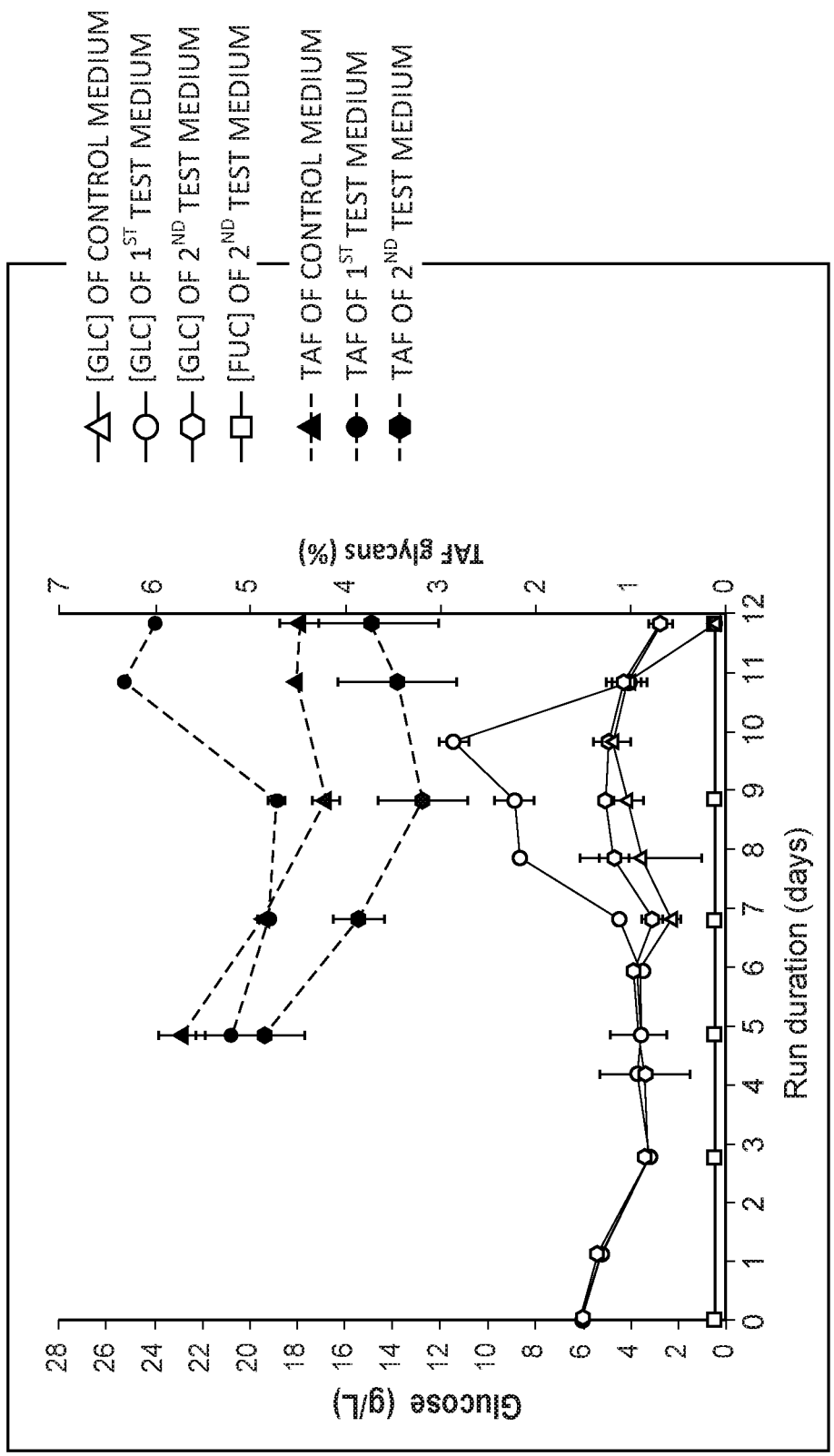
FIG. 3 is a graph depicting (A) the glucose concentration (g/L) of the cell culture using a control medium (line with open triangles), a first test medium (line with open circles), and a second test medium (line with open hexagons), over the course of the cell culture run, (B) the fucose concentration (g/L) of the cell culture using the second test medium (line with open squares) over the cell culture run, and (C) the TAF glycan levels (%) of the cell culture using the control medium (dotted line with closed triangles), the first test medium (dotted line with closed circles), and second test medium (dotted line with closed hexagons), over the course of the cell culture run.

Glucose concentrations were determined throughout the culture run and these measurements were plotted as a function of time and in relation to TAF levels of the antibodies produced in each cell culture medium type. The results are shown in FIG. 3. As shown in this figure, the antibodies produced by cells cultured in the first test culture demonstrated an increase in TAF, which increase corresponded with the increase in glucose levels in the cell culture. These results (and the results of TABLE 1) suggest that glucose can affect TAF levels and ADCC.

The antibodies produced by cells cultured in the second test culture medium comprising 0.5 g/L fucose exhibited ~1% decrease in TAF (FIG. 3). As shown in FIG. 3, the fucose concentration did not change much over the 12-day run, likely because fucose uptake by cells was negligible.

Figure 4:
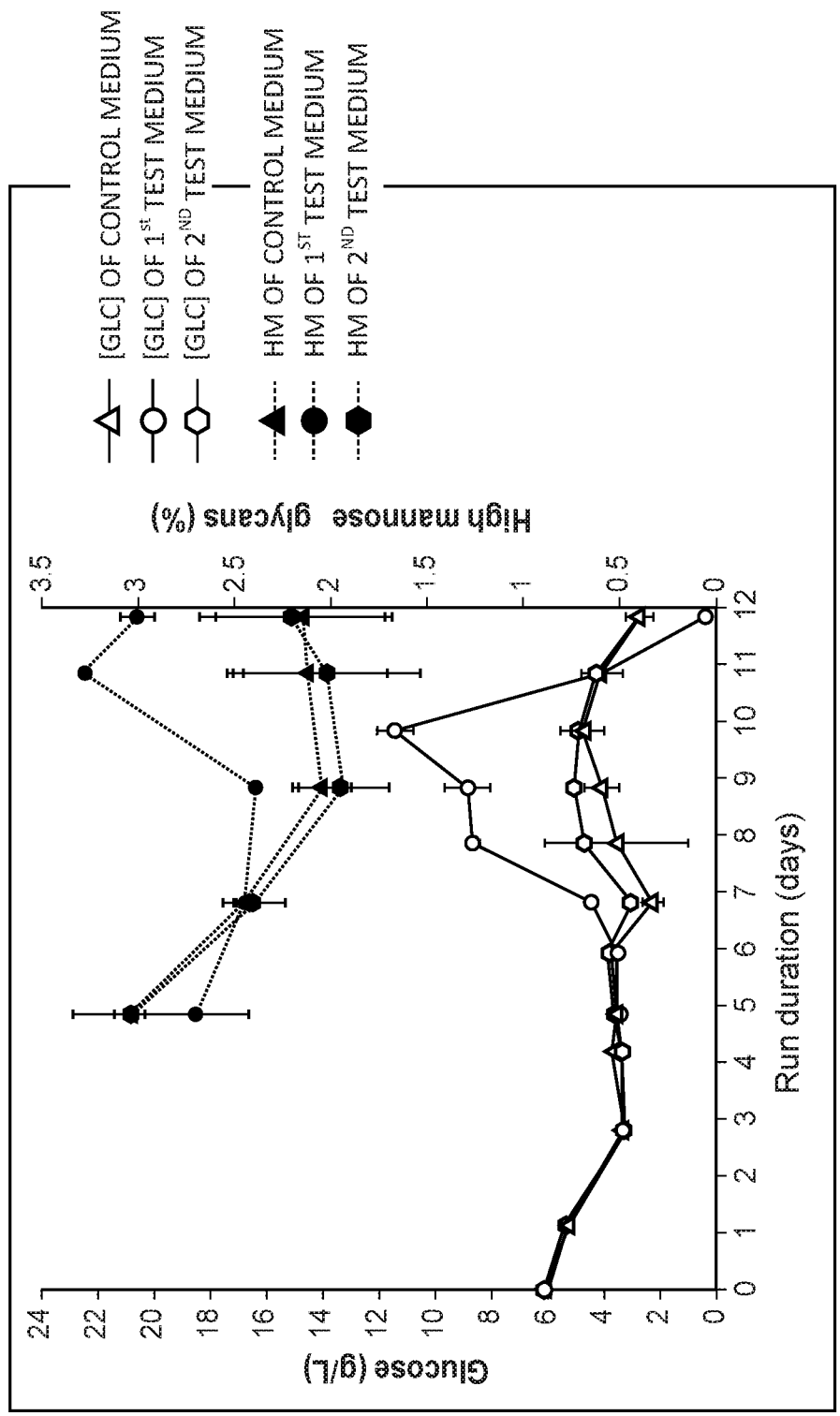
FIG. 4 is a graph depicting (A) the glucose concentration (g/L) of the cell culture using a control medium (line with open triangles), a first test medium (line with open circles), and a second test medium (line with open hexagons), over the course of the cell culture run, and (B) the high mannose (HM) glycan levels (%) of the cell culture using the control medium (dotted line with closed triangles), the first test medium (dotted line with closed circles), and second test medium (dotted line with closed hexagons), over the course of the cell culture run.

Further analysis of the separate glycan species of the antibodies produced in each of the different culture media was carried out. Interestingly, as shown in FIG. 4, the % high mannose (HM) glycans increased when the cells were cultured in the first test medium which contained 2-times the amount of glucose compared to control medium. This increase in % HM glycans was not achieved by cells cultured in the second test medium containing fucose. As shown in FIG. 4, the % HM glycans of antibodies produced by cells cultured in the second test medium containing fucose was about the same as the % HM glycans of the antibodies produced by cells cultured in the control medium.

Figure 5:
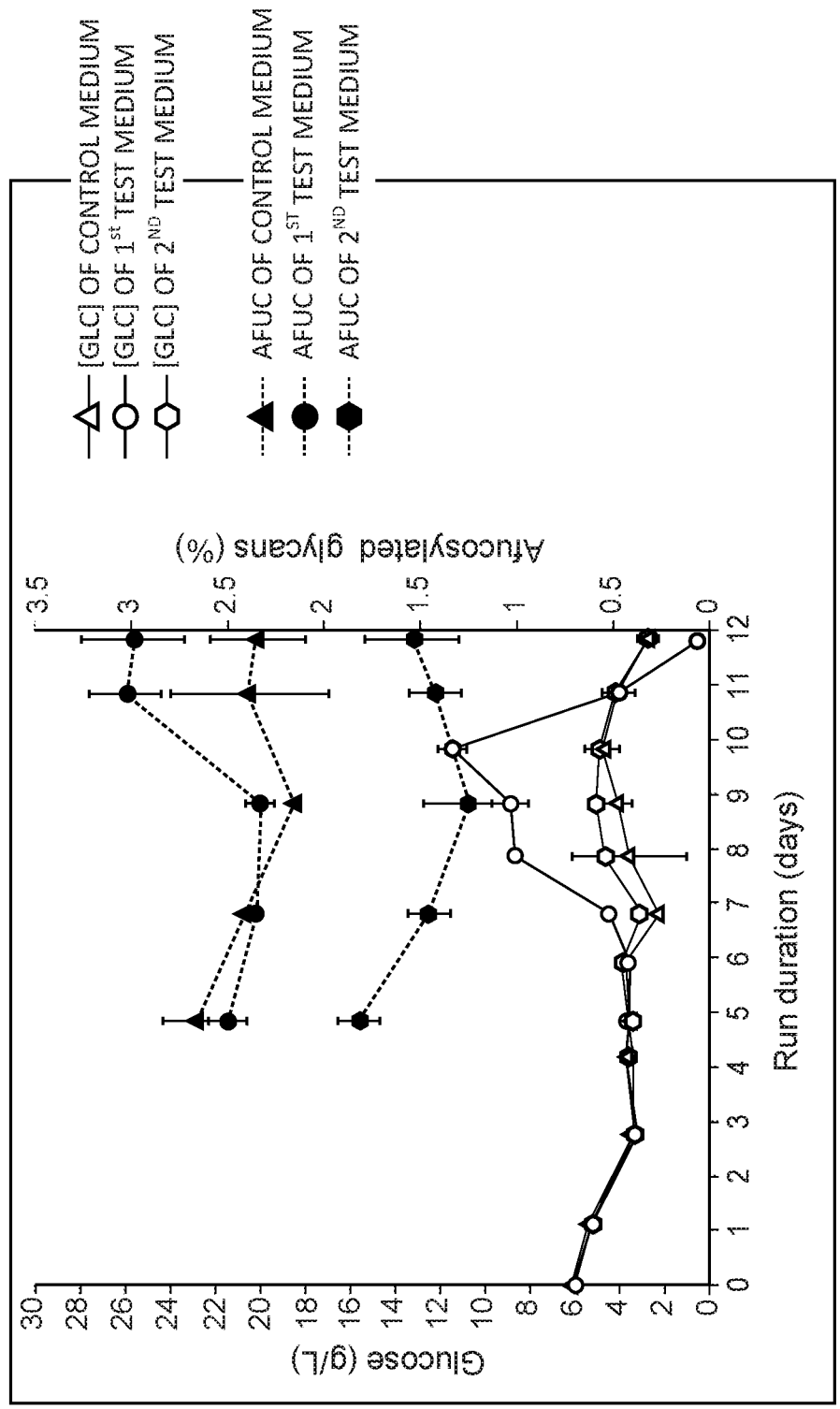
FIG. 5 is a graph depicting (A) the glucose concentration (g/L) of the cell culture using a control medium (line with open triangles), a first test medium (line with open circles), and a second test medium (line with open hexagons), over the course of the cell culture run, and (B) the afucosylated (afuc) glycan levels (%) of the cell culture using the control medium (dotted line with closed triangles), the first test medium (dotted line with closed circles), and second test medium (dotted line with closed hexagons), over the course of the cell culture run.

The effects of culturing in medium containing twice the amount of glucose (first test medium) or containing fucose (second test medium) on the % afucosylated glycans was similar to those effects on the % TAF glycans. As shown in FIG. 5, cells cultured in the first test medium comprising the higher glucose concentration demonstrated an increase in afucosylated glycans, whereas cells cultured in the second test medium comprising fucose produced antibodies with decreased afucosylated glycans.

This example demonstrated that glucose and fucose are levers that can be used to modulate high mannose and afucosylated glycan levels as well as impact ADCC.

Example 3

This example demonstrates additional studies demonstrating glucose and fucose as levers for the modulation of TAF levels and ADCC.

Figure 6:
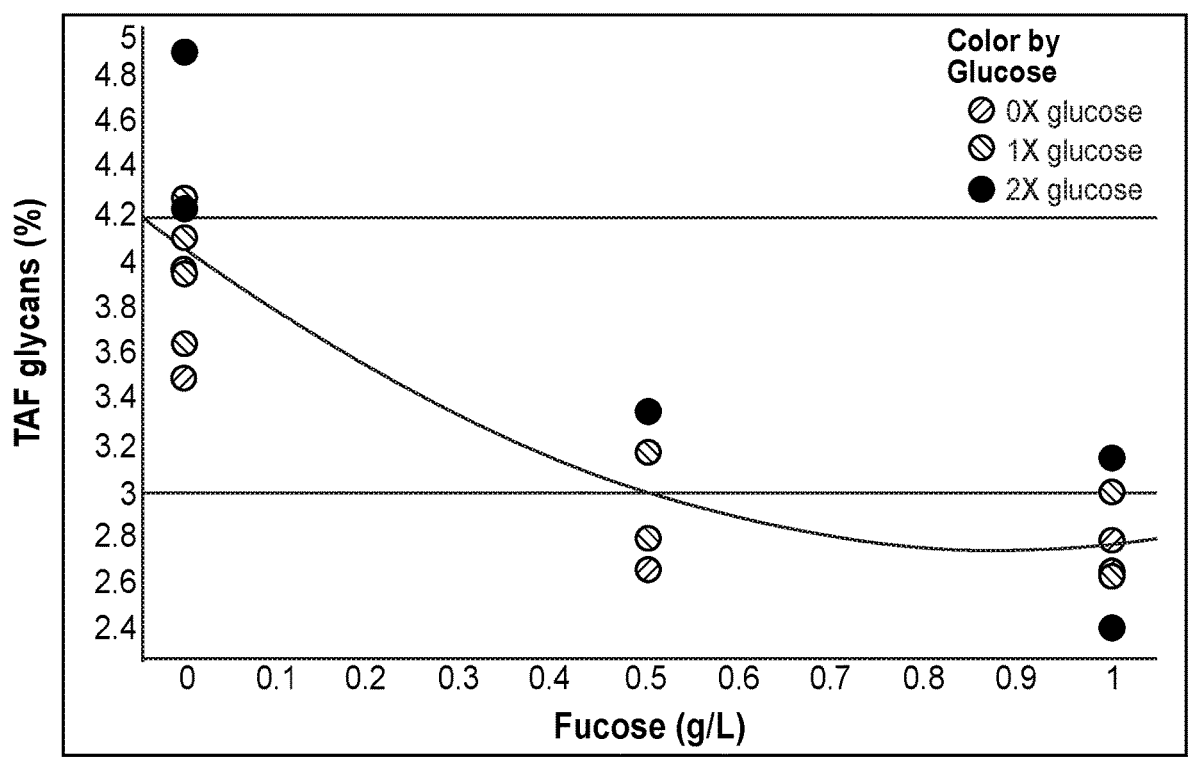
FIG. 6 is a graph of the TAF glycan levels (%) as a function of fucose concentration (g/L) in the cell culture medium containing 0X glucose, 1X glucose or 2X glucose.
Figure 7:
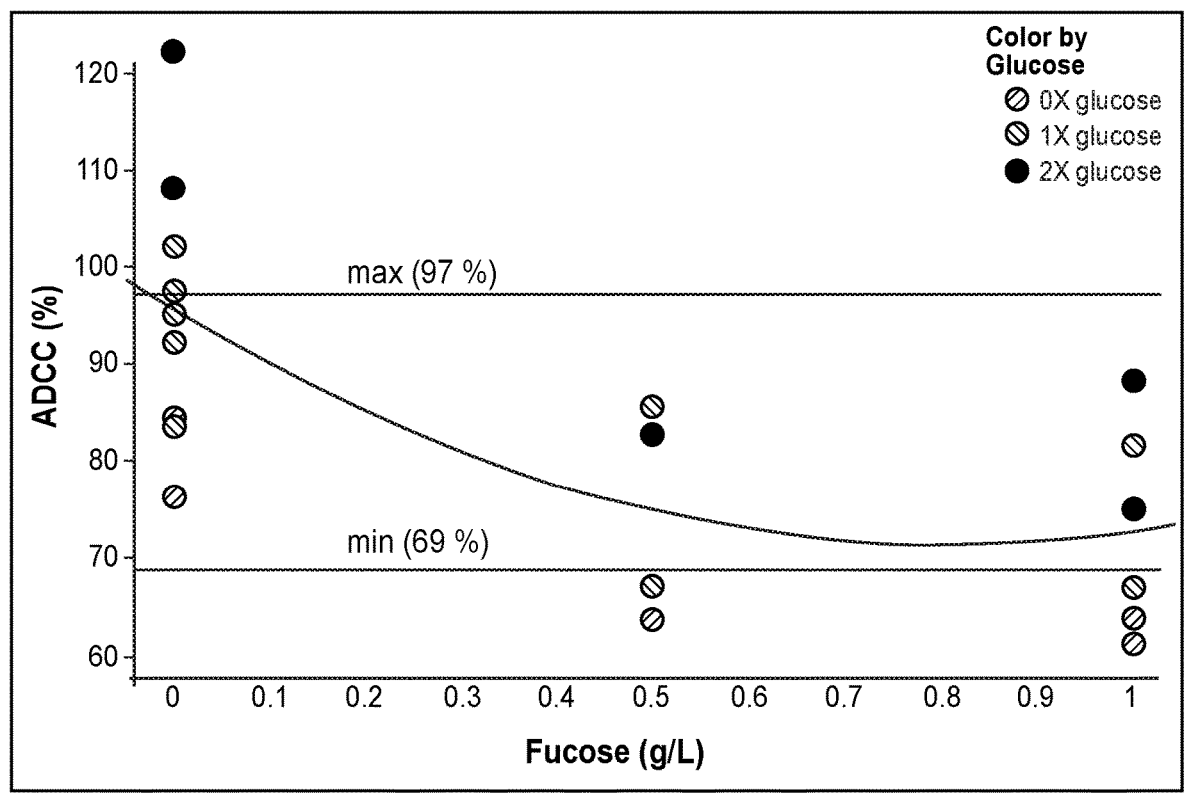
FIG. 7 is a graph of the ADCC levels (expressed as % relative to a control antibody having the same amino acid sequence) as a function of fucose concentration (g/L) in the cell culture medium containing 0X glucose, 1X glucose or 2X glucose.

A follow-up multivariate full factorial experiment was designed to (1) elucidate the main, interaction and quadratic effects of fucose and glucose variables and (2) find amounts for these variables that would lead to modified TAF glycan and ADCC levels. Fucose was evaluated in culture media at concentrations of 0 g/L, 0.5 g/L and 1 g/L. Glucose was fed at 0X, 1X (control) and 2X rates. 0X meant that there was no glucose stock solution added to the cultures and this translated to a residual glucose concentration of ~1 g/L after Day 6 of cell culture. Glucose was supplied only through the media, which contained 12 g/L of the sugar. At 1X feeding, glucose was maintained at an average concentration of 3±1 g/L after glucose feed initiation. In 2X feeding, the average glucose levels were maintained at 6±1 g/L. The results indicate that fucose concentrations can be changed to impact the TAF levels (FIG. 6) and ADCC levels (FIG. 7).

Figure 8:
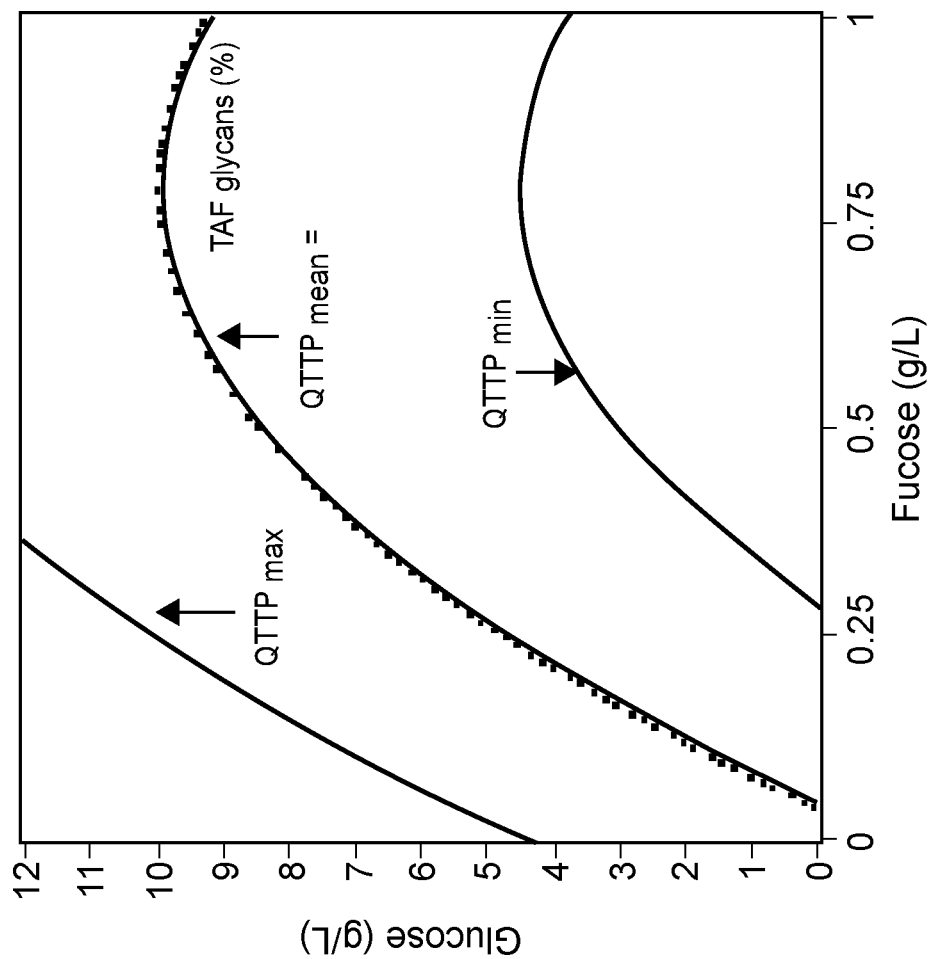
FIG. 8 is a graph illustrating a model of the effects of glucose and fucose on TAF glycan levels (%). The min, max, and mean TAF according to the QTPP are shown. The equation below the graph shows the mathematical relationship between glucose, fucose and TAF.
Figure 9A:
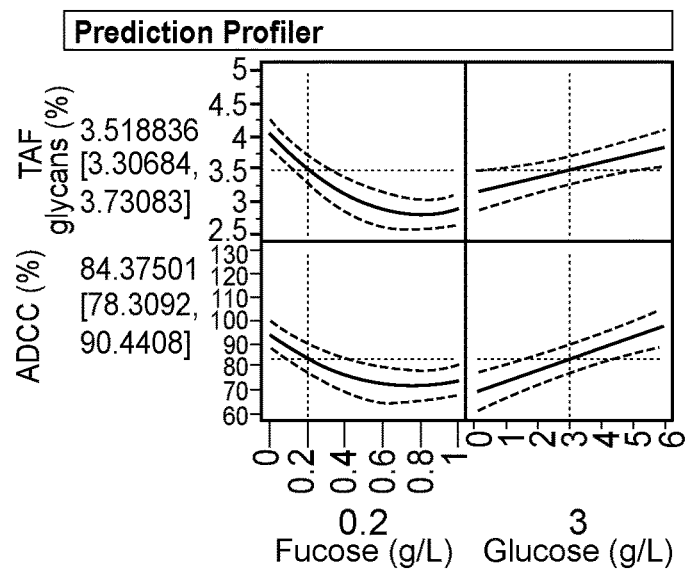
FIG. 9A is a series of graphs showing: (i) TAF glycan levels (%) as a function of fucose concentration (g/L) in the cell culture medium (top left quadrant) or as a function of glucose concentration (g/L) in the cell culture medium (top right quadrant) and (ii) ADCC levels (expressed as % relative to a control antibody having the same amino acid sequence) as a function of fucose concentration (g/L) in the cell culture medium (bottom left quadrant) or as a function of glucose concentration (g/L) in the cell culture medium (bottom right quadrant). The range of TAF glycan levels (%) is 3.30684 to 3.73083 and the range of ADCC levels is 78.3092-90.4408. At 0.2 g/L fucose and 3.0 g/L glucose, the TAF glycan level (%) was 3.518836, and the ADCC level (%) was 84.37501.
Figure 9B:
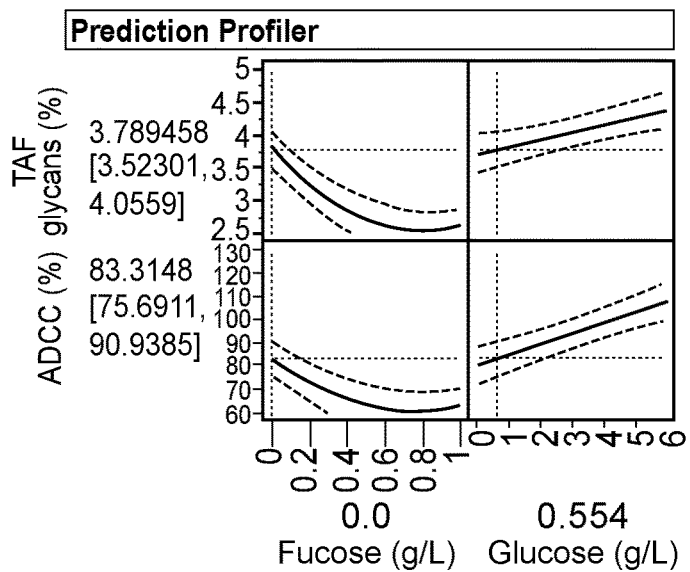
FIG. 9B is a series of graphs showing: (i) TAF glycan levels (%) as a function of fucose concentration (g/L) in the cell culture medium (top left quadrant) or as a function of glucose concentration (g/L) in the cell culture medium (top right quadrant) and (ii) ADCC levels (expressed as % relative to innovator or commercially-available antibody) as a function of fucose concentration (g/L) in the cell culture medium (bottom left quadrant) or as a function of glucose concentration (g/L) in the cell culture medium (bottom right quadrant). The range of TAF glycan levels (%) is 3.52301 to 4.0559 and the range of ADCC levels is 75.6911-90.9385. At 0 g/L fucose and 0.554 g/L glucose, the TAF glycan level (%) was 3.789458, and the ADCC level (%) was 83.3148.
Figure 9C:
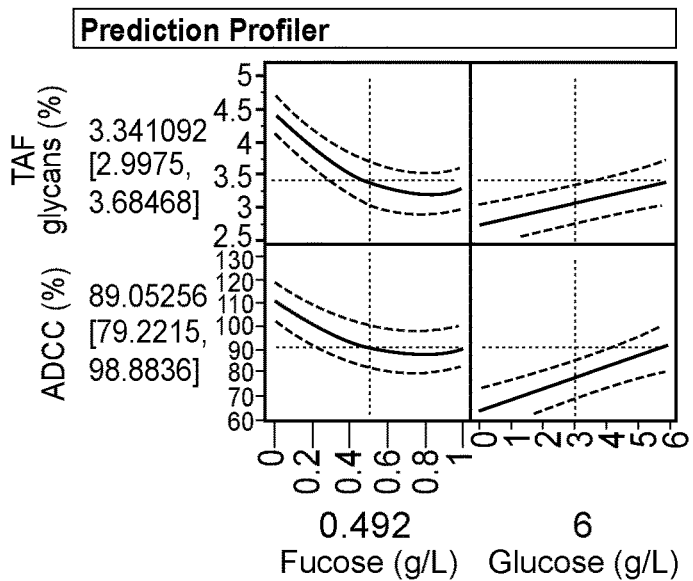
FIG. 9C is a series of graphs showing: (i) TAF glycan levels (%) as a function of fucose concentration (g/L) in the cell culture medium (top left quadrant) or as a function of glucose concentration (g/L) in the cell culture medium (top right quadrant) and (ii) ADCC levels (expressed as % relative to innovator or commercially-available antibody) as a function of fucose concentration (g/L) in the cell culture medium (bottom left quadrant) or as a function of glucose concentration (g/L) in the cell culture medium (bottom right quadrant). The range of TAF glycan levels (%) is 2.9975-3.68468 and the range of ADCC levels is 79.2215-98.8836. At 0.492 g/L fucose and 6.0 g/L glucose, the TAF glycan level (%) was 3.341092, and the ADCC level (%) was 89.05256.

In these experiments, glucose concentration was controlled at 3±1 g/L post feed initiation (i.e., after Day 6). If glucose concentrations exceeded 4 g/L, no additional glucose was added and the cells were to rely on residual glucose in the bioreactor and glucose coming through the perfusion media until the glucose level fell within the control range. Based on these experiments, TAF values were predicted for the different fucose and glucose concentrations, according to a model shown in FIG. 8. The model demonstrates that the Quality Target Product Profile (QTTP) may be achieved upon culturing the cells in a culture medium comprising about 0.1 g/L to about 1.0 g/L fucose and/or about 0.5 g/L to about 4.0 g/L glucose. TAF values were predicted for the following different fucose and glucose concentrations utilizing this model: 0.2 g/L fucose and 3 g/L glucose, 0 g/L fucose and 0.554 g/L glucose; and 0.492 g/L fucose and 6 g/L glucose. FIGS. 9A-9C. These results suggested that are several ways to arrive at the desired TAF levels and ADCC levels.

To confirm the predictions of FIGS. 9A-9C, additional experiments were carried out. A summary of the experiments is provided in TABLE 2.

TABLE 2

| Condition | Fucose (g/L) | Glucose (g/L) | TAF (95% CI) | TAF actual | ADCC (95% CI) | ADCC actual |
|---|---|---|---|---|---|---|
| 1 | 0 | 0X | 3.50-4.06 | 3.50 | 75.7-90.9 | 80.13 |
| 2 (control) | 0 | 1X | 3.68-4.22 | 3.84 | 84.5-101.1 | 100.3 |
| 3 | 0.2 | 1X | 3.30-3.73 | 3.35 | 78.3-90.4 | 85.9 |
| 4 | 0.5 | 1X | 2.67-3.30 | 2.94 | 66.8-83.14 | 76.2 |

0X, glucose concentration was measured at ~1 g/L post Day 6;
1X, glucose concentration was measured at ~3 ± 1 g/L;
2X, glucose concentration was measured at ~6 ± 1 g/L.

This example demonstrated that both glucose concentration and fucose concentration are variables that can be manipulated to modify the levels of TAF and ADCC.

Example 4

This example demonstrates the impact of fucose on the cell cultures.

Figure 10:
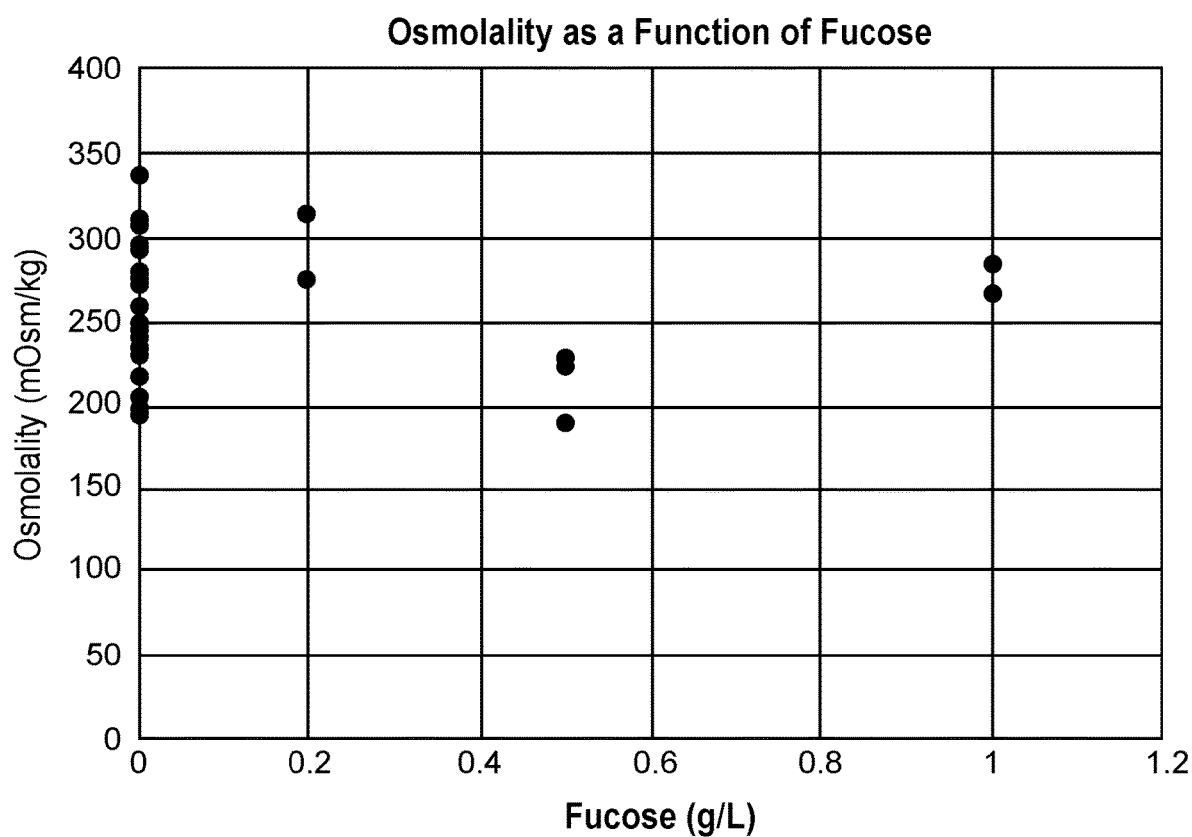
FIG. 10 is a graph of osmolality plotted as a function of fucose concentration.

Additional analyses were performed on the cell cultures described above. For example, osmolality of the cell cultures was measured and ranged from about 175 mOsm/kg to about 345 mOsm/kg. A lack of correlation between cell culture osmolality and fucose concentration was observed. See FIG. 10. As shown in this figure, the addition of fucose to the culture medium does not appear to affect the osmolality in any particular way. That the osmolality greatly varied in the control condition (without fucose) suggests that components in the culture medium (other than fucose) actively affect osmolality.

Figure 11:
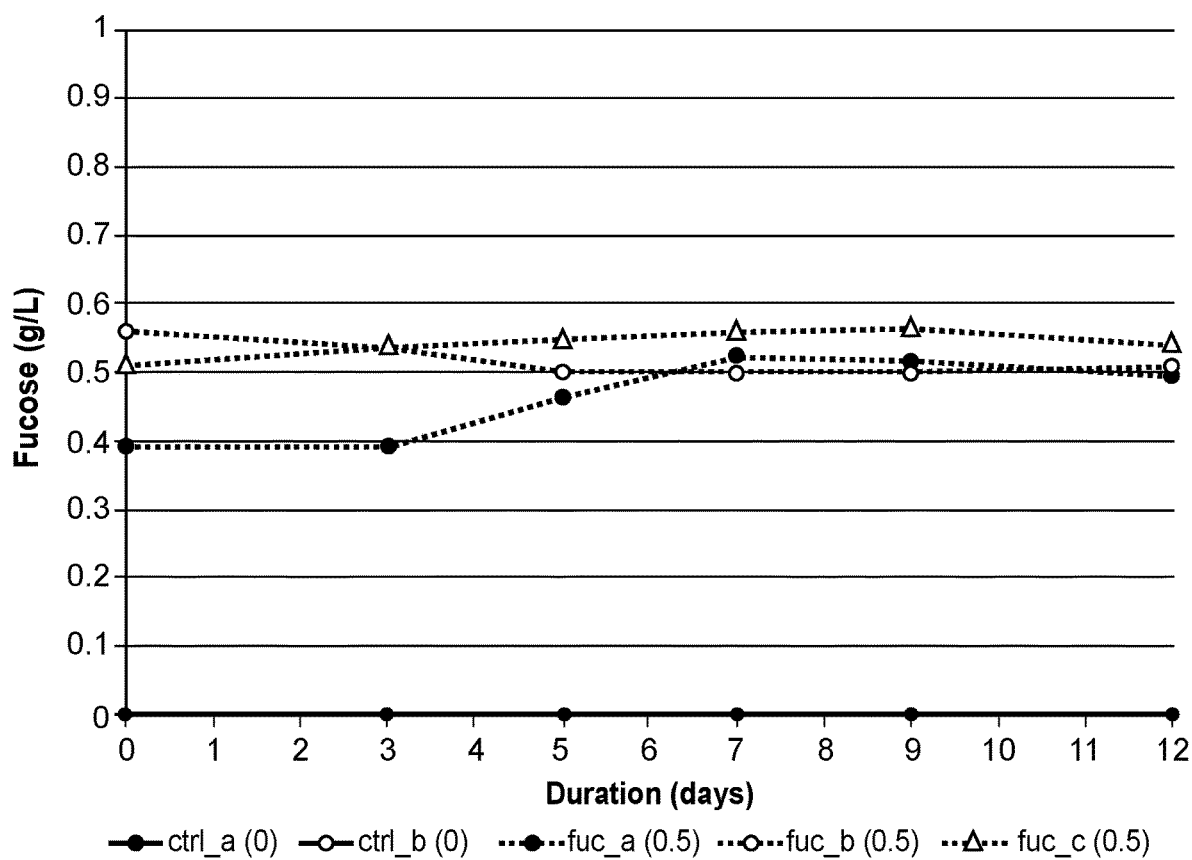
FIG. 11 is a graph of fucose concentration plotted as a function of time (duration) in cell culture.

In one experiment of this fucose study, cells were inoculated into one of five bioreactors, two of which contained culture medium without any fucose (ctrl_a and ctrl_b) and three of which contained culture medium with 0.5 g/L fucose (fuc_a, fuc_b, and fuc_c). Media samples from the five cell cultures were collected throughout the 12-day culture period on Day 0, Day 3, Day 5, Day 7, Day 9, and Day 12. The samples were measured for fucose concentration. As shown in FIG. 11, the concentration of fucose did not substantially change throughout the culture period, suggesting the small and/or slow consumption of fucose during this culture process.

Figure 12:
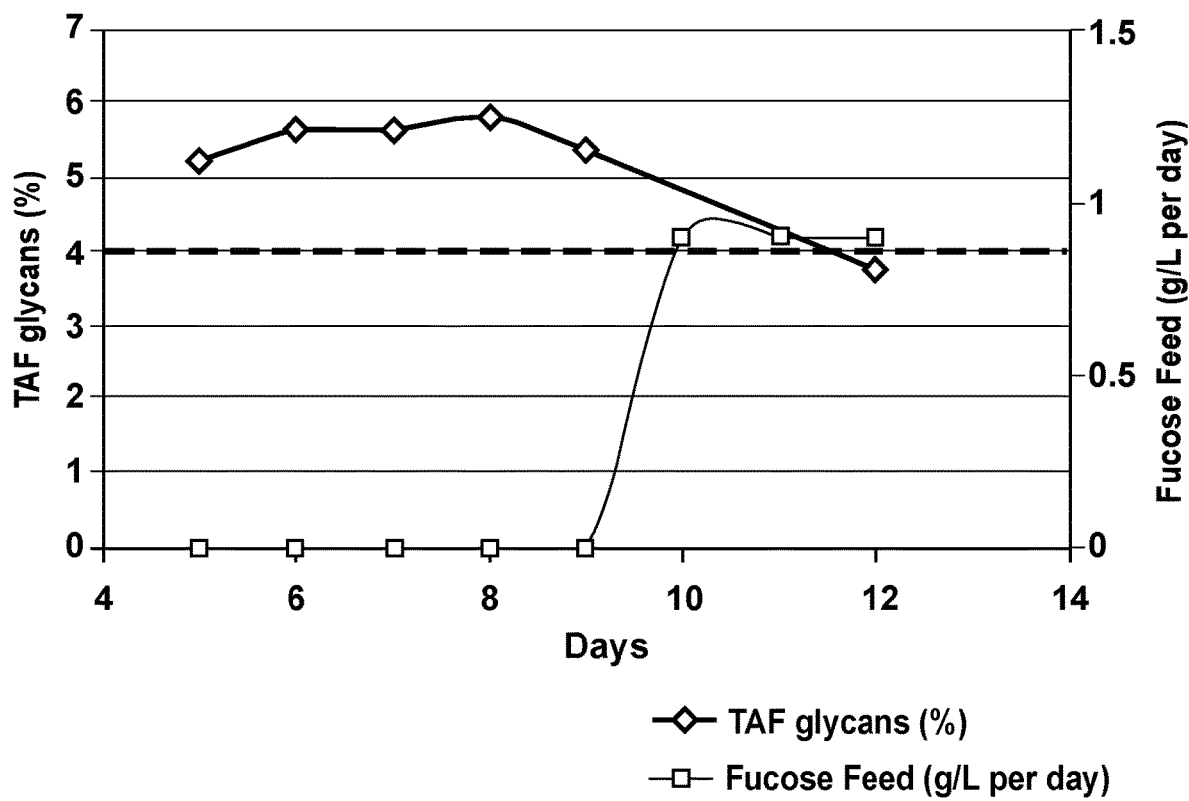
FIG. 12 is a graph of the % TAF and fucose feed, each plotted as a function of time.

In another experiment of this fucose study, cells were maintained in cell culture for 12 days in a culture medium not containing fucose. In this particular experiment, the pH of the cell culture was disturbed from 7.1 causing the TAF % to increase to about 5.5% from Day 5 to ~Day 8. TAF % was measured daily starting Day 5. In an attempt to modulate the TAF levels back to the 4.0% target, fucose was added on the $9^{th}$ day of culture at a feed rate of 0.9 g/L per day. As shown in FIG. 12, the TAF % decreased from about 5.5% upon addition of fucose to the culture medium. The TAF % continued to decrease to ~3.8% on Day 12. These data suggest that fucose addition may occur late in the culture period and still cause TAF % modulation.

This example demonstrated the impact of fucose concentration in the culture medium on the levels of TAF.

Example 5

This example demonstrates that maintenance of glucose in the target range can occur late in the culture period.

Figure 13:
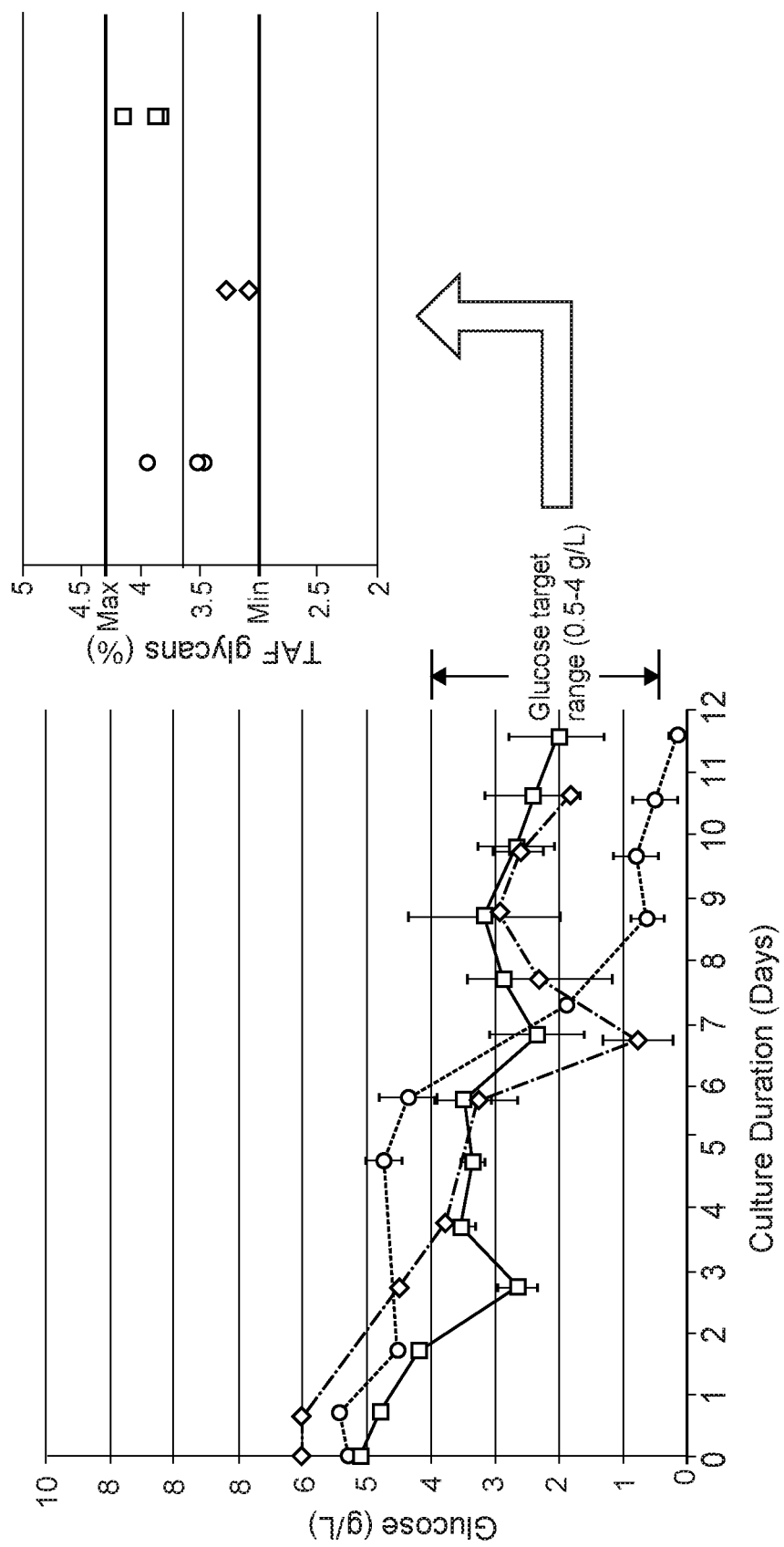
FIG. 13 is a pair of graphs demonstrating that controlling glucose in the target range from Day 6 or earlier yields equivalent TAF results.

Three experiments were carried out to monitor the timing that the targeted glucose range was reached during a 12-day culture period. For each experiment, the initial glucose concentration of each cell culture ranged from about 5.0 g/L to about 6.0 g/L. Glucose concentrations of the cell culture media were monitored on a daily basis. As shown in FIG. 13, each of the cell cultures reached the targeted glucose concentration (0.5 g/L-4.0 g/L) on different days of the culture period. In one experiment (line with open squares), the targeted range was achieved on Day 2. In a second experiment (dotted line with open diamonds), the targeted range was achieved on Day 4, while in a third experiment (dotted line with open circles), the targeted range was reached on Day 6. Despite these differences, each cell culture achieved the targeted range of TAF % (~2.0% to ~4.3%) (see left graph of FIG. 13; third experiment represented by open circles; second experiment represented by open diamonds; first experiment represented by open squares). These data suggest that glucose maintenance can occur later in the culture period to achieve the same TAF levels of cultures maintained earlier during the culture period.

These data demonstrate early and late control of glucose concentrations lead to similar TAF levels.

Example 6

This example demonstrates the effects of lowering the pH of a cell culture on the level of afucosylation of an antibody with and without the addition of fucose.

A sample of a cell culture was removed from a 2000L bioreactor and used to inoculate parallel 3L bioreactors. The 2000L and 3L bioreactors were fed using a continuous fed-batch process with Feed A and Feed B for 12 days. Two of the 3L bioreactors were fed with fucose to a final concentration of 1.0 g/L on Day 5. Afucosylation levels were measured as described in Example 1 and the results are provided in Table 3.

TABLE 3

| pH | Fucose Addition | % afucosylation |
|---|---|---|
| 7.09 | − | 6.29 |
| 7.09 | − | 6.317 |
| 7.07 | − | 6.559 |
| 7.07 | + | 4.384 |
| 7.12 | − | 7.13 |
| 7.13 | − | 7.24 |
| 7.18 | − | 8.365 |
| 7.19 | − | 7.917 |
| 7.18 | + | 6.183 |

As shown in Table 3, in the absence of the addition of fucose, when the pH was below 7.1, the average % afucosylation was 6.39, whereas when the pH was above 7.10 but below 7.15, the average % afucosylation was higher (% afucosylation=7.185). When the pH was above 7.15, the average % afucosylation was yet even higher ((% afucosylation=8.276). Thus, a lower pH was associated with a lower % afucosylation.

When fucose was added to the culture medium (to achieve a final concentration of 1.0 g/L fucose, the % afucosylation was substantially decreased at both a lower pH (7.07) and a higher pH (7.18). For each of these pH levels, when fucose was added, the average decrease in % afucosylation was 2.18%.

These results suggest that lowering the pH of the cell culture medium and/or adding fucose to the cell culture medium leads to a lowered percent afucosylation. When both pH was lowered and fucose was added to the cell culture medium, a greater reduction of percent afucosylation was observed.

Example 7

This example further demonstrates the effects of lowering the pH of a cell culture on the level of afucosylation of an antibody with and without the addition of fucose.

A sample of a cell culture from a 2000L bioreactor was used to inoculate parallel 3L bioreactors. The 2000L and 3L bioreactors were fed using a continuous fed-batch process using Feed A and Feed B for 12 days. Some of the bioreactors (i.e., cell culture) were fed with fucose to a final concentration of 0.25, 0.5 or 1 g/L on Day 5. Afucosylation levels were measured as described in Example 1 and the results are provided in FIG. 14.

Figure 14:
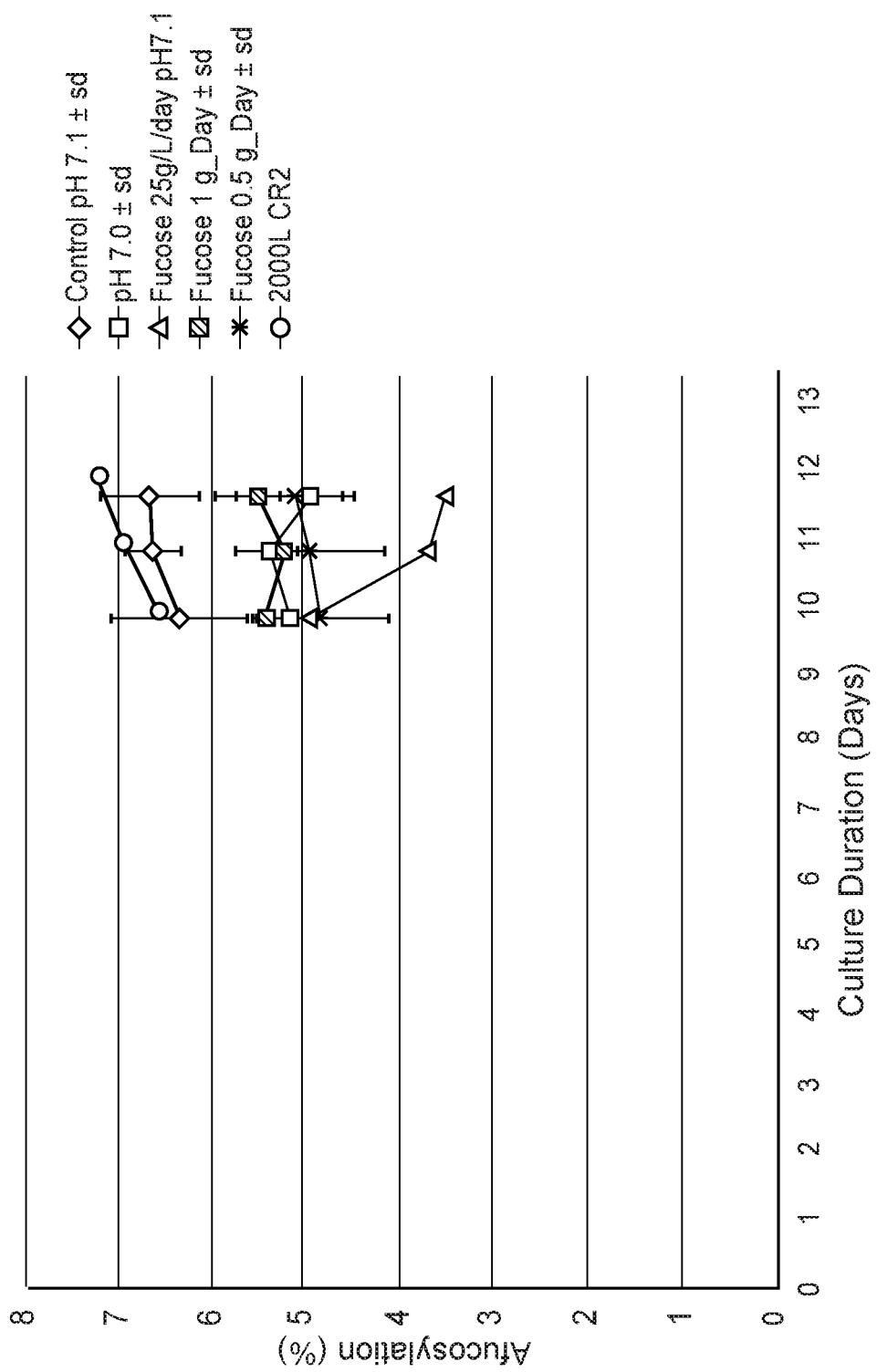
FIG. 14 is a graph of % afucosylation plotted as a function of culture time.

As shown in FIG. 14, the control 3L bioreactor (Control pH 7.1) exhibited a similar level of afucosylation as the original 2000L bioreactor. Both exhibited % afucosylation of about 6.5% or greater. The addition of fucose at any of the tested levels led to a substantial decrease in % afucosylation (5.5% or lower). The percent afucosylation was lowest with the addition of 0.25 g/L of fucose.

Also, as shown in FIG. 14, lowering the pH from 7.1 to 7.0, without adding fucose to the culture medium, also led to a decrease in afucosylation of at least about 1.0%.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A method of producing an antibody composition, wherein the level of total afucosylated (TAF) glycans in the antibody composition is less than 10%, the method comprising maintaining glycosylation-competent cells comprising a nucleic acid encoding an antibody of the antibody composition in a cell culture medium wherein;
   a. the cell culture medium comprises fucose at a concentration of 0.17 g/L to 1.0 g/L or 0.1 g/L to 1.0 g/L and a pH of the cell culture medium is 6.85 to 7.05, or greater than 7.05 and less than 7.20, and
   b. the glycosylation-competent cells are not genetically modified to alter activity of an enzyme of the de novo pathway or the salvage pathway, and
   c. the method further comprises adding glucose to the cell culture medium according to a glucose feeding schedule, wherein the glucose feeding schedule is initiated at 4 to 6 days post-cell culture inoculation to achieve an average glucose concentration of 10 g/L or less in the cell culture medium or based on the concentration of fucose in the cell culture medium as calculated by Formula I:

$$T=3.354-1.388F+0.111G+[F-0.4375]\times[1.9527(F-0.4375)] \quad \text{(Formula I)}$$

wherein T is the targeted % total afucosylated (TAF) glycans in the antibody composition and is 2.5% to 6%, 2.75% to 5.5%, or 3% to 5%, F is the concentration (g/L) of fucose in the medium, and G is the average glucose concentration (g/L) in the medium.

2. The method of claim 1, wherein fucose is present in the culture medium at a concentration less than 0.75 g/L.

3. The method of claim 2, wherein the cell culture medium comprises less than 0.6 g/L fucose or 0.2 g/L to 0.5 g/L fucose.

4. The method of claim 1, wherein the fucose is present in the culture medium the entire duration the glycosylation-competent cells are maintained in cell culture.

5. The method of claim 1, comprising maintaining the glycosylation-competent cells in a first cell culture medium for an initial time period and subsequently maintaining the glycosylation-competent cells in a second cell culture medium, wherein the first cell culture medium does not comprise fucose at a concentration of 0.1 g/L to 1.0 g/L and the second cell culture medium comprises fucose at a concentration of 0.1 g/L to 1.0 g/L.

6. The method of claim 5, wherein fucose is added to the first culture medium on the $6^{th}$ day post-cell culture inoculation to obtain the second cell culture medium.

7. The method of claim 1, wherein (i) the concentration of fucose is 0.2±0.1 g/L and the average glucose concentration is 2 to 4 g/L; (ii) the concentration of fucose is 0.5±0.1 g/L and the average glucose concentration is 3 to 6 g/L; or (iii) the concentration of fucose is 0.75±0.1 g/L and the average glucose concentration is 4.5 to 9 g/L.

8. The method of claim 1, wherein the pH of the cell culture medium is 6.85 to 7.05.

9. The method of claim 8, wherein the pH of the cell culture medium is 6.90 to 7.00.

10. The method of claim 1, wherein (A) the level of TAF glycans is 2% to 6%, (B) the level of high mannose glycans in the antibody composition is less than 3.5%, and/or (C) the level of afucosylated glycans in the antibody composition is less than 3.5%.

11. The method of claim 10, wherein (A) the level of TAF glycans is 2% to 5% or 2% to 4%, (B) the level of high mannose glycans in the antibody composition is 0.7% to 3.0%, and/or (C) the level of afucosylated glycans in the antibody composition is 0.8% to 2.8%.

12. The method of claim 1, wherein the glycosylation-competent cells produce IgG antibodies.

13. The method of claim 12, wherein the IgG1 antibodies are specific for a tumor-associated antigen comprising SEQ ID NO. 3.

14. The method of claim 12, wherein the glycosylation-competent cells produce IgG1 antibodies.

15. The method of claim 1, wherein the culture medium does not comprise mannose.

* * * * *